(12) United States Patent
Meares et al.

(10) Patent No.: US 7,118,745 B1
(45) Date of Patent: Oct. 10, 2006

(54) ENGINEERING ANTIBODIES THAT BIND IRREVERSIBLY

(75) Inventors: Claude Meares, Davis, CA (US); Albert Chmura, Davis, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 09/671,953

(22) Filed: Sep. 27, 2000

Related U.S. Application Data

(60) Provisional application No. 60/208,684, filed on May 31, 2000, provisional application No. 60/156,194, filed on Sep. 27, 1999.

(51) Int. Cl.
*A61K 39/40* (2006.01)
*A61K 39/395* (2006.01)
*C07K 16/00* (2006.01)

(52) U.S. Cl. .......... 424/179.1; 424/1.11; 424/1.149; 424/1.53; 424/1.65; 424/1.69; 530/387.1; 530/387.3; 530/388.1; 530/388.8

(58) Field of Classification Search .......... 530/387.1, 530/387.3, 388.85, 391.5, 388.1, 388.8; 424/130.1, 424/133.1, 136.1, 156.1, 175.1, 179.1, 1.11, 424/1.49, 1.53
See application file for complete search history.

(56) References Cited

U.S. PATENT DOCUMENTS

| | | | |
|---|---|---|---|
| 4,678,667 A | 7/1987 | Meares et al. |
| 4,722,892 A | 2/1988 | Meares et al. |
| 5,541,287 A | 7/1996 | Yau et al. |
| 5,747,654 A | 5/1998 | Pastan et al. |
| 5,789,554 A | 8/1998 | Leung et al. |
| 5,837,242 A | 11/1998 | Holliger et al. |

FOREIGN PATENT DOCUMENTS

WO    WO 95/15979    6/1995

OTHER PUBLICATIONS

Paul., Fundamental Immunology Raven Press, NY, chapter 8, p. 242, 1993.*
Rudikoff et al., Proc. Natl. Acad. Sci. USA 79:1979-83, 1982.*
Orlandi et al., Proc. Natl. Acad. Sci. USA 86:3833-3837, 1989.*
M. Chinol, et al., "Biodistribution in tomour-bearing mice of two $^{90}$Y-labelled biotins using three-step tumour targeting," *Nuclear Medicine Comm.*, 18:176-182 (1997).
David A. Goodwin, et al., "Pre-targeted immunoscintigraphy of murine tumors with indium-111-labeled bifunctional haptens," *J. Nucl. Med.*, 29:226-234 (1998).
David A. Goodwin, et al., "Pretargeted immunodcinigraphy: Effect of hapten valency on murine tumor uptake," *J Nucl. Med.*, 33:2006-2013 (1992).
D. J. Hnatowich, et al., "Investigations of avidin and biotin for imaging applications," *J. Nucl. Med.*, 28:1294-1302 (1987).
H. P. Kalofonos, et al., "Imaging of tumor in patients with indium-111-labeled biotin and streptavidin-conjugated antobodies: Preliminary communication," *J. Nucl. Med.*, 31:1791-1796 (1990).
Alexander I. Klinaov, et al., "Blood clearance of radiolabeled antibody: Enhancement by lactosamination and treatment with biotin-avidin or anti-mouse IgG antibodies," *J. Nucl. Med.*, 29:1951-1956 (1988).
J. Ian Marsh, et al., "Streptavidin and biotin as potential tumor imaging agents," *J. Nucl. Med.*, 29(5):728-729 (1988).
Damon L. Meyer, et al., "Kinetics of the dissociation of indium-(p-substituted-benzyl)ethylenediaminetetraacetic acid hapten analogues from the monoclonal anti-hapten antibody CHA255," *Bioconjuagate Chem.*, 1:278-284 (199).
Jeffrey T. Owens, et al., "Mapping the promoter DNA sites proximal to conserved regions of $\sigma^{70}$ in an *Escherichia coli* RNA polymerase-lacUV5 open promoter complex," *Biochemistry*, 37:7670-7675 (1998).
Jeffrey T. Owens, et al., "Mapping the $\sigma^{70}$ subunit contact sites on *Escherichia coli* RNA polymerase with a $\sigma^{70}$-conjugated chemical protease," *Proc. Natl. Acad. Sci. USA*, 95:6021-6026 (1988).
G. Paganelli, et al., "Three-step monoclonal antibody tumor targeting in carcinoembyonic antigen-positive patients," *Cancer Research*, 51:5960-5966 (1991).
G. Paganelli, et al., "Monoclonal antibody pretargetting techniques for tumour localization: the Avidin-biotin system," *Nuclear Medicine Comm.*, 12:211-234 (1991).
Dayton T. Reardan, et al., "Antibodies against metal chelates," *Nature*, 316:265-268 (1985).
Bruno Robert, et al., Cytokine targeting in tumors using a bispecific antibody directed against carcinoembryonic antigen and tumor necrosis factor $\alpha^1$, *Cancer research*, 56:4758-4765 (1996).
Eric Rouvier, et al., "Targeting medullary thyroid carcinomas with bispecific antibodies and bivalent haptens," *Horm. Res.*, 47:163-167 (1997).
B. Schechter, et al., "Indirect immunotargeting of CIS-PT to human epidermoid carcinoma KB using the avidin-biotin system," *Int. J. Cancer*, 48:167-172 (1991).
Vladimir V. Sinitsyn, et al., "Rapid blood clearance of biotinylated IgG after infusion of avidin," *J. Nucl. Med.*, 30:66-69 (1989).
Dwight R. Stickney, et al., "Bifunctional antibody: A binary radiopharmaceutical delivery system for imaging colarectal carcinoma," *Cancer Research*, 51:6650-6655 (1991).
Fan Yuan, et al., "Pharmacokinetic analysis of two-step approaches using bifunctional and enzyme-conjugated antibodies," *Cancer Research*, 51:3119-3130 (1991).

* cited by examiner

*Primary Examiner*—Larry R. Helms
*Assistant Examiner*—Brandon Fetterolf
(74) *Attorney, Agent, or Firm*—Morgan, Lewis & Bockius LLP

(57) ABSTRACT

The present invention provides a mutant antibody comprising a reactive site not present in the wild-type of the antibody and a complementarity-determining region that specifically binds to a metal chelate, wherein the reactive site is in a position proximate to or within the complementarity-determining region.

20 Claims, 15 Drawing Sheets

```
CTA CAA CTG AAT AGT CTG AGG TCT GAG GAC ACG GCC TTG TAT TTC TGT GCA AGT CAT CGG
GAT GTT GAC TTA TCA GAC TCC AGA CTC AGA CTG TGC CGG AAC ATA AAG ACA CGT TCA GTA GCC
Leu Gln Leu Asn Ser Leu Arg Ser Glu Asp Thr Ala Leu Tyr Phe Cys Ala Ser His Arg
                                                                            └─────
                                                                              CDR3

CCCGGGAGG
                                                                     └ApaI
                AGA CGT CGG TTT TGC TG
                TCT GCA GCC AAA ACG ACA CCC CCA
TTT GTT CAC TGG GGC CAC GGG ACT CTG GTC ACT GTC TCT AGA CGT CGG TTT TGC TGT GCA GCC AAA ACG ACA CCC CCA
AAA CAA GTG ACC CCG GTG CCC TGA GAC CAG TGA CAG AGA TCT CGT GCC TTT TGC TGT GGG GGT
Phe Val His Trp Gly His Gly Thr Leu Val Thr Val Ser Ala Ala Lys Thr Thr Pro Pro
            └──                                          └────
              FR4                                           CH1
```

```
                SstI
CTCAGAGCTC
GCT GTT GTG ACT CAG GAA TCT GCA CGT CTT AGA GTC CAC TGA GTC CTT GCA CTC ACC ACA TCA CCT GGT GAA ACA GTC ACA CTC ACT
Ala Val Val Thr Gln Glu Ser Ala Arg Leu Arg Val His Ser Pro Gly Glu Thr Val Thr Leu Thr
└─FR1─────────────────────────────────────────────────────────────────────────────────────────────────────

TGT CGC TCA AGT ATT GGG GCT GTT ACA CCC CGA TCA AAT TAT GCC AAC TGG GTC CAA GAA AAA
ACA GCG AGT TCA TAA CCC GCA GGG GCT GTT ACA TGT TGA TCA TTG ATA CGG TTG ACC CAG GTT CTT TTT
Cys Arg Ser Ser Ile Gly Ala Val Thr Thr Ser Asn Tyr Ala Asn Trp Val Gln Glu Lys
│CDR1──────────────────────│                                         │FR2─────────────

CCA GAT CAT TTA TTC ACT GGT CTA ATA GGT ACC AAT AAC CGG GCT CCG GGT GTT CCT
GGT CTA GTA AAT AAG TGA CCA GAT TAT CCA TGG TTA TTG GCC CGA GGC CCA CAA GGA
Pro Asp His Leu Phe Thr Gly Leu Ile Gly Thr Asn Asn Arg Ala Pro Gly Val Pro
                                   │CDR2──────────│              │FR3

GCC AGA TTC TCA GGC TCC CTG ATT GGA GAC AAG GCT GCC CTC ACC ATC ACA GGG GCA CAG
CGG TCT AAG AGT CCG AGG GAC TAA CCT CTG TTC CGA CGG GAG TGG TAG TGT CCC CGT GTC
Ala Arg Phe Ser Gly Ser Leu Ile Gly Asp Lys Ala Ala Leu Thr Ile Thr Gly Ala Gln
```

```
ACT GAA GAT GAG GCA AGA TAT TTC TGT GCT CTA TCG TAC TGC AAC CTC TGG GTG TTC GGT
TGA CTT CTA CTC CGT TCT ATA AAG ACA CGA GAT ACC ATG ACG TTG GAG ACC CAC AAG CCA
Thr Glu Asp Glu Ala Arg Tyr Phe Cys Ala Leu Ser Tyr Cys Asn Leu Trp Val Phe Gly
                                        └─── CDR3 ───┘                 └─ FR4

GGA GGA ACC AAA CTG ACT GTC CTA AGC CAG CCC AAG TCT TCG CCA TCA GTC ACC CTG TTT
CCT CCT TGG TTT GAC TGA CAG GAT TCG GTC GGG TTC AGA AGC GGT AGT CAG TGG GAC AAA
Gly Gly Thr Lys Leu Thr Val Leu Ser Gln Pro Lys Ser Ser Pro Ser Val Thr Leu Phe
                            TTT GAC TGA CAG GAT TCG
                                        └───── BsiWI
                                    CGTACGCTC

CCG CCC TCC TCT GAA GAG CTA AGC TTG GGA ATC GGA TTC CCG GG
GGC GGG AGG AGA CTT CTC GAT TCG AAC CCT TAG CCT AAG GGC CC
Pro Pro Ser Glu Glu Leu Ser Leu Gly Ile Gly Phe Pro Gly
└─ FR4                                              CH1
```

FIG. 3B.

AGATCTGAAGTGACGCTGGTGGAGTCTGGGGGAGACTCAGTGAAGCCTGGAGGGTC
CCTGAAACTCTCCTGTGCAGCCTCTGGATTCACTTTAAGTGGTGAAACCATGTCTTG
GGTTCGCCAGACTCCGGAGAAGAGGCTGGAGTGGGTOGCAACCACTCTTAGTGGTG
GTGGTTTCACCTTCTATTCAGCCAGTGTGAAGGGTCGTTTCACCATCTCCAGAGACA
ATGCCCAGAACAACCTCTATCTACAACTGAATAGTCTGAGGTCTGAGGACACGGCCT
TGTATTTCTGTGCAAGTCATCGGTTTGTTCACTGGGGCCACGGGACTCTGGTCACTG
TCTCTGCAGCCAAAACGAOACCCCATCGGTCTTCCCCCTGGCACCCTCCTCCAAGA
GCACCTCTGGGGGCACAGCGGCCCTGGGCTGCCTGGTCAAGGACTACTTCCCCGAAC
CGGTGACGGTGTCGTGGAACTCAGGCGCCCTGACCAGCGGCGTGCACACCTTCCCGG
CTGTCCTACAGTCCTCAAGACTCTACTTCCTCAGCAGCGTGGTGACCGTGCCCTTCA
ACAGCTTGGGCACCCAGACCTACATCTGCAACGTGAATCACAAGCCCAGCAACACC
AAGGTGGACAAGAAAGCAGAGCCCAAATCTTGTGACAAATCTAGAGGGCCCTTCGA
AGGTAAGCCTATCCCTAACCCTCTCCTCGGTCTCGATTCTACGCGTACCGGTCATCA
TCACCATCACCATTGA

FIG. 8.

AGATCTGCTGTTGTGACTCAGGAATCTGCACTCACCACATCACCTGGTGAAACAGTC
ACACTCACTTGTCGCTCAAGTATTGGGGCTGTTACAACTAGTAACTATGCCAACTGG
GTCCAAGAAAAACCAGATCATTTATTCACTGGTCTAATAGGTGGTACCAATAACCGG
GCTCCGGGTGTTCCTGCCAGATTCTCAGGCTCCCTGATTGGAGACAAGGCTGCCCTC
ACCATCACAGGGGCACAGACTGAAGATGAGGCAAGATATTTCTGTGCTCTATGGTA
CTCCTGCCTCTGGGTRTTCGGTGGAGGAACCAAACTGACTGTCCTAAGCCGWACKGT
GGCTGCACCATCTGTCTTCATCTTCCCGCCATCTGATGAGCAGTTGAAATCTGGAAC
TGCCTCTGTTGTGTGCCTGCTGAATAACTTCTATCCCAGAGAGGCCAAAGTACAGTG
GAAGGTGGATAACGCCCTCCAATCGGGTAACTCCCAGGAGAGTGTCACAGAGCAGG
ACAGCAAGGACAGCACCTACAGCCTCAGCAGCACCCTGACGCTGAGCAAAGCAGAC
TACGAGAAACACAAAGTCTACGCCTGCGAAGTCACCCATCAGGGCCTGAGYTYGCC
CGTCACAAAGAGCTTCAACAGGGGAGAGTGTTAA

FIG. 9.

```
AGATCTGCTGTTGTGACTCAGGAATCTGCACTCACCACATCACCTGGTGAAACAGTC
ACACTCACTTGTCGCTCAAGTATTGGGGCTGTTACAACTAGTAACTATGCCAACTGG
GTCCAAGAAAAACCAGATCATTTATTCACTGGTCTAATAGGTGGTACCAATAACCGG
GCTCCGGGTGTTCCTGCCAGATTCTCAGGCTCCCTGATTGGAGACAAGGCTGCCCTC
ACCATCACAGGGGCACAGACTGAAGATGAGGCAAGATATTTCTGTGCTCTATGGTA
CTCCAACCTCTGGGTGTTCGGTGGAGGAACCAAACTGACTGTCCTAAGCCAGCCCA
AGTCTTCGCCATCAGTCACCCTGTTTCCGCCCTCCTCTGAAGAGCTAAGCTTGGGAA
TCGGATTGCCGGGGTGCCTGCTGAATAACTTCTATCCCAGAGAGGCCAAAGTACAGT
GGAAGGTGGATAACGCCCTCCAATCGGGTAACTCCCAGGAGAGTGTCACAGAGCAG
GACAGCAAGGACAGCACCTACAGCCTCAGCAGCACCCTGACGCTGAGCAAAGCAGA
CTACGAGAAACACAAAGTCTACGCCTGCGAAGTCACCCATCAGGGCCTGAGYTYGC
CCGTCACAAAGAGCTTCAACAGGGGAGAGTGTTAA
```

FIG. 10.

```
AGATCTGCTGTTGTGACTCAGGAATCTGCACTCACCACATCACCTGGTGAAACAGTC
ACACTCACTTGTCGCTCAAGTATTGGGGCTGTTACAACTAGTAACTATGCCAACTGG
GTCCAAGAAAAACCAGATCATTTATTCACTGGTCTAATAGGTGGTACCAATAACCGG
GCTCCGGGTGTTCCTGCCAGATTCTCAGGCTCCCTGATTGGAGACAAGGCTGCCCTC
ACCATCACAGGGGCACAGACTGAAGATGAGGCAAGATATTTCTGTGCTCTATGGTA
CTCCAACCTCTGGGTGTTCGGTGGAGGAACCAAACTGACTGTCCTAAGCCAGCCCA
AGTCTTCGCCATCAGTCACCCTGTTTCCGCCCTCCTCTGAAGAGCTAAGCTTGGGAA
TCGGATTCCCGGGGTGCCTGCTGAATAACTTCTATCCCAGAGAGGCCAAAGTACAGT
GGAAGGTGGATAACGCCCTCCAATCGGGTAACTCCCAGGAGAGTGTCACAGAGCAG
GACAGCAAGGACAGCACCTACAGCCTCAGCAGCACCCTGACGCTGAGCAAAGCAGA
CTACGAGAAACACAAAGTCTACGCCTGCGAAGTCACCCATCAGGGCCTGAGYTYGC
CCGTCACAAAGAGCTTCAACAGGGGAGAGTGTTAA
```

FIG. 11.

```
RSAVVTQESALTTSPGETVTLTCRSSIGAVTTSNYANWVQEKPDHLFTGLIGGTNNR
APGVPARFSGSLIGDKAALTITGAQTEDEARYFCALWYSCLWVFGGGTKLTVLSRTV
AAPSVFIFPPSDEQLKSGTASVVCLLNNFYPREAKVQWKVDNALQSGNSQESVTEQD
SKDSTYSLSSTLTLSKADYEKHKVYACEVTHQGLSXPVTKSFNRGEC
```

FIG. 12.

RSAVVTQESALTTSPGETVTLTCRSSIGAVTTSNYANWVQEKPDHLFTGLIGGTNNR
APGVPARFSGSLIGDKAALTITGAQTEDEARYFCALWYSNLWVFGGGTKLTVLSRTV
AAPSVFIFPPSDEQLKSGTASVVCLLNNFYPREAKVQWKVDNALQSGNSQESVTEQD
SKDSTYSLSSTLTLSKADYEKHKVYACEVTHQGLSXPVTKSFNRGEC

FIG. 13.

RSAVVTQESALTTSPGETVTLTCRSSIGAVTTSNYANWVQEKPDHLFTGLIGGTNNR
APGVPARFSGSLIGDKAALTITGAQTEDEARYFCALWYCNLWVFGGGTKLTVLSRTV
AAPSVFIFPPSDEQLKSGTASVVCLLNNFYPREAKVQWKVDNALQSGNSQESVTEQD
SKDSTYSLSSTLTLSKADYEKHKVYACEVTHQGLSXPVTKSFNRGEC

FIG. 14.

RSEVTLVEGRGDSVKPGGSLKLSCAASGFTLSGETMSWVRQTPEKRLEWVATTLSGG
GFTFYSASVKGRFTISRDN
AQNNLYLQLNSLRSEDTALYFCASHRFVHWGHGTLVTVSAAKTTPPSVFPLAPSSKS
TSGGTAALGCLVKDYFPEP
VTVSWNSGALTSGVHTFPAVLQSSRLYFLSSVVTVPFNSLGTQTYICNVNHKPSNTK
VDKKAEPKSCDKSRGPFEG
KPIPNPLLGLDSTRTGHHHHHH

FIG. 15.

ENGINEERING ANTIBODIES THAT BIND IRREVERSIBLY

CROSS-REFERENCES TO RELATED APPLICATIONS

The present application claims priority from U.S. Provisional Patent Application Ser. No. 60/156,194, titled "Engineering Antibodies that Bind Irreversibly," filed on Sep. 27, 1999, and U.S. Provisional Patent Application Ser. No. 60/208,684, titled "Engineering Antibodies that Bind Irreversibly to Target," filed on May 31, 2000, the disclosures of each of which are incorporated herein by reference in their entirety for all purposes.

STATEMENT AS TO RIGHTS TO INVENTIONS MADE UNDER FEDERALLY SPONSORED RESEARCH AND DEVELOPMENT

The work disclosed herein was at least partially supported by NIH Research Grant CA16861 to C. F. Meares. The Government may have rights in this invention.

BACKGROUND OF THE INVENTION

Over a million new cases of cancer will be diagnosed this year in the United States. While surgery can often provide definitive treatment of cancer in its early stages, the eradication of metastases is crucial to the cure of more advanced disease, Chemotherapeutic drugs are used in combinations for this purpose, with considerable success. Nonetheless, over half a million Americans will die from cancer this year. Progressions and relapses following surgery and chemotherapy/radiation are not uncommon, and in most cases the second line of treatment is of limited use. Despite the expenditure of large amounts of public and private resources over many years, better treatments for cancer are sorely needed.

Currently there are approximately 100 antineoplastic drugs on the market. Their systemic use is associated with undesirable side effects including toxicity to normal cells, which limits the doses used for treatment of the disease. Most pharmaceuticals consist of small organic molecules, which effectively traverse cell membranes and become widely distributed through the body. As reviewed by Langer, polymer-based pharmaceutical agents provide a variety of new approaches to safer and better therapies (see, Langer R, *Nature*, 392 (6679) SUPPS: 5–10 (1998)). Polymers and other macromolecules do not traverse membranes; however, they may be selectively accumulated in the interstitial space of a tumor, since tumors typically do not possess an efficient lymphatic drainage system (Yuan et al., *Cancer Research* 51(12): 3119–30 (1991)). Developing technology to target therapeutic drugs to cancer cells, while sparing normal cells, is a promising approach to improved treatment; visualizing small cancers by means of targeting reagents is already a productive area of investigation.

The residence of macromolecules in tumors may be prolonged if they become anchored to immobile elements, such as polymorphic epithelial mucin (PEM), the secreted product of the MUC1 gene (Taylor-Papadimitriou et al., *Trends Biotechnol.*, 12(6): 227–33 (1994)); or HLA-DR, a long-lived cell surface protein (Rose et al., *Cancer Immunology Immunotherapy*, 43: 26–30 (1996). The reagents of choice for this anchoring reaction are monoclonal antibodies and their derivatives. Currently there is a good selection of such macromolecules that bind to highly expressed tumor antigens, and that do not bind significantly to normal cells. Examples include, HMFG1 (Nicholson et al., *Oncology Reports* 5: 223–226 (1998)); L6 (DeNardo et al., *Journal of Nuclear Medicine* 39: 842–849 (1998)); and Lym-1 (DeNardo et al., *Clinical Cancer Research*, 3: 71–79 (1997)). The latter three antibodies have been conjugated to metal chelates for radioimmunotherapy and studied extensively in recent years, and are in clinical trials at various stages.

Recent data indicate that immunoconjugates have efficacy comparable to conventional antineoplastic drugs, and work in synergy with them (see, for example, Nicholson et al., *Oncology Reports* 5: 223–226 (1998); and DeNardo et al., *Proceedings of the National Academy of Sciences USA* 94: 4000–4004 (1997)). The emerging success of metal radio-immunoconjugates for cancer detection and treatment owes much to the development of metal-binding molecules (bifunctional chelating agents) appropriate for use in vivo, and to the further development of linkers that reduce concentrations of the metal binding molecules in nontarget tissues (see, Sundberg et al., *Nature* 250: 587–588 (1974); Yeh et al., *Analytical Biochemistry* 100: 152–159 (1979); Moi et al., *Analytical Biochemistry* 148: 249–253 (1985); Moi et al., *Journal of the American Chemical Society* 110: 6266–6267 (1988); and Li et al., *Bioconjugate Chemistry* 4: 275–283 (1993).

An alternative view of the potential for use of antibodies in cancer diagnosis and therapy is that, rather than carrying a radionuclide to a tumor, they can carry a receptor. Antibodies with dual binding specificity have been prepared which can, e.g., cross-link tumor cells to cytokines such as tumor necrosis factor (Bruno et al., *Cancer Res.* 56(20): 4758–4765 (1996)). Likewise, bispecific antibodies that can bind to tumors and to metal chelates have been developed (Stickney et al., *Cancer Res.* 51(24): 6650–5 (1991); Rouvier et al., *Horm. Res.* 47(4–6): 163–167 (1997)). When pretargeted to tumors, these bispecific antibodies bind to antigens and remain on the target, providing receptors for metal chelates. Subsequent administration of small, hydrophilic metal chelates leads to their capture by the targeted chelate receptors. Uncaptured chelates clear quickly through the kidneys and out of the body, leaving very little radioactivity in normal tissues. This strategy is known as "pretargeting."

A triumph of this approach was the imaging of metastatic cancer in the liver by an indium-111 chelate (Stickney et al., *Cancer Res.* B(24): 6650–5 (1991)). Antibodies conventionally conjugated to metal chelates are catabolized in the liver, and generally produce a radioactive background that masks tumors in that organ. The excellent tumor-to-background uptake ratios achieved by the pretargeting approach have led to considerable exploration of improvements in methodology. The anti-chelate antibody CHA255, initially developed for this purpose, possesses a high binding constant for (S)-benzyl-EDTA-indium chelates ($K_s \approx 4 \times 10^9$) and exquisite specificity for these haptens (Dayton et al., *Nature* 316: 265–268 (1985). On CHA255, the bound lifetimes of various indium chelates at 37° C. were found to be in the 10–40 min range (Meyer, et al, *Bioconjugate Chem.* 1(4): 278–84 (1990)). While this is (barely) long enough to obtain good images, it is inconveniently short relative to other physiological time scales for the biodistribution of the chelate (Yuan et al., *Cancer Research* 51(12): 3119–30 (1991)). In contrast, the multivalent binding of antibody IgG molecules to cell surfaces can lead to bound lifetimes of several days (Goodwin et al., *Cancer* 80, supps: 2675–2680 (1997)), and modem bifunctional chelating agents hold their metals for even longer periods. An important remaining challenge is to increase the antibody-hapten bound lifetime. Bivalent haptens provide an improvement but more is needed (Goodwin et al., *Journal of Nuclear Medicine,* 33: 2006–2013 (1992); and Rouvier et al., *Horm. Res.* B(4–6): 163–167 (1997)).

The need to enhance the antibody-hapten bound lifetime has led to the use of the long-lived avidin-biotin interaction, employing biotinylated metal chelates (Chinol et al., *Nuclear Medicine Communications* 18: 176–182 (1997)) in place of the original antibody-hapten interaction between CHA255 and benzyl-EDTA-indium derivatives. Here one assembles an antibody-avidin-chelate complex at the target in two or three steps, by sequential administration of non-radiolabeled proteins with a final administration of a biotinyl chelate carrying a radiometal. The extremely high affinity biotin-avidin association is adequately long-lived even for therapeutic applications (Theodore L J. et al, WO 9515979). Hen egg avidin and bacterial streptavidin, however, are both nonhuman, tetrameric proteins: their immunogenic properties are inconvenient, and the reversible associations between their subunits may limit their effectiveness. Thus, an improved strategy is still needed.

A delivery strategy based on the formation of a covalent bond between a chelate and an antibody that specifically recognizes and binds the chelate would represent a significant improvement over the methods now in use. The present invention provides engineered antibodies and chelates that react with one another to form covalent bonds and methods of using the engineered constructs to perform analyses and treat diseases.

SUMMARY OF THE INVENTION

An object of the present invention is the engineering of metal chelates that form covalent bonds with antibodies having affinity for the chelates. A further object of the invention is the design and preparation of antichelate antibodies bearing groups that react with the pendant functional group of the chelate. The covalent bond between the chelate and the antibody prevents the rapid dissociation of the chelate-antibody complex and greatly improves the in vivo residence times of the chelate. As discussed in the Background section, the preparation and characterization of metal chelates in which the chelating ligands bear a pendant reactive functional group is established in the art. By varying the pendant reactive functional group present on a chelate it is possible to prepare a library of chelates that includes functional groups exhibiting a range of reactivities. Moreover, a large array of bifunctional chelates having a range of thermodynamic and kinetic stabilities are known in the art. Thus, it is well within the abilities of those of skill in the art to design a reactive chelate having both a desired level of reactivity and stability.

Furthermore, it is straightforward to raise an antibody against essentially any chelate. Additionally, using modern molecular biology techniques, it is within the ability of those of skill in the art to mutagenize an antibody raised against a chelate and, thus, to engineer an antibody that includes a reactive site. The reactive site will generally be placed at a location proximate to the pendant reactive functional group of the chelate, such that when the antibody-antigen (chelate) complex is formed, the reactive functional group of the chelate and the reactive site of the antibody react readily to form a covalent bond, thereby linking the antibody and the chelate. The reactive site is complementary in reactivity to the reactive functional group of the chelate, and is selected from known reactive organic functionalities. The reactive site is preferably derived from a naturally- or non-naturally-occurring amino acid and is located at a position in the antibody structure that is proximate to or within the complimentarity-determining region ("CDR"). The only practical limitation on the location of the reactive site is that it must be positioned so that it can form a covalent bond with the pendant reactive functional group of the chelate.

The invention also provides chelate-antibody pairs. The chelate-antibody pairs of the invention are useful as analytical agents and in clinical diagnosis and therapy. When the chelate-antibody pairs are used as clinical therapeutic or diagnostic agents, the chelate circulates throughout the body of the patient to whom it is administered prior to reaching the targeting antibody, which has been pretargeted to a tissue or other site. To assure that a useful quantity of an administered dose of the chelate reaches the target antibody, the reactive group of the chelate is selected such that it does not react substantially with elements of blood and plasma for example but readily reacts with the complementary reactive site on the antibody following the formation of an antibody-antigen (chelate) complex.

Thus, in a first aspect, the present invention provides a mutant antibody comprising a reactive site that is not present in the wild-type of the antibody. The antibody also has a CDR that specifically binds to a metal chelate against which the wild-type antibody is raised. The reactive site of the mutant antibody is in a position proximate to or within the CDR, such that the chelate and the antibody are able to form a covalent bond.

For purposes of illustration, the invention is described further by reference to an exemplary antibody-chelate pair. The description is for clarity of illustration, and is not intended to define or limit the scope of the present invention.

In an exemplary embodiment, a reactive site is incorporated into an anti-chelate antibody by engineering a cysteine at one of several locations that are near to the region of the antibody to which the chelate binds. The engineering is typically accomplished by site-directed mutagenesis of a nucleic acid encoding the wild-type of the anti-chelate antibody. The resulting mutant antibodies comprise a library of single-Cys mutants. Mutated antibodies, such as the single-Cys mutants can be prepared using methods that are now routine in the art (see, for example, Owens et al., *Proceedings of the National Academy of Sciences USA* 95: 6021–6026 (1998); Owens et al., Biochemistry 37: 7670–7675 (1998)). The library members are then tested against a library of electrophilic chelates, differing in structure and reactivity, to determine the best pairs for further study. As discussed above, the electrophilic chelates preferably do not react prematurely with nucleophiles normally present in the blood. The reactivity of the chelates with physiologically relevant groups is easily determined in vitro. In the present example, in which the nucleophile is the cysteine —SH group, important potentially interfering groups are, for example, thiols on glutathione and other small molecules, and cysteine in albumin (Geigy Scientific Tables Vol. 3, C. Lentner, ed., Ciba-Geigy Ltd., Basel, Switzerland 1984). The mildly electrophilic groups on alkylating agents used in cancer chemotherapy (nitrogen mustards, ethyleneimine derivatives, mesylate esters, etc.) provide guidance concerning the practical limits of reactivity.

In a second aspect, the present invention provides a mutant antibody comprising a reactive cysteine residue that is not present in the wild-type of the antibody. The antibody also includes a CDR that specifically binds to a metal chelate against which the antibody is raised. The reactive —SH of the cysteine is in a position proximate to or within the CDR, such that the —SH group and the pendant reactive group on the antibody are able to form a covalent bond.

Because of the high local concentrations of nucleophile and electrophile in the antibody-hapten (chelate) complex, weaker electrophiles than those found on anticancer drugs are preferred. As discussed by Fersht, the effect of local concentration can be appreciated by comparing rate constants for the same chemical reaction between two separate reactants, and between two reactive groups joined by a linker (Alan Fersht, ENZYME STRUCTURE AND MECHANISM, 2nd Ed., Freeman, New York, 1985, pp. 56–63). The effect of high local concentration is displayed schematically in Scheme 1:

Scheme 1

in which effective local concentration of A in the presence of B in the unimolecular reaction=$k_1/k_2$.

Fersht cites examples where the effective local concentration defined in this way is enormous (e.g., >$10^5$ M). The enormous effective local concentrations lead to the insight that a hapten bearing a weakly reactive electrophile can diffuse intact through a dilute solution of nucleophiles, and still bind to the antibody CDR and undergo attack by a nucleophilic sidechain of the antibody.

In addition to the antibodies and antibody-chelate pairs of the invention, in a third aspect, there is also provided a method of using the compositions of the invention to treat a patient for a disease or condition or to diagnose the disease or condition. The method comprises the steps of: (a) administering to the patient a mutant antibody comprising; (i) a complementarity-determining region that specifically binds to the metal chelate; (ii) a reactive site not present in the wild-type of the antibody and, wherein the reactive site is in a position proximate to or within the complementarity-determining region; and (iii) a targeting moiety that binds specifically to a cell thereby forming a complex between the mutant antibody and the cell. The binding of the antibody to the cell can be mediated by any cell surface structure, for example, cell surface receptors and cell surface antigens. Following step (a), the metal chelate is administered to the patient. The metal chelate comprises a pendant reactive functional group having a reactivity complementary to the reactivity of the reactive site of the antibody. Thus, the chelate and the antibody bind to form an antibody-antigen (chelate) pair, the reactive groups of which subsequently react to form a covalent bond between the antibody and the antigen.

In addition to the method described above, the present invention also provides a method in which the tissue is pretargeted with an intermediate targeting reagent. The targeting moiety on the antibody of the invention subsequently recognizes and binds to the targeting reagent. In this aspect, the method comprises the steps of: (a) administering a targeting reagent to the patient; (b) following step (a), administering to the patient a mutant antibody of the invention. The mutant antibody comprises: (i) a complementarity-determining region that specifically binds to the metal chelate; (ii) a reactive site not present in the wild-type of the antibody (the reactive site is in a position proximate to or within the complementarity-determining region); and (iii) a targeting moiety that binds specifically with the targeting reagent, thereby forming a complex between the pretargeting reagent and the mutant antibody. After the pretargeting reagent has localized in the desired tissue, following step (b), a metal chelate is administered to the patient. The chelate specifically binds to the antibody forming an antibody-antigen complex. Moreover, the chelate comprises a reactive functional group having a reactivity complementary to that of the antibody reactive site. After the antibody-antigen complex is formed, the reactive site of the antibody and that of the metal chelate react to form a covalent bond between the mutant antibody and the metal chelate.

The compositions and methods of the present invention are described in greater detail below.

BRIEF DESCRIPTION OF THE DRAWINGS

FIG. 3 is the $V_L$ sequence of CHA255 mutant S95C. $V_L$ regions are marked. Cloning primers for SstI/BsiWI are shown.

FIG. 8 is SEQ. ID NO.: 1, which corresponds to a nucleic acid that encodes the Fab heavy chain of CHA255.

FIG. 9 is SEQ. ID NO.: 2, which encodes the light-chain mutant with C substituted for N at position 96 of CHA 255.

FIG. 10 is SEQ ID NO.: 3, which encodes the unmodified light chain of CHA255.

FIG. 11 is SEQ. ID NO.: 4, which encodes the light-chain mutant with C substituted for S at position 95 of CHA255.

FIG. 12 is SEQ. ID NO.: 5, which is the polypeptide sequence of a mutant light-chain of CHA255 with C substituted for N at position 96.

FIG. 13 is SEQ. ID NO.: 6, which is the polypeptide sequence of the unmodified light-chain of CHA255.

FIG. 14 is SEQ. ID NO.: 7, which is the polypeptide sequence of a light-chain mutant with C substituted for S at position 95 of CHA255.

FIG. 15 is SEQ. ID NO.: 8, which is the polypeptide sequence of the unmodified heavy-chain of CHA255.

Abbreviations

Figure 1:
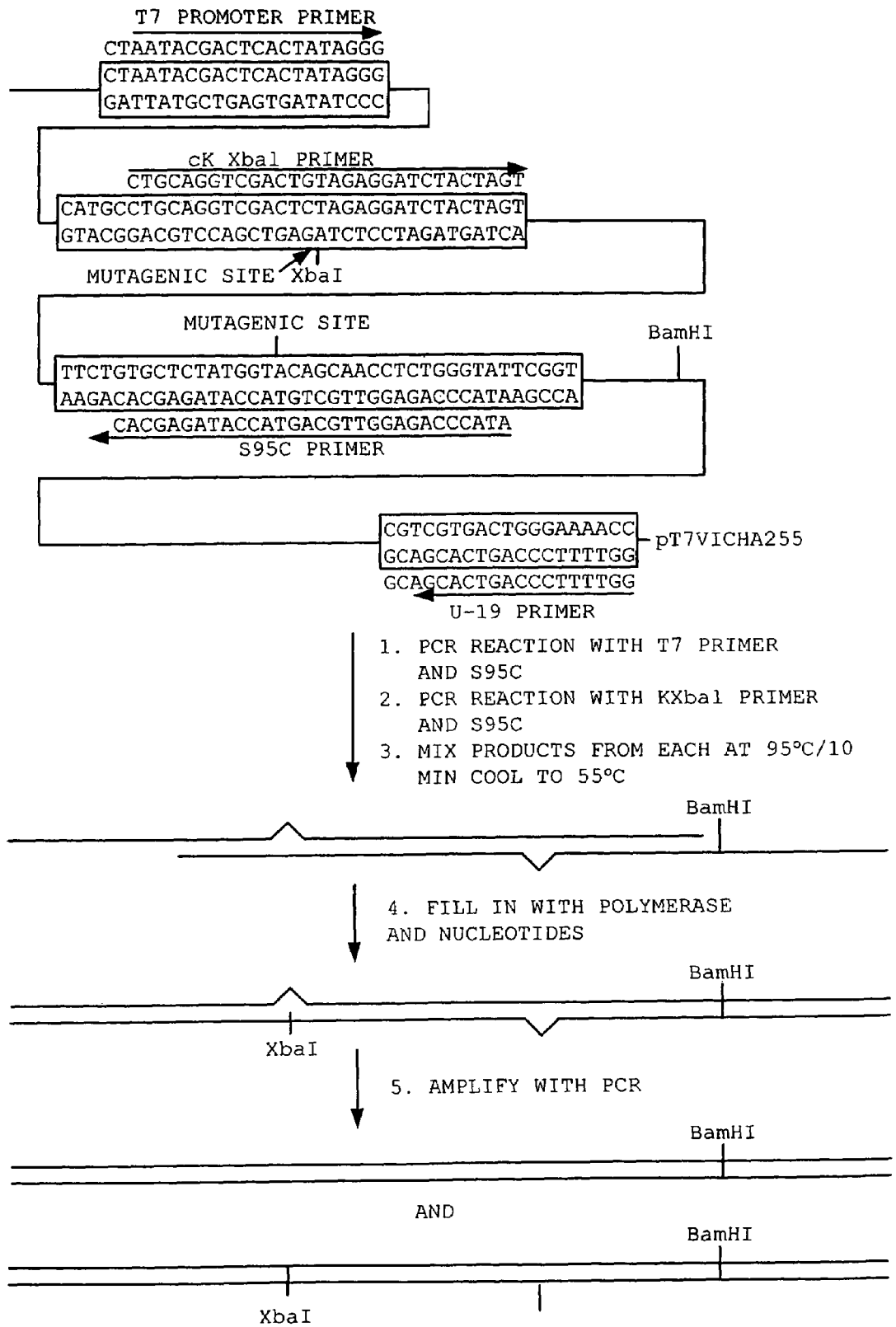
FIG. 1 is a flow diagram for the site-directed mutagenesis of Ser95 to Cys95 of the light chain of CHA255.

"CDR," as used herein refers to the "complementarity-determining region" of an antibody.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described below are those well known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein, the laboratory procedures in analytical chemistry, and the organic synthetic described below are those well known and commonly employed in the art. Standard techniques, or modifications thereof, are used for chemical syntheses and chemical analyses.

As used herein, "nucleic acid" means DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, and fluxionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodouracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications such as capping with a BHQ, a fluorophore or another moiety.

"Peptide" refers to a polymer in which the monomers are amino acids and are joined together through amide bonds, alternatively referred to as a polypeptide. When the amino acids are a-amino acids, either the L-optical isomer or the D-optical isomer can be used. Additionally, unnatural amino acids, for example, β-alanine, phenylglycine and homoarginine are also included. Amino acids that are not gene-encoded may also be used in the present invention. Furthermore, amino acids that have been modified to include reactive groups may also be used in the invention. All of the amino acids used in the present invention may be either the D- or L-isomer. The L-isomers are generally preferred. In addition, other peptidomimetics are also useful in the present invention. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. "Amino acid analogs" refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino "acid mimetic" refers to chemical compounds that have a structure that is different from the general chemical structure of an amino acid, but that functions in a manner similar to a naturally occurring amino acid.

"Antibody," as used herein, generally refers to a polypeptide comprising a framework region from an immunoglobulin or fragments thereof that specifically binds and recognizes an antigen. The recognized immunoglobulins include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

As used herein, "fragment" is defined as at least a portion of the variable region of the immunoglobulin molecule, which binds to its target, i.e., the antigen binding region. Some of the constant region of the immunoglobulin may be included.

As used herein, an "immunoconjugate" means any molecule or ligand such as an antibody or growth factor (i.e., hormone) chemically or biologically linked to a cytotoxin, a radioactive agent, an anti-tumor drug or a therapeutic agent. The antibody or growth factor may be linked to the cytotoxin, radioactive agent, anti-tumor drug or therapeutic agent at any location along the molecule so long as the antiobody is able to bind its target. Examples of immunoconjugates include immunotoxins and antibody conjugates.

As used herein, "selectively killing" means killing those cells to which the antibody binds.

As used herein, examples of "carcinomas" include bladder, breast, colon, liver, lung, ovarian, and pancreatic carcinomas.

As used herein, an "effective amount" is an amount of the antibody, immunoconjugate, which selectively kills cells or selectively inhibits the proliferation thereof.

As used herein, "complementarity-determining region" means that part of the antibody, recombinant molecule, fusion protein, or the immunoconjugate of the invention which recognizes the target or portions thereof.

As used herein, "therapeutic agent" means any agent useful for therapy including anti-tumor drugs, cytotoxins, cytotoxin agents, and radioactive agents.

As used herein, "anti-tumor drug" means any agent useful to combat cancer including, but not limited to, cytotoxins and agents such as antimetabolites, alkylating agents, anthracyclines, antibiotics, antimitotic agents, procarbazine, hydroxyurea, asparaginase, corticosteroids, mytotane (O,P'-(DDD)), interferons and radioactive agents.

As used herein, "a cytotoxin or cytotoxic agent" means any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

As used herein, "a radioactive agent" includes any radioisotope which is effective in destroying a tumor. Examples include, but are not limited to, indium-111, cobalt-60 and X-rays. Additionally, naturally occurring radioactive elements such as uranium, radium, and thorium which typically represent mixtures of radioisotopes, are suitable examples of a radioactive agent.

As used herein, "administering" means oral administration, administration as a suppository, topical contact, intravenous, intraperitoneal, intramuscular, intralesional or subcutaneous administration, or the implantation of a slow-release device e.g., a miniosmotic pump, to the subject.

As used herein, "cell surface antigens" means any cell surface antigen which is generally associated with cells involved in a pathology (e.g., tumor cells), i.e., occurring to a greater extent as compared with normal cells. Such antigens may be tumor specific. Alternatively, such antigens may be found on the cell surface of both tumorigenic and non-tumorigenic cells. These antigens need not be tumor specific. However, they are generally more frequently associated with tumor cells than they are associated with normal cells.

As used herein, "tumor targeted antibody" means any antibody which recognizes cell surface antigens on tumor (i.e., cancer) cells. Although such antibodies need not be tumor specific, they are tumor selective, i.e., bind tumor cells more than they do normal cells.

As used herein, "pharmaceutically acceptable carrier" includes any material which when combined with the antibody retains the antibody's immunogenicity and non-reactive with the subject's immune system. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules. Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods.

DETAILED DESCRIPTION OF THE INVENTION AND THE PREFERRED EMBODIMENTS

The present invention provides compositions for delivering therapeutic and diagnostic agents directly to cells involved in a disease or other pathology. The compositions of the invention include reactive therapeutic or diagnostic species and reactive antibodies that specifically bind the therapeutic or diagnostic species and, subsequent to the specific binding event, form a covalent bond via the reactive site of the antibody and the pendant reactive functional group of the therapeutic or diagnostic species. Also provided are methods of treating a patient using the compounds described herein.

The present invention is illustrated by reference to the use of reactive metal chelates as an exemplary embodiment. The use of metal chelates to illustrate the concept of the invention is not intended to define or limit the scope of the invention. Those of skill in the art will readily appreciate that the concepts underlying the compositions and methods described herein are equally applicable to any therapeutic or diagnostic agent to which an antibody can be raised (e.g., antitumor drugs, cytotoxins, etc.).

A. The Compositions

In a first aspect, the present invention provides a mutant antibody comprising a reactive site that is not present in the wild-type of the antibody. The antibody also has a CDR that specifically binds to a metal chelate against which the wild-type antibody is raised. The reactive site of the mutant antibody is in a position proximate to or within the complementarity-determining region, such that the chelate and the antibody are able to form a covalent bond.

1. The Antibodies

The present invention provides reactive mutant antibodies that specifically bind to reactive metal chelates. An exemplary immunoglobulin (antibody) structural unit comprises a tetramer. Each tetramer is composed of two identical pairs of polypeptide chains, each pair having one "light" (about 25 kDa) and one "heavy" chain (about 50–70 kDa). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist, e.g., as intact immunoglobulins or as a number of well characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region, thereby converting the F(ab)'2 dimer into an Fab' monomer. The Fab' monomer is essentially an Fab with part of the hinge region (see, FUNDAMENTAL IMMUNOLOGY, Paul ed., $3^{rd}$ ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies or those synthesized de novo using recombinant DNA methodologies (e.g., single chain $F_v$).

For preparation of monoclonal or polyclonal antibodies, any technique known in the art can be used (see, e.g., Kohler & Milstein, *Nature* 256: 495–497 (1975); Kozbor et al., *Immunology Today* 4: 72 (1983); Cole et al., pp. 77–96 in MONOCLONAL ANTIBODIES AND CANCER THERAPY, Alan R. Liss, Inc. (1985)).

Methods of producing polyclonal antibodies are known to those of skill in the art. In an exemplary method, an inbred strain of mice (e.g., BALB/C mice) or rabbits is immunized with the chelate or a close structural analogue using a standard adjuvant, such as Freund's adjuvant, and a standard immunization protocol. Alternatively, or in addition to the use of an adjuvant, the chelate is coupled to a carrier that is itself immunogenic (e.g., keyhole limpit hemocyanin ("KLH"). The animal's immune response to the immunogen preparation is monitored by taking test bleeds and determining the titer of reactivity to the beta subunits. When appropriately high titers of antibody to the immunogen are obtained, blood is collected from the animal and antisera are prepared. Further fractionation of the antisera to enrich for antibodies reactive to the protein can be done if desired.

Monoclonal antibodies are obtained by various techniques familiar to those skilled in the art. Briefly, spleen cells from an animal immunized with a desired antigen are immortalized, commonly by fusion with a myeloma cell (see, for example, Kohler & Milstein, *Eur. J. Immunol.* 6: 511–519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., *Science* 246: 1275–1281 (1989).

Monoclonal antibodies and polyclonal sera are collected and titered against the immunogen in an immunoassay, for example, a solid phase immunoassay with the immunogen immobilized on a solid support. Typically, polyclonal antisera with a titer of 104 or greater are selected and tested for their cross reactivity against different chelates, using a competitive binding immunoassay. Specific polyclonal antisera and monoclonal antibodies will usually bind with a $K_d$ of at least about 0.1 mM, more usually at least about 1 µM, preferably at least about 0.1 µM or better, and most preferably, 0.01 µM or better.

Techniques for the production of single chain antibodies (U.S. Pat. No. 4,946,778) can be adapted to produce antibodies to reactive chelates and other diagnostic, analytical and therapeutic agents. Also, transgenic mice, or other organisms such as other mammals, may be used to express humanized antibodies. Alternatively, phage display technology can be used to produce and identify antibodies and heteromeric Fab fragments that specifically bind to selected antigens (see, e.g., McCafferty et al., *Nature* 348: 552–554 (1990); Marks et al., *Biotechnology* 10: 779–783 (1992)).

In an exemplary embodiment, an animal, such as a rabbit or mouse is immunized with a chelate, or an immunogenic construct. The antibodies produced as a result of the immunization are preferably isolated using standard methods.

In a still further preferred embodiment, the antibody is a humanized antibody. "Humanized" refers to a non-human polypeptide sequence that has been modified to minimize immunoreactivity in humans, typically by altering the amino acid sequence to mimic existing human sequences, without substantially altering the function of the polypeptide sequence (see, e.g., Jones et al., *Nature* 321: 522–525 (1986), and published UK patent application No. 8707252).

In another preferred embodiment, the present invention provides an antibody, as described above, further comprising a member selected from detectable labels, biologically active agents and combinations thereof attached to the antibody.

When the antibody is conjugated to a detectable label, the label is preferably a member selected from the group consisting of radioactive isotopes, fluorescent agents, fluorescent agent precursors, chromophores, enzymes and combinations thereof. Methods for conjugating various groups to antibodies are well known in the art. For example, a detectable label that is frequently conjugated to an antibody is an enzyme, such as horseradish peroxidase, alkaline phosphatase, β-galactosidase, and glucose oxidase.

In an exemplary embodiment of the present invention, horseradish peroxidase is conjugated to an antibody raised against a reactive chelate. In this embodiment, the saccharide portion of the horseradish peroxidase is oxidized by periodate and subsequently coupled to the desired immunoglobin via reductive amination of the oxidized saccharide hydroxyl groups with available amine groups on the immunoglobin.

Methods of producing antibodies labeled with small molecules, for example, fluorescent agents, are well known in the art. Fluorescent labeled antibodies can be used in immunohistochemical staining (Osborn et al., *Methods Cell Biol.* 24: 97–132 (1990); in flow cytometry or cell sorting techniques (Ormerod, M. G. (ed.), FLOW CYTOMETRY. A PRACTICAL APPROACH, IRL Press, New York, 1990); for tracking and localization of antigens, and in various double-staining methods (Kawamura, A., Jr., FLUORESCENT ANTIBODY TECHNIQUES AND THEIR APPLICATION, Univ. Tokyo Press, Baltimore, 1977).

Many reactive fluorescent labels are available commercially (e.g., Molecular Probes, Eugene, Oreg.) or they can be synthesized using art-recognized techniques. In an exemplary embodiment, an antibody of the invention is labeled with an amine-reactive fluorescent agent, such as fluorescein isothiocyanate under mildly basic conditions. For other examples of antibody labeling techniques, see, Goding, *J. Immunol. Methods* 13: 215–226 (1976); and in, MONOCLONAL ANTIBODIES: PRINCIPLES AND PRACTICE, pp. 6–58, Academic Press, Orlando (1988).

Prior to constructing the mutagenized antibodies of the invention, it is often useful to prepare the wild-type antichelate antibody from an isolated nucleic acid encoding an antibody or a portion of an antibody of the invention. In a further preferred embodiment, the antibody fragment is an $F_v$ fragment. $F_v$ fragments of antibodies are heterodimers of antibody $V_H$ (variable region of the heavy chain) and $V_L$ domains (variable region of the light chain). They are the smallest antibody fragments that contain all structural information necessary for specific antigen binding. $F_v$ fragments are useful for diagnostic and therapeutic applications such as imaging of tumors or targeted cancer therapy. In particular, because of their small size, $F_v$ fragments are useful in applications that require good tissue or tumor penetration, because small molecules penetrate tissues much faster than large molecules (Yokota et al., *Cancer Res.*, 52: 3402–3408 (1992)).

The heterodimers of heavy and light chain domains that occur in whole IgG, for example, are connected by a disulfide bond, but $F_v$ fragments lack this connection. Although native unstabilized $F_v$ heterodimers have been produced from unusual antibodies (Skerra et al., *Science*, 240: 1038–1041 (1988); Webber et al., *Mol. Immunol.* 4: 249–258 (1995), generally $F_v$ fragments by themselves are unstable because the $V_H$ and $V_L$ domains of the heterodimer can dissociate (Glockshuber et al., *Biochemistry* 29: 1362–1367 (1990)). This potential dissociation results in drastically reduced binding affinity and is often accompanied by aggregation.

Solutions to the stabilization problem have resulted from a combination of genetic engineering and recombinant protein expression techniques. Such techniques are of use in constructing the antibodies of the present invention. The most common method of stabilizing $F_v$s is the covalent connection of $V_H$ and $V_L$ by a flexible peptide linker, which results in single chain $F_v$ molecules (see, Bird et al., *Science*

242: 423–426 (1988); Huston et al., *Proc. Natl. Acad. Sci. USA* 16: 5879–5883 (1988)). The single chain $F_v$s (sc$F_v$s) are generally more stable than $F_v$s alone.

Another way to generate stable recombinant $F_v$s is to connect $V_H$ and $V_L$ by an interdomain disulfide bond instead of a linker peptide; this technique results in disulfide stabilized $F_v$ (ds$F_v$). The ds$F_v$s solve many problems that can be associated with sc$F_v$s: they are very stable, often show full antigen binding activity, and sometimes have better affinity than sc$F_v$s (Reiter et al., *Int. Cancer* 58: 142–149 (1994)). Thus, in another preferred embodiment, the antibody of the invention is a sc$F_v$s.

Peptide linkers, such as those used in the expression of recombinant single chain antibodies, may be employed as the linkers and connectors of the invention. Peptide linkers and their use are well known in the art. (See, e.g., Huston et al., 1988; Bird et al., 1983; U.S. Pat. No. 4,946,778; U.S. Pat. No. 5,132,405; and Stemmer et al., *Biotechniques* 14:256–265 (1993)). The linkers and connectors are flexible and their sequence can vary. Preferably, the linkers and connectors are long enough to span the distance between the amino acids to be joined without putting strain on the structure. For example, the linker (gly$_4$ser)$_3$ is a useful linker because it is flexible and without a preferred structure (Freund et al., *Biochemistry* 33: 3296–3303 (1994)).

After the stabilized immunoglobin has been designed, a gene encoding at least $F_v$ or a fragment thereof is constructed. Methods for isolating and preparing recombinant nucleic acids are known to those skilled in the art (see, Sambrook et al., *Molecular Cloning. A Laboratory Manual* (2d ed. 1989); Ausubel et al., *Current Protocols in Molecular Biology* (1995)).

The present invention provides for the expression of nucleic acids corresponding to the wild-type of essentially any antibody that can be raised against a metal chelate, and the modification of that antibody to include a reactive site. In a preferred embodiment, the Fab heavy chain of the wild-type antibody is encoded by a nucleic acid having a structure according to SEQ. ID NO.: 1 (FIG. 8). In another preferred embodiment, the light-chain of the wild-type antibody is encoded by a nucleic acid according to SEQ. ID NO.: 3 (FIG. 10). In yet another preferred embodiment, the invention provides a mutant of the light chain of CHA255 that has the sequence set forth in SEQ. ID NO.: 2 (FIG. 9), in which N-96 is substituted by C. In yet another preferred embodiment, the invention provides a nucleic acid that encodes a mutant of the light-chain of CHA255 in which S-95 is replaced by C. The sequence of the C-95 mutant is set forth in SEQ. ID NO.: 4 (FIG. 11).

Those of skill in the art will understand that substituting selected codons from the above-recited sequences with equivalent codons is within the scope of the invention.

Oligonucleotides that are not commercially available are preferably chemically synthesized according to the solid phase phosphoramidite triester method first described by Beaucage & Caruthers, *Tetrahedron Letts.* 22: 1859–1862 (1981), using an automated synthesizer, as described in Van Devanter et. al., *Nucleic Acids Res.* 12: 6159–6168 (1984). Purification of oligonucleotides is preferably by either native acrylamide gel electrophoresis or by anion-exchange HPLC as described in Pearson & Reanier, *J. Chrom.* 255: 137–149 (1983).

The sequence of the cloned genes and synthetic oligonucleotides can be verified after cloning using art-recognized methods, e.g., the chain termination method for sequencing double-stranded templates of Wallace et al., *Gene* 16: 21–26 (1981).

One preferred method for obtaining specific nucleic acid sequences combines the use of synthetic oligonucleotide primers with polymerase extension or ligation on a mRNA or DNA template. Such a method, e.g., RT, PCR, or LCR, amplifies the desired nucleotide sequence, which is often known (see, U.S. Pat. Nos. 4,683,195 and 4,683,202). Restriction endonuclease sites can be incorporated into the primers. Amplified polynucleotides are purified and ligated into an appropriate vector. Alterations in the natural gene sequence can be introduced by techniques such as in vitro mutagenesis and PCR using primers that have been designed to incorporate appropriate mutations.

A particularly preferred method of constructing the immunoglobulin is by overlap extension PCR. In this technique, individual fragments are first generated by PCR using primers that are complementary to the immunoglobulin sequences of choice. These sequences are then joined in a specific order using a second set of primers that are complementary to "overlap" sequences in the first set of primers, thus linking the fragments in a specified order. Other suitable $F_v$ fragments can be identified by those skilled in the art.

The immunoglobulin, e.g., $F_v$, is inserted into an "expression vector," "cloning vector," or "vector." Expression vectors can replicate autonomously, or they can replicate by being inserted into the genome of the host cell. Often, it is desirable for a vector to be usable in more than one host cell, e.g., in *E. coli* for cloning and construction, and in a mammalian cell for expression. Additional elements of the vector can include, for example, selectable markers, e.g., tetracycline resistance or hygromycin resistance, which permit detection and/or selection of those cells transformed with the desired polynucleotide sequences (see, e.g., U.S. Pat. No. 4,704,362). The particular vector used to transport the genetic information into the cell is also not particularly critical. Any suitable vector used for expression of recombinant proteins host cells can be used.

Expression vectors typically have an expression cassette that contains all the elements required for the expression of the polynucleotide of choice in a host cell. A typical expression cassette contains a promoter operably linked to the polynucleotide sequence of choice. The promoter used to direct expression of the nucleic acid depends on the particular application, for example, the promoter may be a prokaryotic or eukaryotic promoter depending on the host cell of choice. The promoter is preferably positioned about the same distance from the heterologous transcription start site as it is from the transcription start site in its natural setting. As is known in the art, however, some variation in this distance can be accommodated without loss of promoter function.

Promoters include any promoter suitable for driving the expression of a heterologous gene in a host cell, including those typically used in standard expression cassettes. In addition to the promoter, the recombinant protein gene will be operably linked to appropriate expression control sequences for each host. For *E. coli* this includes a promoter such as the T7, trp, tac, lac or lambda promoters, a ribosome binding site, and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The vectors of the can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

The wild-type antichelate-antibodies can be expressed in a variety of host cells, including *E. coli*, other bacterial hosts, yeast, and various higher eukaryotic cells such as the COS, CHO, and HeLa cells lines and myeloma cell lines. Methods for refolding single chain polypeptides expressed in bacteria such as *E. coli* have been described, are well-known and are applicable to the wild-type anti-chelate polypeptides. (See, e.g., Buchner et al., *Analytical Biochemistry* 205: 263–270 (1992); Pluckthun, *Biotechnology* 9: 545 (1991); Huse et al., *Science* 246: 1275 (1989) and Ward et al., *Nature* 341: 544 (1989)).

In a preferred embodiment, the present invention provides a polypeptide that is essentially homologous to the $V_L$ sequence of CHA255, with the exception that serine-95 is replaced with a cysteine (FIG. 3).

Often, functional protein from *E. coli* or other bacteria is generated from inclusion bodies and requires the solubilization of the protein using strong denaturants, and subsequent refolding. In the solubilization step, a reducing agent must be present to dissolve disulfide bonds as is well-known in the art. Renaturation to an appropriate folded form is typically accomplished by dilution (e.g. 100-fold) of the denatured and reduced protein into refolding buffer.

Once expressed, the recombinant proteins can be purified according to standard procedures of the art, including ammonium sulfate precipitation, affinity columns, column chromatography, and the like (see, generally, Scopes, PROTEIN PURIFICATION (1982)). Substantially pure compositions of at least about 90 to 95% homogeneity are preferred, and 98 to 99% or more homogeneity are most preferred for pharmaceutical uses. Once purified, partially or to homogeneity as desired, the polypeptides may then be used therapeutically and diagnostically.

a. Bispecific Antibodies

In another preferred embodiment, the present invention provides for a reactive antibody that is bispecific for both a metal chelate and a targeting reagent or a target tissue, such as a tumor. Bispecific antibodies (BsAbs) are antibodies that have binding specificities for at least two different antigens. Bispecific antibodies can be derived from full length antibodies or antibody fragments (e.g. F(ab')$_2$ bispecific antibodies). In a preferred embodiment, the bispecific antibody recognizes a reactive $^{111}$In chelate of the invention and a human carcinoma cell.

Methods for making bispecific antibodies are known in the art. Traditional production of full-length bispecific antibodies is based on the co-expression of two immunoglobulin heavy chain-light chain pairs, where the two chains have different specificities (Millstein and Cuello, *Nature* 305: 537–539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, published May 13, 1993, and in Traunecker et al., *EMBO J.* 10: 3655–3659 (1991)).

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690 published Mar. 3, 1994. For further details of generating bispecific antibodies (see, for example, Suresh et al., *Methods in Enzymology* 121: 210 (1986)).

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al. (*Science* 229: 81 (1985)) describe a procedure wherein intact antibodies are proteolytically cleaved to generate F(ab')$_2$ fragments. The fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the BsAb. The BsAbs produced can be used as agents for the selective immobilization of enzymes.

Recent progress has facilitated the direct recovery of Fab'-SH fragments from *E. coli*, which can be chemically coupled to form bispecific antibodies. Shalaby et al., *J Ex. Med.*, B 217–225 (1992) describe the production of a fully humanized BsAb F(ab')$_2$ molecule. Each Fab' fragment was separately secreted from *E. coli* and subjected to directed chemical coupling in vitro to form the BsAb. The BsAb thus formed was able to bind to cells overexpressing the HER2 receptor and normal human T cells, as well as trigger the lytic activity of human cytotoxic lymphocytes against human breast tumor targets. See also, Rodrigues et al., *Int. J. Cancers*, (Suppl.) 7: 45–50 (1992).

Various techniques for making and isolating BsAb fragments directly from recombinant cell culture have also been described and are useful in practicing the present invention. For example, bispecific F(ab')$_2$ heterodimers have been produced using leucine zippers. Kostelny et al., *J. Immunol.*, 148(5): 1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. The "diabody" technology described by Hollinger et al., Proc. Natl. Acad. Sci. (USA), 90: 6444–6448 (1993) has provided an alternative mechanism for making BsAb fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making BsAb fragments by the use of single-chain Fv (sFv) dimers has also been reported (see, Gruber et al., *J. Immunol.*, 152: 5368 (1994)). Gruber et al., designed an antibody which comprised the $V_H$ and $V_L$ domains of a first antibody joined by a 25-amino-acid-residue linker to the $V_H$ and $V_L$ domains of a second antibody. The refolded molecule bound to fluorescein and the T-cell receptor and redirected the lysis of human tumor cells that had fluorescein covalently linked to their surface.

In addition to the preparation of wild-type antibodies that specifically bind to metal chelates, the present invention provides mutant antibodies that include a reactive site within their structure. The mutant antibodies are prepared by any method known in the art, most preferably by site directed mutagenesis of a nucleic acid encoding the wild-type antibody.

b. Site-Directed Mutagenesis

The preparation of wild-type antibodies that bind to metal chelates is discussed above. The elements of the discussion above are also broadly applicable to aspects and embodiments of the invention in which site directed mutagenesis is used to produce mutant antibodies. The concept of site-directed mutagenesis as it applies to the present invention is discussed in greater detail to supplement, not to replace the discussion above.

The mutant antibodies are suitably prepared by introducing appropriate nucleotide changes into the DNA encoding the polypeptide of interest, or by in vitro synthesis of the desired mutant antibody. Such mutants include, for example, deletions from, or insertions or substitutions of, residues within the amino acid sequence of the polypeptide of interest so that it contains the proper epitope and is able to form a covalent bond with a reactive metal chelate. Any combination of deletion, insertion, and substitution is made to arrive at the final construct, provided that the final construct possesses the desired characteristics. The amino acid changes also may alter post-translational processes of the polypeptide of interest, such as changing the number or position of glycosylation sites. Moreover, like most mammalian genes, the antibody can be encoded by multi-exon genes.

For the design of amino acid sequence mutants of the antibodies, the location of the mutation site and the nature of the mutation will be determined by the specific polypeptide of interest being modified and the structure of the reactive chelate to which the antibody binds. The sites for mutation can be modified individually or in series, e.g., by: (1) substituting first with conservative amino acid choices and then with more radical selections depending upon the results achieved; (2) deleting the target residue; or (3) inserting residues of the same or a different class adjacent to the located site, or combinations of options 1–3.

A useful method for identification of certain residues or regions of the polypeptide of interest that are preferred locations for mutagenesis is called "alanine scanning mutagenesis," as described by Cunningham and Wells, *Science*, 244: 1081–1085 (1989). Here, a residue or group of target residues is identified (e.g., charged residues such as arg, asp, his, lys, and glu) and replaced by a neutral or negatively charged amino acid (most preferably alanine or polyalanine) to affect the interaction of the amino acids with the surrounding aqueous environment in or outside the cell. Those domains demonstrating functional sensitivity to the substitutions then are refined by introducing further or other variants at or for the sites of substitution. Thus, while the site for introducing an amino acid sequence variation is predetermined, the nature of the mutation per se need not be predetermined. For example, to optimize the performance of a mutation at a given site, alanine scanning or random mutagenesis is conducted at the target codon or region and the variants produced are screened for increased reactivity with a particular reactive chelate.

Amino acid sequence deletions generally range from about 1 to 30 residues, more preferably about 1 to 10 residues, and typically they are contiguous. Contiguous deletions ordinarily are made in even numbers of residues, but single or odd numbers of deletions are within the scope hereof. As an example, deletions may be introduced into regions of low homology among LFA-1 antibodies, which share the most sequence identity to the amino acid sequence of the polypeptide of interest to modify the half-life of the polypeptide. Deletions from the polypeptide of interest in areas of substantial homology with one of the binding sites of other ligands will be more likely to modify the biological activity of the polypeptide of interest more significantly. The number of consecutive deletions will be selected so as to preserve the tertiary structure of the polypeptide of interest in the affected domain, e.g., beta-pleated sheet or alpha helix.

Amino acid sequence insertions include amino- and/or carboxyl-terminal fusions ranging in length from one residue to polypeptides containing a hundred or more residues, as well as intra-sequence insertions of single or multiple amino acid residues. Intra-sequence insertions (i.e., insertions within the mature polypeptide sequence) may range generally from about 1 to 10 residues, more preferably 1 to 5, most preferably 1 to 3. Insertions are preferably made in even numbers of residues, but this is not required. Examples of insertions include insertions to the internal portion of the polypeptide of interest, as well as N- or C-terminal fusions with proteins or peptides containing the desired epitope that will result, upon fusion, in an increased reactivity with the chelate.

A third group of variants are amino acid substitution variants. These variants have at least one amino acid residue in the polypeptide molecule removed and a different residue inserted in its place. The sites of greatest interest for substitutional mutagenesis include one or two loops in antibodies. Other sites of interest are those in which particular residues of the polypeptide obtained from various species are identical among all animal species; degree of conservation suggesting importance in achieving biological activity common to these molecules. These sites, especially those falling within a sequence of at least three other identically conserved sites, are substituted in a relatively conservative manner. Such conservative substitutions are shown in Table 1 under the heading of preferred substitutions. If such substitutions result in a change in biological activity, then more substantial changes, denominated exemplary substitutions in Table 1, or as further described below in reference to amino acid classes, are introduced and the products screened.

TABLE 1

| Original | Substitution |
| --- | --- |
| Ala (A) | val; leu; ile |
| Arg (R) | lys; gln; asn |
| Asn (N) | gln; his; lys |
| Asp (D) | glu |
| Cys (C) | ser |
| Gln (Q) | asn |
| Glu (E) | asp |
| Gly (G) | pro; ala |
| His (H) | asn; gln; lys; arg |
| Ile (I) | leu; vat; met; ala |
| Phe; | norleucine |
| Leu (L) | norleucine; ile; val; met; ala; phe |
| Lys (K) | arg; gln; asn |
| Met (M) | leu; phe; ile |
| Phe (F) | leu; val; ile; ala; leu |
| Pro (P) | ala |
| Ser (S) | thr |
| Thr (T) | ser |
| Trp (W) | tyr; phe |
| Tyr (Y) | trp; phe; thr; ser |
| Val (V) | ile; leu; met; phe; ala; norleucine |

In addition to the incorporation of the reactive site in the antibody structure, modifications in the function of the polypeptide of interest can be made by selecting substitutions that differ significantly in their effect on maintaining: (a) the structure of the polypeptide backbone in the area of the substitution, for example, as a sheet or helical conformation; (b) the charge or hydrophobicity of the molecule at the target site; or (c) the bulk of the side chain. Naturally occurring residues are divided into groups based on common side-chain properties:

(1) hydrophobic: norleucine, met, ala, val, leu, ile;

(2) neutral hydrophilic: cys, ser, thr;

(3) acidic: asp, glu;

(4) basic: asn, gln, his, lys, arg;

(5) residues that influence chain orientation: gly, pro; and (6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

It also may be desirable to inactivate one or more protease cleavage sites that are present in the molecule. These sites are identified by inspection of the encoded amino acid sequence, in the case of trypsin, e.g., for an arginyl or lysinyl residue. When protease cleavage sites are identified, they are rendered inactive to proteolytic cleavage by substituting the targeted residue with another residue, preferably a basic residue such as glutamine or a hydrophilic residue such as serine; by deleting the residue; or by inserting a prolyl residue immediately after the residue.

In another embodiment, any methionyl residues other than the starting methionyl residue of the signal sequence, or any residue located within about three residues N- or C-terminal to each such methionyl residue, is substituted by another residue (preferably in accord with Table 1) or deleted. Alternatively, about 1–3 residues are inserted adjacent to such sites.

The nucleic acid molecules encoding amino acid sequence mutations of the antibodies of interest are prepared by a variety of methods known in the art. These methods include, but are not limited to, preparation by oligonucleotide-mediated (or site-directed) mutagenesis, PCR mutagenesis, and cassette mutagenesis of an earlier prepared variant or a non-variant version of the polypeptide on which the variant herein is based.

Oligonucleotide-mediated mutagenesis is a preferred method for preparing substitution, deletion, and insertion antibody mutants herein. This technique is well known in the art as described by Adelman et al., *DNA* 2: 183 (1983). Briefly, the DNA is altered by hybridizing an oligonucleotide encoding the desired mutation to a DNA template, where the template is the single-stranded form of a plasmid or bacteriophage containing the unaltered or native DNA sequence of the polypeptide to be varied. After hybridization, a DNA polymerase is used to synthesize an entire second complementary strand of the template that will thus incorporate the oligonucleotide primer, and will code for the selected alteration in the DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al., *Proc. Natl. Acad. Sci. USA*, 75: 5765 (1978).

The DNA template can be generated by those vectors that are either derived from bacteriophage M13 vectors (e.g., the commercially available M13mp18 and M13mp19 vectors are suitable), or those vectors that contain a single-stranded phage origin of replication as described by Viera et al. *Meth. Enzymol.*, 153: 3 (1987). Thus, the DNA that is to be mutated may be inserted into one of these vectors to generate single-stranded template. Production of the single-stranded template is described in Sections 4.21–4.41 of Sambrook et al., supra. Alternatively, single-stranded DNA template is generated by denaturing double-stranded plasmid (or other) DNA using standard techniques.

For alteration of the original DNA sequence to generate the antibody variants of this invention, the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed, such that one strand of DNA encodes the mutated form of the polypeptide, and the other strand (the original template) encodes the original, unaltered sequence of the polypeptide. This heteroduplex molecule is then transformed into a suitable host cell, usually a prokaryote such as *E. coli* (e.g., JM101). After the cells are grown, they are plated onto agarose plates and screened by, for example, using the oligonucleotide primer radiolabeled with $^{32}$P to identify the bacterial colonies that contain the mutated DNA. The mutated region is then removed and placed in an appropriate vector for protein production, generally an expression vector of the type typically employed for transformation of an appropriate host.

The method described immediately above may be modified such that a homoduplex molecule is created wherein both strands of the plasmid contain the mutation(s). The modifications are as follows: the single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thio-deoxyribocytosine called dCTP-(S) (which can be obtained from the Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(αS) instead of dCTP, which serves to protect it from restriction endonuclease digestion.

After the template strand of the double-stranded heteroduplex is nicked with an appropriate restriction enzyme, the template strand can be digested with an appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as E. coli, as described above.

DNA encoding antibody mutants with more than one amino acid substituted are generated in one of several ways. If the amino acids are located close together in the polypeptide chain, they are mutated simultaneously using one oligonucleotide that codes for all of the desired amino acid substitutions. If, however, the amino acids are located some distance from each other (separated by more than about ten amino acids), it is more difficult to generate a single oligonucleotide that encodes all of the desired changes. Instead, one of two alternative methods are typically employed.

In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions.

In an alternative method, two or more rounds of mutagenesis are performed to produce the desired mutant. The first round is as described for the single mutants: wild-type DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. The resulting DNA is used as a template in a third round of mutagenesis, and so on.

PCR mutagenesis is also suitable for making the mutant antibodies of this invention. While the following discussion refers to DNA, it is understood that the technique also finds application with RNA. The PCR technique generally refers to the following procedure (see, Erlich, supra, the chapter by R. Higuchi, p. 61–70): when small amounts of template DNA are used as starting material in a PCR, primers that differ slightly in sequence from the corresponding region in a template DNA are used to generate relatively large quantities of a specific DNA fragment that differs from the template sequence only at the positions where the primers differ from the template. For introduction of a mutation into a plasmid DNA, one of the primers is designed to overlap the position of the mutation and to contain the mutation; the sequence of the other is identical to a stretch of sequence of the opposite strand of the plasmid, but this sequence is located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone.

If the ratio of template to product material is extremely low, the vast majority of product DNA fragments incorporate the desired mutation(s). This product material is used to replace the corresponding region in the plasmid that served as PCR template using standard DNA technology. Mutations at separate positions can be introduced simultaneously by either using a mutant second primer, or performing a second PCR with different mutant primers and ligating the two resulting PCR fragments simultaneously to the vector fragment in a three (or more)-part ligation.

In a specific example of PCR mutagenesis, template plasmid DNA (1 μg) is linearized by digestion with a restriction endonuclease that has a unique recognition site in the plasmid DNA outside of the region to be amplified. Of this material, 100 ng is added to a PCR mixture containing PCR buffer, which contains the four deoxynucleotide triphosphates and is included in the GeneAmp™ kits (obtained from Perkin-Elmer Cetus, Norwalk, Conn. and Emeryville, Calif.), and 25 pmole of each oligonucleotide primer, to a final volume of 50 μL. The reaction mixture is overlaid with 35 μL of mineral oil. The reaction mixture is denatured for five minutes at 100° C., placed briefly on ice, and then 1 μL Thermus aquaticus (Taq) DNA polymerase (5 units/μL, purchased from Perkin-Elmer Cetus) is added below the mineral oil layer. The reaction mixture is then inserted into a DNA Thermal Cycler (purchased from Perkin-Elmer Cetus) programmed as follows: (2 min. 55° C.; 30 sec. 72° C., then 19 cycles of the following: 30 sec. 94° C.; 30 sec. 55° C.; and 30 sec. 72° C.).

At the end of the program, the reaction vial is removed from the thermal cycler and the aqueous phase transferred to a new vial, extracted with phenol/chloroform (50:50 vol), and ethanol precipitated, and the DNA is recovered by standard procedures. This material is subsequently subjected to the appropriate treatments for insertion into a vector.

Another method for preparing variants, cassette mutagenesis, is based on the technique described by Wells et al., Gene 34: 315 (1985). The starting material is the plasmid (or other vector) comprising the DNA to be mutated. The codon(s) in the DNA to be mutated are identified. There is a unique restriction endonuclease site on each side of the identified mutation site(s). If no such restriction sites exist, they are generated using the above-described oligonucleotide-mediated mutagenesis method to introduce them at appropriate locations in the DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are compatible with the ends of the linearized plasmid, such that it can be directly ligated to the plasmid. This plasmid now contains the mutated DNA sequence.

(i.) Insertion of Nucleic Acid into Replicable Vector

The nucleic acid (e.g., cDNA or genomic DNA) encoding the mutant antibody is inserted into a replicable vector for further cloning (amplification of the DNA) or for expression. Many vectors are available, and selection of the appropriate vector will generally depend on: 1) whether it is to be used for DNA amplification or for DNA expression; 2) the size of the nucleic acid to be inserted into the vector; and 3) the host cell to be transformed with the vector. Each vector contains various components depending on its function (amplification of DNA or expression of DNA) and the host cell with which it is compatible. The vector components generally include, but are not limited to, one or more of the following: a signal sequence, an origin of replication, one or more marker genes, an enhancer element, a promoter, and a transcription termination sequence.

(ii) Signal Sequence Component

The mutant antibodies of this invention are produced not only directly, but also as a fusion with a heterologous polypeptide, preferably a signal sequence or other polypeptide having a specific cleavage site at the N-terminus of the mature polypeptide variant. In general, the signal sequence may be a component of the vector, or it may be a part of the DNA that is inserted into the vector. The heterologous signal sequence selected should be one that is recognized and processed (i.e., cleaved by a signal peptidase) by the host cell. For prokaryotic host cells that do not recognize and process antibody signal sequence, the signal sequence is substituted by a prokaryotic signal sequence selected, for example, from the group consisting of the alkaline phosphatase, penicillinase, Ipp, or heat-stable enterotoxin II leaders. For yeast secretion the original or wild-type signal sequence may be substituted by, e.g., the yeast invertase leader, yeast alpha factor leader (including, *Saccharomyces* and *Kluyveromyces* α-factor leaders, the latter described in U.S. Pat. No. 5,010,182 issued Apr. 23, 1991), yeast acid phosphatase leader, mouse salivary amylase leader, carboxypeptidase leader, yeast BAR1 leader, *Humicola lanuginosa* lipase leader, the *C. albicans* glucoamylase leader (EP 362,179 published Apr. 4, 1990), or the signal described in WO 90/13646 published Nov. 15, 1990. In mammalian cell expression the original human signal sequence (i.e., the polypeptide presequence that normally directs secretion of the native polypeptide of interest from which the variant of interest is derived from human cells in vivo) is satisfactory, although other mammalian signal sequences may be suitable, such as signal sequences from other animal polypeptides and signal sequences from secreted polypeptides of the same or related species, as well as viral secretory leaders, for example, the herpes simplex gD signal. The DNA for such precursor region is ligated in reading frame to DNA encoding the mature polypeptide variant.

(iii.) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 (ATCC 37,017), or from other commercially available bacterial vectors such as, e.g., pKK223-3 (Pharmacia Fine Chemicals, Uppsala, Sweden) and pGEM1 (Promega Biotech, Madison, Wis.), is suitable for most Gram-negative bacteria, the 2μ plasmid origin is suitable for yeast, and various viral origins (e.g., SV40, polyoma, adenovirus, VSV, or BPV) are useful for cloning vectors in mammalian cells. Generally, the origin of replication component is not needed for mammalian expression vectors (the SV40 origin may typically be used only because it contains the early promoter).

Most expression vectors are "shuttle" vectors, i.e., they are capable of replication in at least one class of organisms but can be transfected into another organism for expression. For example, a vector is cloned in *E. coli* and then the same vector is transfected into yeast or mammalian cells for expression even though it is not capable of replicating independently of the host cell chromosome.

DNA can also be amplified by insertion into the host genome. This is readily accomplished using *Bacillus* species as hosts, for example, by including in the vector a DNA sequence that is complementary to a sequence found in *Bacillus* genomic DNA. Transfection of *Bacillus* with this vector results in homologous recombination with the genome and insertion of the DNA. However, the recovery of genomic DNA encoding the polypeptide variant is more complex than that of an exogenously replicated vector because restriction enzyme digestion is required to excise the DNA.

(iv.) Selection Gene Component

Expression and cloning vectors preferably contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that: (a) confer resistance to antibiotics or other toxins, e.g., ampicillin, neomycin, methotrexate, or tetracycline; (b) complement auxotrophic deficiencies; or (c) supply critical nutrients not available from complex media, e.g., the gene encoding D-alanine racemase for Bacilli.

One example of a selection scheme utilizes a drug to arrest growth of a host cell. The cells that are successfully transformed with a heterologous gene produce a protein conferring drug resistance and thus survive the selection regimen. Examples of such dominant selection use the drugs neomycin (Southern et al., *J. Molec. Appl. Genet.* 1: 327 (1982)), mycophenolic acid (Mulligan et al., *Science* 209: 1422 (1980)), or hygromycin (Sugden et al., *Mol. Cell. Biol.* 5: 410–413 (1985)). The three examples given above employ bacterial genes under eukaryotic control to convey resistance to the appropriate drug G418 or neomycin (geneticin), xgpt (mycophenolic acid), or hygromycin, respectively.

Another example of suitable selectable markers for mammalian cells are those that enable the identification of cells competent to take up the nucleic acid, such as DHFR or thymidine kinase. The mammalian cell transformants are placed under selection pressure that only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes the polypeptide variant. Amplification is the process by which genes in greater demand for the production of a protein critical for growth are reiterated in tandem within the chromosomes of successive generations of recombinant cells. Increased quantities of the polypeptide variant are synthesized from the amplified DNA. Other examples of amplifiable genes include metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub and Chasin, *Proc. Natl. Acad. Sci. USA,* 77: 4216 (1980). The transformed cells are then exposed to increased levels of methotrexate. This leads to the synthesis of multiple copies of the DHFR gene, and, concomitantly, multiple copies of other DNA comprising the expression vectors, such as the DNA encoding the polypeptide variant. This amplification technique can be used with any otherwise suitable host, e.g., ATCC No. CCL61 CHO-K1, notwithstanding the presence of endogenous DHFR if, for example, a mutant DHFR gene that is highly resistant to Mtx is employed (EP 117,060).

Alternatively, host cells (particularly wild-type hosts that contain endogenous DHFR) transformed or co-transformed with DNA sequences encoding the polypeptide variant, wild-type DHFR protein, and another selectable marker such as aminoglycoside 3-phosphotransferase (APH) can be selected by cell growth in medium containing a selection agent for the selectable marker such as an aminoglycosidic antibiotic, e.g., kanamycin, neomycin, or G418. See, U.S. Pat. No. 4,965,199.

A suitable selection gene for use in yeast is the trp1 gene present in the yeast plasmid YRp7 (Stinchcomb et al., *Nature* 282: 39 (1979); Kingsman et al., *Gene* 7: 141 (1979); or Tschemper et al., *Gene* 10: 157 (1980)). The trp1 gene provides a selection marker for a mutant strain of yeast lacking the ability to grow in tryptophan, for example, ATCC No. 44076 or PEP4-1 (Jones, *Genetics* 85: 12 (1977)). The presence of the trp1 lesion in the yeast host cell genome then provides an effective environment for detecting transformation by growth in the absence of tryptophan. Similarly, Leu2-deficient yeast strains (ATCC No. 20,622 or 38,626) are complemented by known plasmids bearing the Leu2 gene.

In addition, vectors derived from the 1.6 µm circular plasmid pKD1 can be used for transformation of *Kluyveromyces* yeasts. Bianchi et al., *Curr. Genet.* 12: 185 (1987). More recently, an expression system for large-scale production of recombinant calf chymosin was reported for *K. lactis*. Van den Berg, *Bio/Technology* 8: 135 (1990). Stable multicopy expression vectors for secretion of mature recombinant human serum albumin by industrial strains of *Kluyveromyces* have also been disclosed. Fleer et al, *Bio/Technology* 9: 968–975 (1991).

(v.) Promoter Component

Expression and cloning vectors preferably contain a promoter that is recognized by the host organism and is operably linked to the nucleic acid. Promoters are untranslated sequences located upstream (5') to the start codon of a structural gene (generally within about 100 to 1000 bp) that control the transcription and translation of particular nucleic acid sequence, such as the nucleic acid sequence of the polypeptide variants herein, to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by a variety of potential host cells are well known. These promoters are operably linked to the DNA encoding the polypeptide variant by removing the promoter from the source DNA by restriction enzyme digestion and inserting the isolated promoter sequence into the vector. The promoter of the polypeptide of interest and many heterologous promoters may be used to direct amplification and/or expression of the DNA. However, heterologous promoters are preferred, as they generally permit greater transcription and higher yields of recombinantly produced polypeptide variant as compared to the promoter of the polypeptide of interest.

Promoters suitable for use with prokaryotic hosts include, for example, the β-lactamase and lactose promoter systems (Chang et al., *Nature* 275: 615 (1978); and Goeddel et al., *Nature* 281: 544 (1979)), alkaline phosphatase, a tryptophan (trp) promoter system (Goeddel, *Nucleic Acids Res.* 8: 4057 (1980) and EP 36,776) and hybrid promoters such as the tac promoter (deBoer et al., *Proc. Natl. Acad. Sci. USA* 80: 21–25 (1983)). However, other known bacterial promoters are suitable. Their nucleotide sequences have been published, thereby enabling a skilled worker operably to ligate them to DNA encoding the polypeptide variant (Siebenlist et al., *Cell* 20: 269 (1980)) using linkers or adaptors to supply any required restriction sites. Promoters for use in bacterial systems also will contain a Shine-Dalgarno (S.D.) sequence operably linked to the DNA encoding the polypeptide variant.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase (Hitzeman et al., *J. Biol. Chem.* 255: 2073 (1980)) or other glycolytic enzymes (Hess et al., *J. Adv. Enzyme Req.* 7: 149 (1968); and Holland, *Biochemistry* 17: 4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in Hitzeman et al., EP 73,657. Yeast enhancers also are advantageously used with yeast promoters.

Transcription of polypeptide variant from vectors in mammalian host cells is controlled, for example, by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, and from the promoter normally associated with the polypeptide variant sequence, provided such promoters are compatible with the host cell systems.

The early and late promoters of the SV40 virus are conveniently obtained as an SV40 restriction fragment that also contains the SV40 viral origin of replication (Fiers et al., *Nature* 273: 113 (1978); Mulligan and Berg, *Science* 209: 1422–1427 (1980); and Pavlakis et al., *Proc. Natl. Acad. Sci. USA* 78: 7398–7402 (1981)). The immediate early promoter of the human cytomegalovirus is conveniently obtained as a Hind III E restriction fragment (Greenaway et al., *Gene* 18: 355–360 (1982)). A system for expressing DNA in mammalian hosts using the bovine papilloma virus as a vector is disclosed in U.S. Pat. No. 4,419,446. A modification of this system is described in U.S. Pat. No. 4,601,978. See also, Gray et al., *Nature* 295: 503–508 (1982) on expressing cDNA encoding immune interferon in monkey cells; Reyes et al., *Nature* 297: 598–601 (1982) on expression of human β-interferon cDNA in mouse cells under the control of a thymidine kinase promoter from herpes simplex virus; Canaani and Berg, *Proc. Natl. Acad. Sci. USA* 79: 5166–5170 (1982) on expression of the human interferon β1 gene in cultured mouse and rabbit cells; and Gorman et al., *Proc. Natl. Acad. Sci. USA* 79: 6777–6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

(vi.) Enhancer Element Component

Transcription of a DNA encoding the polypeptide variant of this invention by higher eukaryotes is often increased by inserting an enhancer sequence into the vector. Enhancers are cis-acting elements of DNA, usually about from 10 to 300 bp, that act on a promoter to increase its transcription. Enhancers are relatively orientation and position independent, having been found 5' (Laimins et al., *Proc. Natl. Acad. Sci. USA* 78: 993 (1981)) and 3' (Lusky et al, *Mol. Cell Bio.* 3: 1108 (1983)) to the transcription unit, within an intron (Banerji et al., *Cell* 33: 729 (1983)), as well as within the coding sequence itself (Osborne et al., *Mol. Cell Bio.* 4: 1293 (1984)). Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers (see also, Yaniv, *Nature* 297: 17–18 (1982)) on enhancing elements for activation of eukaryotic promoters. The enhancer may be spliced into the vector at a position 5' or 3' to the polypeptide-variant-encoding sequence, but is preferably located at a site 5' from the promoter.

(vii.) Transcription Termination Component

Expression vectors used in eukaryotic host cells (yeast, fingi, insect, plant, animal, human, or nucleated cells from other multicellular organisms) also preferably contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the polypeptide variant.

(viii.) Construction and Analysis of Vectors

Construction of suitable vectors containing one or more of the above-listed components preferably employs standard ligation techniques. Isolated plasmids or DNA fragments are cleaved, tailored, and re-ligated in the form desired to generate the plasmids required.

For analysis to confirm correct sequences in plasmids constructed, the ligation mixtures are preferably used to transform *E. coli* (e.g., K12 strain 294 (ATCC 31,446)) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.* 9: 309 (1981) or by the method of Maxam et al., *Methods in Enzymology* 65: 499 (1980).

(ix.) Transient Expression Vectors

Particularly useful in the practice of this invention are expression vectors that provide for the transient expression in mammalian cells of DNA encoding the polypeptide variant. In general, transient expression involves the use of an expression vector that is able to replicate efficiently in a host cell, such that the host cell accumulates many copies of the expression vector and, in turn, synthesizes high levels of a desired polypeptide encoded by the expression vector. Sambrook et al., supra, pp. 16.17–16.22. Transient expression systems, comprising a suitable expression vector and a host cell, allow for the convenient positive identification of polypeptide variants encoded by cloned DNAs, as well as for the rapid screening of such polypeptides for desired biological or physiological properties. Thus, transient expression systems are particularly useful in the invention for purposes of identifying polypeptide variants that are biologically active.

(x.) Suitable Exemplary Vertebrate Cell Vectors

Other methods, vectors, and host cells suitable for adaptation to the synthesis of the polypeptide variant in recombinant vertebrate cell culture are described in Gething et al., *Nature* 293: 620–625 (1981); Mantei et al., *Nature* 281: 40–46 (1979); EP 117,060; and EP 117,058. An exemplary plasmid for mammalian cell culture production of the antibody of the invention is pRK5 (EP 307,247) or pSVI6B (WO 91/08291 published Jun. 13, 1991). The pRK5 derivative pRK5B (Holmes et al., *Science*, 253: 1278–1280 (1991)) is particularly suitable herein for such expression.

c. Selection and Transformation of Host Cells

Suitable host cells for cloning or expressing the vectors herein include, for example, the prokaryote, yeast, or higher eukaryote cells described above. Exemplary prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as *Bacilli* such as *B. subtilis* and *B. licheniformis* (e.g., *B. licheniformis* 41P disclosed in DD 266,710 published Apr. 12, 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), *E. coli* DH5.alpha., and *E. coli* W3110 (ATCC 27,325) are suitable. These examples are illustrative rather than limiting. Strain W3110 is a preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1 A2, which has the complete genotype tonAΔ; *E. coli* W3110 strain 9E4, which has the complete genotype tonAΔ ptr3; *E. coli* W3110 strain 27C7 (ATCC 55,244), which has the complete genotype tonA ptr3 phoAΔE15 Δ(argF-lac) 169 ΔdegP ΔompT kan$^r$; *E. coli* W3110 strain 37D6, which has the complete genotype tonA ptr3 phoAΔE15.DELTA.(argF-lac)169 ΔdegP ΔompT Δrbs7 ilvG kan.sup.R; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued Aug. 7, 1990. Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for polypeptide-variant-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe* (Beach and Nurse, *Nature* 290: 140 (1981); EP 139,383 published May 2, 1985); *Kluyveromyces* hosts (U.S. Pat. No. 4,943,529; Fleer et al., supra) such as, e.g., *K. lactis* (MW98-8C, CBS683, CBS4574; Louvencourt et al., *J. Bacteriol.* 737 (1983)), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., supra), *K. thermotolerans*, and *K. marxianus; yarrowia* (EP 402,226); *Pichia pastoris* (EP 183,070; Sreekrishna et al., *J. Basic Microbiol.* 28: 265–278 (1988)); *Candida; Trichoderma reesia* (EP 244,234); *Neurospora crassa* (Case et al., *Proc. Natl. Acad. Sci. USA* 76: 5259–5263 (1979)); *Schwanniomyces* such as *Schwanniomyces occidentalis* (EP 394,538 published Oct. 31, 1990); and filamentous fungi such as, e.g., *Neurospora, Penicillium, Tolypocladium* (WO 91/00357 published Jan. 10, 1991), and *Aspergillus* hosts such as *A. nidulans* (Ballance et al., *Biochem. Biophys. Res. Commun.* 112: 284–289 (1983); Tilburn et al., *Gene* 26: 205–221 (1983); Yelton et al., *Proc. Natl. Acad. Sci. USA* 81: 1470–1474 (1984)) and *A. niger* (Kelly and Hynes, *EMBO J.* 4: 475–479 (1985)).

Suitable host cells for the production of the polypeptide variant are derived from multicellular organisms. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. See, e.g., Luckow et al., *Bio/Technology* 6: 47–55 (1988); Miller et al., in Genetic Engineering, Setlow, J. K. et al., eds., Vol. 8 (Plenum Publishing, 1986), pp. 277–279; and Maeda et al., *Nature* 315: 592–594 (1985). A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can be utilized as hosts. Typically, plant cells are transfected by incubation with certain strains of the bacterium *Agrobacterium tumefaciens*, which has been previously manipulated to contain the DNA. During incubation of the plant cell culture with *A. tumefaciens*, for example, the DNA encoding the polypeptide variant is transferred to the plant cell host such that it is transfected, and will, under appropriate conditions, express the DNA. In addition, regulatory and signal sequences compatible with plant cells are available, such as the nopaline synthase promoter and polyadenylation signal sequences. Depicker et al., *J. Mol. Appl. Gen.* 1: 561 (1982). In addition, DNA segments isolated from the upstream region of the T-DNA 780 gene are capable of activating or increasing transcription levels of plant-expressible genes in recombinant DNA-containing plant tissue. EP 321,196 published Jun. 21, 1989.

Interest has generally been greatest in vertebrate cells, and propagation of vertebrate cells in culture (tissue culture) has become a routine procedure in recent years (Tissue Culture, Academic Press, Kruse and Patterson, editors (1973)). Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36: 59 (1977)); baby hamster kidney cells (BHK, ATCC CCL 10); Chinese hamster ovary cells/-DHFR (CHO, Urlaub and Chasin, *Proc. Natl. Acad. Sci. USA* 77: 4216 (1980)); mouse sertoli cells (TM4, Mather, *Biol. Reprod.*, 23: 243–251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor cells (MMT 060562, ATCC CCL51); TRI cells (Mather et al., *Annals N.Y. Acad. Sci.* 383: 44–68 (1982)); MRC 5 cells; FS4 cells; and a human hepatoma line (Hep G2).

Host cells are transfected and preferably transformed with the above-described expression or cloning vectors of this invention and cultured in conventional nutrient media modified as appropriate for inducing promoters, selecting transformants, or amplifying the genes encoding the desired sequences. Transfection refers to the taking up of an expression vector by a host cell whether or not any coding sequences are in fact expressed. Numerous methods of transfection are known to the ordinarily skilled artisan, for example, CaPO$_4$ and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., supra, or electroporation is preferably used for prokaryotes or other cells that contain substantial cell-wall barriers. Infection with *Agrobacterium tumefaciens* is preferably used for transformation of certain plant cells, as described by Shaw et al., *Gene* 23: 315 (1983) and WO 89/05859 published Jun. 29, 1989. In addition, plants may be transfected using ultrasound treatment as described in WO 91/00358 published Jan. 10, 1991.

For mammalian cells without such cell walls, the calcium phosphate precipitation method of Graham and van der Eb,

*Virology* 52: 456–457 (1978) is preferred. General aspects of mammalian cell host system transformations have been described by Axel in U.S. Pat. No. 4,399,216 issued Aug. 16, 1983. Transformations into yeast are preferably carried out according to the method of Van Solingen et al., *J. Bact.*, 130: 946 (1977) and Hsiao et al., Proc. Natl. Acad. Sci. (USA) 76: 3829 (1979). Other methods for introducing DNA into cells, such as by nuclear microinjection, electroporation, bacterial protoplast fusion with intact cells, or polycations, e.g., polybrene, polyornithine, etc., may also be used in practicing the present invention. For various techniques for transforming mammalian cells, see Keown et al., *Methods in Enzymology* 185: 527–537 (1990) and Mansour et al., *Nature* 336: 348–352 (1988).

d. Culturing the Host Cells

Prokaryotic cells used to produce the polypeptide variant of this invention are cultured in suitable media as described generally in Sambrook et al., supra. The mammalian host cells used to produce the polypeptide variant of this invention may be cultured in a variety of media. Commercially available media such as, Ham's F-10 (Sigma), F-12 (Sigma), Minimal Essential Medium (MEM, Sigma), RPMI-1640 (Sigma), Dulbecco's Modified Eagle's Medium (D-MEM, Sigma), and D-MEM/F-12 (Gibco BRL) are suitable for culturing the host cells. In addition, any of the media described, for example, in Ham and Wallace, *Methods in Enzymology* 58: 44 (1979); Barnes and Sato, *Anal. Biochem.* 102: 255 (1980); U.S. Pat. No. 4,767,704; 4,657,866; 4,927,762; 5,122,469; or 4,560,655; U.S. Pat. No. 30,985; WO 90/03430; or WO 87/00195 may be used as culture media for the host cells. Any of these media may be supplemented as necessary with hormones and/or other growth factors (e.g., insulin, transferrin, aprotinin, and/or epidermal growth factor (EGF)), salts (e.g., sodium chloride, calcium, magnesium, and phosphate), buffers (e.g., HEPES), nucleosides (such as adenosine and thymidine), antibiotics (e.g., Gentamycin™), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression or modification thereto and will be apparent to the ordinarily skilled artisan.

In general, principles, protocols, and practical techniques for maximizing the productivity of in vitro mammalian cell cultures can be found in MAMMALIAN CELL BIOTECHNOLOGY: A PRACTICAL APPROACH, M. Butler, ed. (IRL Press, 1991). The host cells referred to in this disclosure encompass cells in in vitro culture as well as cells that are within a host animal.

e. Detecting Gene Amplification/Expression

Gene amplification and/or expression is preferably measured in a sample directly, for example, by conventional Southern blotting, northern blotting to quantitate the transcription of mRNA (Thomas, *Proc. Natl. Acad. Sci. USA* 77: 5201–5205 (1980)), dot blotting (DNA analysis), or in situ hybridization, using an appropriately labeled probe, based on the sequences provided herein. Various labels may be employed, most commonly radioisotopes, particularly $^{32}P$. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescent moieties, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like. A particularly sensitive staining technique suitable for use in the present invention is described by Hsu et al., *Am. J. Clin. Path.* 75: 734–738 (1980).

Antibodies useful for immunohistochemical staining and/or assay of sample fluids may be either monoclonal or polyclonal, and may be prepared in any mammal. Conveniently, the antibodies may be prepared against an antibody of the invention.

f. Purification of Polypeptide

If the mutant antibody is produced intracellularly, as a first step, the particulate debris, either host cells or lysed fragments, is removed, for example, by centrifugation or ultrafiltration; optionally, the protein may be concentrated with a commercially available protein concentration filter, followed by separating the polypeptide variant from other impurities by one or more steps selected from immunoaffinity chromatography, ion-exchange column fractionation (e.g., on diethylaminoethyl (DEAE) or matrices containing carboxymethyl or sulfopropyl groups), chromatography on Blue-Sepharose, CM Blue-Sepharose, MONO-Q, MONO-S, lentil lectin-Sepharose, WGA-Sepharose, Con A-Sepharose, Ether Toyopearl, Butyl Toyopearl, Phenyl Toyopearl, or protein A Sepharose, SDS-PAGE chromatography, silica chromatography, chromatofocusing, reverse phase HPLC (e.g., silica gel with appended aliphatic groups), gel filtration using, e.g., Sephadex molecular sieve or size-exclusion chromatography, chromatography on columns that selectively bind the polypeptide, and ethanol or ammonium sulfate precipitation.

Recombinant polypeptide variant produced in bacterial culture may usually be isolated by initial extraction from cell pellets, followed by one or more concentration, salting-out, aqueous ion-exchange, or size-exclusion chromatography steps. Additionally, the recombinant polypeptide variant may be purified by affinity chromatography. Finally, HPLC may be employed for final purification steps. When microbial cells are employed in expression of nucleic acid encoding the polypeptide variant may be disrupted by any convenient method, including freeze-thaw cycling, sonication, mechanical disruption, or use of cell lysing agents.

A protease inhibitor, e.g., methylsulfonylfluoride (PMSF) may be included in any of the foregoing steps to inhibit proteolysis and antibiotics may be included to prevent the growth of adventitious contaminants.

Within another embodiment, supernatants from systems which secrete recombinant polypeptide variant into culture medium are first concentrated using a commercially available protein concentration filter, for example, an Amicon or Millipore Pellicon ultrafiltration unit. Following the concentration step, the concentrate may be applied to a suitable purification matrix. For example, a suitable affinity matrix may comprise a ligand for the protein, a lectin or antibody molecule bound to a suitable support. Alternatively, an anion-exchange resin may be employed, for example, a matrix or substrate having pendant DEAE groups. Suitable matrices include acrylamide, agarose, dextran, cellulose, or other types commonly employed in protein purification. Alternatively, a cation-exchange step may be employed. Suitable cation exchangers include various insoluble matrices comprising sulfopropyl or carboxymethyl groups. Sulfopropyl groups are particularly preferred.

Finally, one or more RP-HPLC steps employing hydrophobic RP-HPLC media, e.g., silica gel having pendant methyl or other aliphatic groups, may be employed to further purify a polypeptide variant composition. Some or all of the foregoing purification steps, in various combinations, can also be employed to provide a homogeneous recombinant polypeptide variant.

Fermentation of yeast, which produces the polypeptide variant as a secreted polypeptide greatly simplifies purification. Secreted recombinant polypeptide variant resulting from a large-scale fermentation may be purified by methods analogous to those disclosed by Urdal et al., *J. Chromatog.* 296: 171 (1984). This reference describes two sequential, RP-HPLC steps for purification of recombinant human IL-2 on a preparative HPLC column. Alternatively, techniques such as affinity chromatography, may be utilized to purify the polypeptide variant.

Mammalian polypeptide variant synthesized in recombinant culture is characterized by the presence of non-human cell components, including proteins, in amounts and of a character which depend on the purification steps taken to recover the polypeptide variant from culture. These components ordinarily will be from yeast, prokaryotic, or non-human higher eukaryotic origin and preferably are present in innocuous contaminant quantities, on the order of less than about 1% by weight.

In a preferred embodiment, the present invention provides for the cloning of CHA255. Briefly, hybridoma cells are grown and tested for antibody production on microtiter plates coated with an immobilized radioactive or fluorescent chelate conjugate. The mRNA is harvested and cDNAs are synthesized using reverse transcriptase, preferably with poly T and 3' MuIgGV$_H$ and MuIgλV$_L$ primers. The V$_H$ and V$_L$ genes are amplified via PCR, and cloned into a vector, preferably a pT7 Blue vector. Positive clones are detected by, for example, β-galactosidase complementation for example Confirmation of insert size is preferably performed using a PCR screen of crude boiled cell lysates. In a further preferred embodiment, confirmation uses the adjacent T7 and U19 primer sites in a pT7 Blue vector. Agarose Gel analysis is preferably used to probe the length of the inserts for both V$_H$ and V$_L$. The clones are preferably sequenced in both directions. In a further preferred embodiment, the T7, U19 and M13 reverse primers are used for sequencing and the the clones are sequenced in both directions and aligned.

Figure 2A:
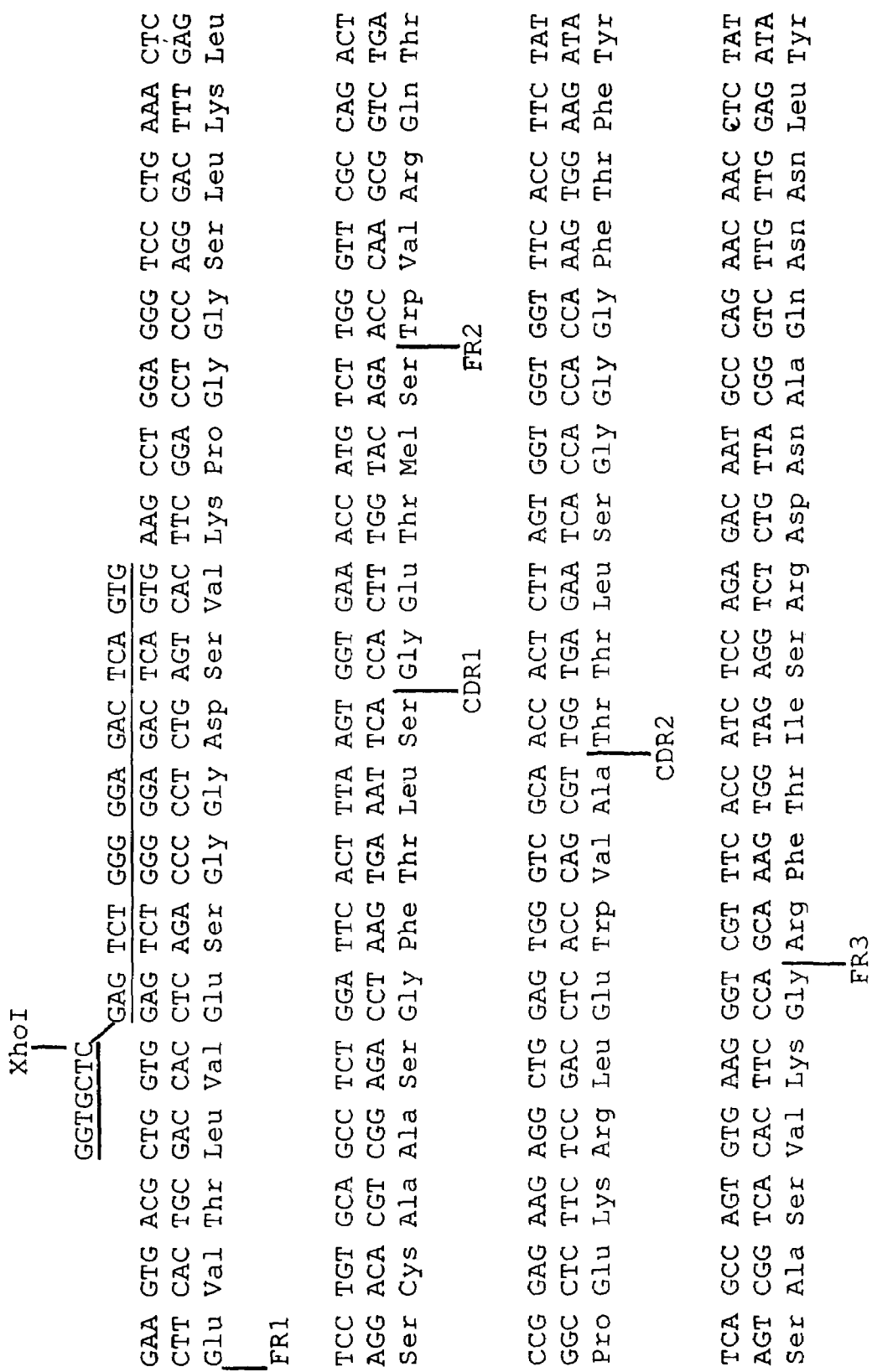
FIG. 2 is the $V_H$ sequence of CHA255. Regions of the $V_H$ gene are marked. Cloning primers with XhoI and ApaI sites are shown.

In an exemplary embodiment, plasmids for the V$_L$ and V$_H$ are prepared by a method (pT7V$_L$CHA255 and pT7V$_H$CHA255). PCR mutagenesis of the V$_L$ gene was perfomed to provide S95C V$_L$ CHA255. A flow diagram for an exemplary procedure is set forth in FIG. 1. Separate PCR amplification reactions with primers T7/S95C and U19/KXbaI result in partial inserts of the V$_L$ gene, which overlap. Primer S95C base mismatches to change Ser95 to Cys, and primer KXbaI destroys the XbaI site in the T7 primer. Mixing fractions from each reaction, denaturing at 95° C., and cooling to 55° C. formed a mixture of heteroduplexes. The heteroduplexes were extended with Taq polymerase and dNTPs. PCR amplification of these templates resulted in two species of product with the same size, one with the S95C mutation and an intact XbaI site, and another with a destroyed XbaI site and no S95C mutation. Restriction digests with XbaI and BamHI, followed by ligation into the parent vector, led almost exclusively to colonies enriched in the desired mutation. After sequencing, primers were developed to clone the variable heavy and light domains into the vector NPC3tt (FIG. 2 and FIG. 3).

Figure 4A:
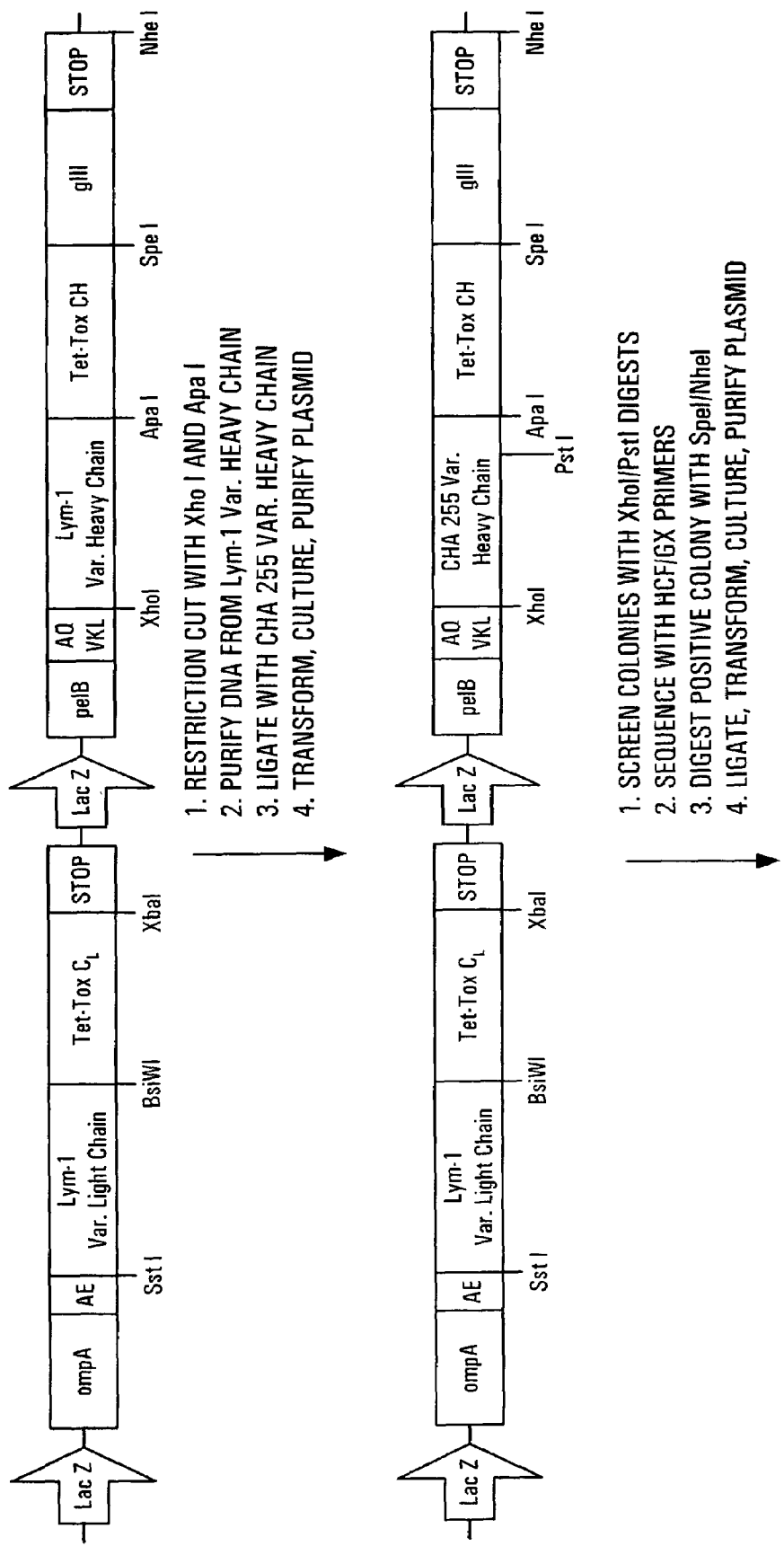
FIG. 4 is a flow diagram of the construction of CHA255/TT chimeric Fab from Lym-1 chimeric Fab.
Figure 4B:
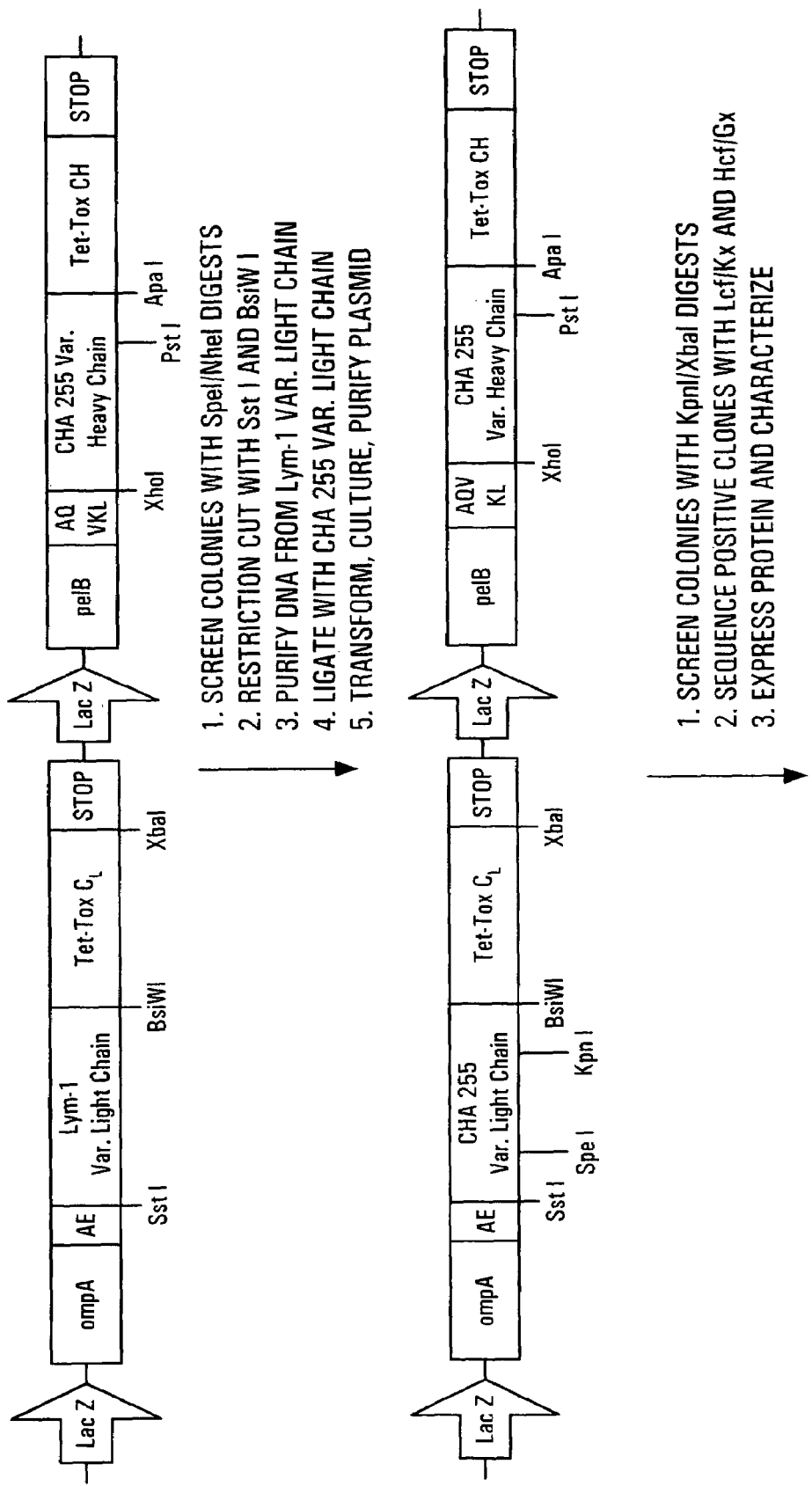

NPC3tt is a vector designed to express two polypeptide chains under control of the lac promoter for periplasmic expression with ompA and pelB leader sequences. It contains the Fab heavy and light domains of a human tetanus toxoid antibody. Sequential cloning of the CHA255 mouse variable heavy chains between the XhoI and ApaI sites followed by insertion of the variable light chain with S95C mutation between the SstI and BsiWI sites results in a human/mouse chimera (FIG. 4).

g. Covalent Modifications of Polypeptide Variants

Covalent modifications of polypeptide variants are included within the scope of this invention. The modifications are made by chemical synthesis or by enzymatic or chemical cleavage or elaboration of the mutant antibody of the invention. Other types of covalent modifications of the polypeptide variant are introduced into the molecule by reacting targeted amino acid residues of the polypeptide variant with an organic derivatizing agent that is capable of reacting with selected side chains or the N- or C-terminal residues.

The modifications of the mutant antibody of the invention include the attachment of agents to, for example, enhance antibody stability, water-solubility, in vivo half-life and to target the antibody to a desired target tissue. Targeting the antibody preferably utilizes the covalent attachment of one or more moieties that recognize a structure on the surface of the cell to which the antibody is targeted. Exemplary targeting species include, but are not limited to, antibodies, hormones, lectins, and ligands for cell-surface receptors. Many methods are known in the art for derivatizing both the mutant antibodies of the invention and useful targeting agents. The discussion that follows is illustrative of reactive groups found on the mutant antibody and on the targeting agent and methods of forming conjugates between the mutant antibody and the targeting agent. The use of homo- and hetero-bifunctional derivatives of each of the reactive functionalities discussed below to link the mutant antibody to the targeting moiety is within the scope of the present invention.

Cysteinyl residues most commonly are reacted with agents that include α-haloacetates (and corresponding amines), such as chloroacetic acid or chloroacetamide, to give carboxymethyl or carboxyamidomethyl derivatives. Cysteinyl residues also are derivatized by reaction with bromotrifluoroketones, α-bromo-β-(5-imidozoyl)carboxylic acids, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with, for example, groups that include pyrocarbonate at pH 5.5–7.0 because this agent is relatively specific for the histidyl side chain. Para-bromophenacyl halides also are useful; the reaction is preferably performed in 0.1 M sodium cacodylate at pH 6.0.

Lysinyl and amino-terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine site. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method described above being suitable.

Carboxyl side groups (aspartyl or glutamyl) are selectively modified by reaction with carbodiimides (R—N=C=N—R'), where R and R' are different alkyl groups, such as 1-cyclohexyl-3-(2-morpholinyl-4-ethyl)carbodiimide or 1-ethyl-3-(4-azo-4,4-dimethylpentyl)carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the .alpha.-amino groups of lysine, arginine, and histidine side chains (T. E. Creighton, PROTEINS: STRUCTURE AND MOLECULAR PROPERTIES, W. H. Freeman & Co., San Francisco, pp. 79–86 (1983)), acetylation of the N-terminal amine, and amidation of any C-terminal carboxyl group.

Another type of covalent modification of the polypeptide variant included within the scope of this invention comprises altering the original glycosylation pattern of the polypeptide variant. By altering is meant deleting one or more carbohydrate moieties found in the polypeptide variant, and/or adding one or more glycosylation sites that are not present in the polypeptide variant.

Glycosylation of the mutant antibodies is typically either N-linked or N-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the mutant antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original polypeptide variant (for O-linked glycosylation sites). For ease, the polypeptide variant amino acid sequence is preferably altered through changes at the DNA level, particularly by mutating the DNA encoding the polypeptide variant at preselected bases such that codons are generated that will translate into the desired amino acids. The DNA mutation(s) may be made using methods described above.

Another means of increasing the number of carbohydrate moieties on the mutant antibody is by chemical or enzymatic coupling of glycosides to the polypeptide variant. These procedures are advantageous in that they do not require production of the polypeptide variant in a host cell that has glycosylation capabilities for N- or O-linked glycosylation. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. These methods are described in WO 87/05330 published Sep. 11, 1987, and in Aplin and Wriston, CRC CRIT. REV. BIOCHEM., pp. 259–306 (1981).

Removal of any carbohydrate moieties present on the mutant antibody is accomplished either chemically or enzymatically. Chemical deglycosylation requires exposure of the polypeptide variant to the compound trifluoromethanesulfonic acid, or an equivalent compound. This treatment results in the cleavage of most or all sugars except the linking sugar (N-acetylglucosamine or N-acetylgalactosamine), while leaving the mutant antibody intact. Chemical deglycosylation is described by Hakimuddin et al., Arch. Biochem. Biophys. 259: 52 (1987) and by Edge et al., Anal. Biochem. 118: 131 (1981). Enzymatic cleavage of carbohydrate moieties on polypeptide variants can be achieved by the use of a variety of endo- and exo-glycosidases as described by Thotakura et al., Meth. Enzymol. 138: 350 (1987).

Another type of covalent modification of the polypeptide variant comprises linking the polypeptide variant to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or U.S. Pat. No. 4,179,337. The polymers are added to alter the properties of the mutant antibody or, alternatively, they serve as spacer groups between the targeting agent and the mutant antibody.

h. Preparation of the Mutant Antibody-Targeting Moiety Conjugate

The targeted mutant antibodies of the invention are exemplified in the discussion that follows by a class of antibodies of the invention that are targeted by attachment to tissue-specific antibodies. Antibodies that are reactive with surface antigens on many human cells are known in the art. In a preferred embodiment, the targeting antibody is one binding with human carcinoma cell. Antibody-targeting moiety conjugates can be prepared by covalent modification of the antibody and the targeting agent to link them together as described in in Hellstrom et al., U.S. Pat. No. 6,020,145, for example. Alternatively, the antibody-targeting moiety conjugates can be generated as fusion proteins.

Preparation of the immunoconjugate for the present targeting system includes attachment of an enzymatic or component (AC) to an antibody and forming a stable complex without compromising the activity of either component. An exemplary strategy involves incorporation of a protected sulfhydryl onto the AC using the heterobifunctional crosslinker SPDP (n-succinimidyl-3-(2-pyridyldithio)propionate and then deprotecting the sulfhydryl for formation of a disulfide bond with another sulfhydryl on the antibody. Instead of destabilizing the antibody with reducing agents to generate free sulfhydryls, new sulfhydryls are preferably incorporated onto the mutant antibody using SPDP. In the protected form, the SPDP generated sulfhydryls on the antibody react with the free sulfhydryls incorporated onto the AC forming the required disulfide bonds. By optimizing reaction conditions, the degree of SPDP modification of each component is controlled, thus maintaining maximum activity of each component. SPDP reacts with primary amines and the incorporated sulfhydryl is protected by 2-pyridylthione.

If SPDP should affect the activities of either the antibody (e.g., the moiety binding to the reactive chelate) or the AC, there are a number of additional crosslinkers such as 2-iminothiolane or N-succinimidyl S-acetylthioacetate (SATA), available for forming disulfide bonds. 2-iminothiolane reacts with primary amines, instantly incorporating an unprotected sulfhydryl onto the protein. SATA also amines, but incorporates a protected sulfhydryl, which is later deacetylated using hydroxylamine to produce a free sulfhydryl. In each case, the incorporated sulfhydryl is free to react with other sulfhydryls or protected sulfhydryl, like SPDP, forming the required disulfide bond.

The above-described strategy is exemplary and not limiting of linkers of use in the invention. Other crosslinkers are available that can be used in different strategies for crosslinking the targeting agent to the mutant antibody. For example, TPCH(S-(2-thiopyridyl)-L-cysteine hydrazide and TPMPH ((S-(2-thiopyridyl) mercapto-propionohydrazide) react at the carbohydrate moieties of glycoproteins that have been previously oxidized by mild periodate treatment, thus forming a hydrazone bond between the hydrazide portion of the crosslinker and the periodate generated aldehydes. The placement of this crosslinker on the antibody is beneficial since the modification is site-specific and will not interfere with the antigen binding site of the antibody. TPCH and TPMPH introduce a 2-pyridylthione protected sulfhydryl group onto the antibody, which can be deprotected with DTT and then subsequently used for conjugation, such as forming disulfide bonds between components.

If disulfide bonding is found unsuitable for producing stable conjugates, other crosslinkers may be used that incorporate more stable bonds between components. The heterobifunctional crosslinkers GMBS (N-gama-malimidobutyryloxy)succinimide) and SMCC (succinimidyl 4-(N-maleimido-methyl)cyclohexane) react with primary amines, thus introducing a maleimide group onto the component. This maleimide group can subsequently react with sulfhydryls on the other component, which can be introduced by previously mentioned crosslinkers, thus forming a stable thioether bond between the components. If steric hindrance between components interferes with either component's activity, crosslinkers can be used which introduce long spacer arms between components and include derivatives of some of the previously mentioned crosslinkers (i.e., SPDP). Thus there is an abundance of suitable crosslinkers, which are useful; each of which is selected depending on the effects it has on optimal immunoconjugate production.

A variety of reagents are used to modify the components of the conjugate with intramolecular chemical crosslinks (for reviews of crosslinking reagents and crosslinking procedures see: Wold, F., Meth. Enzymol. 25: 623–651, 1972; Weetall, H. H., and Cooney, D. A., In: ENZYMES AS DRUGS. (J. S. Holcenberg, and J. Roberts, eds.) pp. 395–442, Wiley, New York, 1981; Ji, T. H., Meth. Enzymol. 91: 580–609, 1983; Mattson et al., Mol. Biol. Rep. 17: 167–183, 1993, all of which are incorporated herein by reference). Preferred useful crosslinking reagents are derived from various zero-length, homo-bifunctional, and hetero-bifunctional crosslinking reagents. Zero-length crosslinking reagents include direct conjugation of two intrinsic chemical groups with no introduction of extrinsic material. Agents that catalyze formation of a disulfide bond belong to this category. Another example are reagents that induce condensation of a carboxyl and a primary amino group to form an amide bond such as carbodiimides, ethylchloroformate, Woodward's reagent K (2-ethyl-5-phenylisoxazolium-3'-sulfonate), and carbonyldiimidazole. In addition to these chemical reagents, the enzyme transglutaminase (glutamyl-peptide γ-glutamyl-transferase; EC 2.3.2.13) may be used as a zero-length crosslinking reagent. This enzyme catalyzes acyl transfer reactions at carboxamide groups of protein-bound glutaminyl residues, usually with a primary amino group as substrate. Preferred homo- and hetero-bifunctional reagents contain two identical or two dissimilar sites, respectively, which may be reactive for amino, sulfhydryl, guanidino, indole, or nonspecific groups.

i. Preferred Specific Sites in Crosslinking Reagents

1. Amino-Reactive Groups

In one preferred embodiment, the sites are amino-reactive groups. Useful non-limiting examples of amino-reactive groups include N-hydroxysuccinimide (NHS) esters, imidoesters, isocyanates, acylhalides, arylazides, p-nitrophenyl esters, aldehydes, and sulfonyl chlorides.

NHS esters react preferentially with the primary (including aromatic) amino groups of the affinity component. The imidazole groups of histidines are known to compete with primary amines for reaction, but the reaction products are unstable and readily hydrolyzed. The reaction involves the nucleophilic attack of an amine on the acid carboxyl of an NHS ester to form an amide, releasing the N-hydroxysuccinimide. Thus, the positive charge of the original amino group is lost.

Imidoesters are the most specific acylating reagents for reaction with the amine groups of the conjugate components. At a pH between 7 and 10, imidoesters react only with primary amines. Primary amines attack imidates nucleophilically to produce an intermediate that breaks down to amidine at high pH or to a new imidate at low Ph. The new imidate can react with another primary amine, thus crosslinking two amino groups, a case of a putatively monofunctional imidate reacting bifunctionally. The principal product of reaction with primary amines is an amidine that is a stronger base than the original amine. The positive charge of the original amino group is therefore retained. As a result, imidoesters do not affect the overall charge of the conjugate.

Isocyanates (and isothiocyanates) react with the primary amines of the conjugate components to form stable bonds. Their reactions with sulfhydryl, imidazole, and tyrosyl groups give relatively unstable products.

Acylazides are also used as amino-specific reagents in which nucleophilic amines of the affinity component attack acidic carboxyl groups under slightly alkaline conditions, e.g. pH 8.5.

Arylhalides such as 1,5-difluoro-2,4-dinitrobenzene react preferentially with the amino groups and tyrosine phenolic groups of the conjugate components, but also with its sulfhydryl and imidazole groups.

p-Nitrophenyl esters of mono- and dicarboxylic acids are also useful amino-reactive groups. Although the reagent specificity is not very high, α- and ε-amino groups appear to react most rapidly.

Aldehydes such as glutaraldehyde react with primary amines of the conjugate components (e.g., 1-amino group of lysine residues). Glutaraldehyde, however also displays reactivity with several other amino acid side chains including those of cysteine, histidine, and tyrosine. Since dilute glutaraldehyde solutions contain monomeric and a large number of polymeric forms (cyclic hemiacetal) of glutaraldehyde, the distance between two crosslinked groups within the affinity component varies. Although unstable Schiff bases are formed upon reaction of the protein amino groups with the aldehydes of the polymer, glutaraldehyde is capable of modifying the affinity component with stable crosslinks. At pH 6–8, the pH of typical crosslinking conditions, the cyclic polymers undergo a dehydration to form α-β unsaturated aldehyde polymers. Schiff bases, however, are stable, when conjugated to another double bond. The resonant interaction of both double bonds prevents hydrolysis of the Schiff linkage. Furthermore, amines at high local concentrations can attack the ethylenic double bond to form a stable Michael addition product.

Aromatic sulfonyl chlorides react with a variety of sites of the conjugate components, but reaction with the amino groups is the most important, resulting in a stable sulfonamide linkage.

2. Sulfhydryl-Reactive Groups

In another preferred embodiment, the sites are sulfhydryl-reactive groups. Useful non-limiting examples of sulfhydryl-reactive groups include maleimides, alkyl halides, pyridyl disulfides, and thiophthalimides.

Maleimides react preferentially with the sulfhydryl group of the conjugate components to form stable thioether bonds. They also react at a much slower rate with primary amino groups and the imidazole groups of histidines. However, at pH 7 the maleimide group can be considered a sulfhydryl-specific group, since at this pH the reaction rate of simple thiols is 1000-fold greater than that of the corresponding amine.

Alkyl halides react with sulfhydryl groups, sulfides, imidazoles, and amino groups. At neutral to slightly alkaline pH, however, alkyl halides react primarily with sulfhydryl groups to form stable thioether bonds. At higher pH, reaction with amino groups is favored.

Pyridyl disulfides react with free sulfhydryls via disulfide exchange to give mixed disulfides. As a result, pyridyl disulfides are the most specific sulfhydryl-reactive groups.

Thiophthalimides react with free sulfhydryl groups to form also disulfides.

3. Guanidino-Reactive Groups

In another embodiment, the sites are guanidino-reactive groups. A useful non-limiting example of a guanidino-reactive group is phenylglyoxal. Phenylglyoxal reacts primarily with the guanidino groups of arginine residues in the affinity component. Histidine and cysteine also react, but to a much lesser extent.

4. Indole-Reactive Groups

In another embodiment, the sites are indole-reactive groups. Useful non-limiting examples of indole-reactive groups are sulfenyl halides. Sulfenyl halides react with tryptophan and cysteine, producing a thioester and a disulfide, respectively. To a minor extent, methionine may undergo oxidation in the presence of sulfenyl chloride.

5. Carboxyl-Reactive Residue

In another embodiment, carbodiimides soluble in both water and organic solvent, are used as carboxyl-reactive reagents. These compounds react with free carboxyl groups forming a pseudourea that can then couple to available amines yielding an amide linkage (Yamada et al., *Biochemistry* 20: 4836–4842, 1981) teach how to modify a protein with carbodiimde.

j. Preferred Nonspecific Sites in Crosslinking Reagents

In addition to the use of site-specific reactive moieties, the present invention contemplates the use of non-specific reactive groups to link the mutant antibody to the targeting moiety. Non-specific groups include photoactivatable groups, for example.

In another preferred embodiment, the sites are photoactivatable groups. Photoactivatable groups, completely inert in the dark, are converted to reactive species upon absorption of a photon of appropriate energy. In one preferred embodiment, photoactivatable groups are selected from precursors of nitrenes generated upon heating or photolysis of azides. Electron-deficient nitrenes are extremely reactive and can react with a variety of chemical bonds including N—H, O—H, C—H, and C=C. Although three types of azides (aryl, alkyl, and acyl derivatives) may be employed, arylazides are presently preferrred. The reactivity of arylazides upon photolysis is better with N—H and O—H than C—H bonds. Electron-deficient arylnitrenes rapidly ring-expand to form dehydroazepines, which tend to react with nucleophiles, rather than form C—H insertion products. The reactivity of arylazides can be increased by the presence of electron-withdrawing substituents such as nitro or hydroxyl groups in the ring. Such substituents push the absorption maximum of arylazides to longer wave length. Unsubstituted arylazides have an absorption maximum in the range of 260–280 nm, while hydroxy and nitroarylazides absorb significant light beyond 305 nm. Therefore, hydroxy and nitroarylazides are most preferable since they allow one to employ less harmful photolysis conditions for the affinity component than unsubstituted arylazides.

In another preferred embodiment, photoactivatable groups are selected from fluorinated arylazides. The photolysis products of fluorinated arylazides are arylnitrenes, all of which undergo the characteristic reactions of this group, including C—H bond insertion, with high efficiency (Keana et al., *J. Org. Chem.* 55: 3640–3647, 1990).

In another embodiment, photoactivatable groups are selected from benzophenone residues. Benzophenone reagents generally give higher crosslinking yields than arylazide reagents.

In another embodiment, photoactivatable groups are selected from diazo compounds, which form an electron-deficient carbene upon photolysis. These carbenes undergo a variety of reactions including insertion into C—H bonds, addition to double bonds (including aromatic systems), hydrogen attraction and coordination to nucleophilic centers to give carbon ions.

In still another embodiment, photoactivatable groups are selected from diazopyruvates. For example, the p-nitrophenyl ester of p-nitrophenyl diazopyruvate reacts with aliphatic amines to give diazopyruvic acid amides that undergo ultraviolet photolysis to form aldehydes. The photolyzed diazopyruvate-modified affinity component will react like formaldehyde or glutaraldehyde forming intraprotein crosslinks.

k. Homobifunctional Reagents

1. Homobifunctional Crosslinkers Reactive with Primary Amines

Synthesis, properties, and applications of such reagents are described in the literature (for reviews of crosslinking procedures and reagents, see above). Many reagents are available (e.g., Pierce Chemical Company, Rockford, Ill.; Sigma Chemical Company, St. Louis, Mo.; Molecular Probes, Inc., Eugene, Oreg.).

Preferred, non-limiting examples of homobifunctional NHS esters include disuccinimidyl glutarate (DSG), disuccinimidyl suberate (DSS), bis(sulfosuccinimidyl) suberate (BS), disuccinimidyl tartarate (DST), disulfosuccinimidyl tartarate (sulfo-DST), bis-2-(succinimidooxycarbonyloxy) ethylsulfone (BSOCOES), bis-2-(sulfosuccinimidooxycarbonyloxy)ethylsulfone (sulfo-BSOCOES), ethylene glycolbis(succinimidylsuccinate) (EGS), ethylene glycolbis (sulfosuccinimidylsuccinate) (sulfo-EGS), dithiobis (succinimidylpropionate) (DSP), and dithiobis (sulfosuccinimidylpropionate) (sulfo-DSP). Preferred, non-limiting examples of homobifunctional imidoesters include dimethyl malonimidate (DMM), dimethyl succinimidate (DMSC), dimethyl adipimidate (DMA), dimethyl pimelimidate (DMP), dimethyl suberimidate (DMS), dimethyl-3,3'-oxydipropionimidate (DODP), dimethyl-3,3'-(methylenedioxy)dipropionimidate (DMDP), dimethyl-,3'-(dimethylenedioxy)dipropionimidate (DDDP), dimethyl-3,3'-(tetramethylenedioxy)-dipropionimidate (DTDP), and dimethyl-3,3'-dithiobispropionimidate (DTBP).

Preferred, non-limiting examples of homobifunctional isothiocyanates include: p-phenylenediisothiocyanate (DITC), and 4,4'-diisothiocyano-2,2'-disulfonic acid stilbene (DIDS).

Preferred, non-limiting examples of homobifunctional isocyanates include xylene-diisocyanate, toluene-2,4-diisocyanate, toluene-2-isocyanate-4-isothiocyanate, 3methoxy-diphenylmethane-4,4'-diisocyanate, 2,2'-dicarboxy-4,4'-azophenyldiisocyanate, and hexamethylenediisocyanate.

Preferred, non-limiting examples of homobifunctional arylhalides include 1,5-difluoro-2,4-dinitrobenzene (DFDNB), and 4,4'-difluoro-3,3'-dinitrophenyl-sulfone.

Preferred, non-limiting examples of homobifunctional aliphatic aldehyde reagents include glyoxal, malondialdehyde, and glutaraldehyde.

Preferred, non-limiting examples of homobifunctional acylating reagents include nitrophenyl esters of dicarboxylic acids.

Preferred, non-limiting examples of homobifunctional aromatic sulfonyl chlorides include phenol-2,4-disulfonyl chloride, and .α.-naphthol-2,4-disulfonyl chloride.

Preferred, non-limiting examples of additional amino-reactive homobifunctional reagents include erythritolbiscarbonate which reacts with amines to give biscarbamates.

2. Homobifunctional Crosslinkers Reactive with Free Sulfhydryl Groups

Synthesis, properties, and applications of such reagents are described in the literature (for reviews of crosslinking procedures and reagents, see above). Many of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of homobifunctional maleimides include bismaleimidohexane (BMH), N,N'-(1,3-phenylene) bismaleimide, N,N'-(1,2-phenylene)bismaleimide, azophenyldimaleimide, and bis(N-maleimidomethyl) ether.

Preferred, non-limiting examples of homobifunctional pyridyl disulfides include 1,4-di->3'-(2'-pyridyldithio)propionamidobutane (DPDPB).

Preferred, non-limiting examples of homobifunctional alkyl halides include 2,2'-dicarboxy-4,4'-diiodoacetamidoazobenzene, α,α'-diiodo-p-xylenesulfonic acid, α, α'-dibromo-p-xylenesulfonic acid, N,N'-bis(b-bromoethyl)benzylamine, N,N'-di(bromoacetyl)phenylthydrazine, and 1,2-di(bromoacetyl)amino-3-phenylpropane.

3. Homobifunctional Photoactivatable Crosslinkers

Synthesis, properties, and applications of such reagents are described in the literature (for reviews of crosslinking procedures and reagents, see above). Some of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of homobifunctional photoactivatable crosslinker include bis-b-(4-azidosalicylamido)ethyldisulfide (BASED), di-N-(2-nitro-4-azidophenyl)-cystamine-S,S-dioxide (DNCO), and 4,4'-dithiobisphenylazide.

l. Hetero-Bifunctional Reagents

1. Amino-Reactive Hetero-Bifunctional Reagents with a Pyridyl Disulfide Moiety

Synthesis, properties, and applications of such reagents are described in the literature (for reviews of crosslinking procedures and reagents, see above). Many of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of hetero-bifunctional reagents with a pyridyl disulfide moiety and an amino-reactive NHS ester include N-succinimidyl-3-(2-pyridyldithio)propionate (SPDP), succinimidyl 6-3-(2-pyridyldithio)propionamidohexanoate (LC-SPDP), sulfosuccinimidyl 6-3-(2-pyridyldithio)propionamidohexanoate (sulfo-LCSPDP), 4-succinimidyloxycarbonyl-a-methyl-α-(2-pyridyldithio)toluene (SMPT), and sulfosuccinimidyl 6-a-methyl-α-(2-pyridyldithio)toluamidohexanoate (sulfo-LC-SMPT).

2. Amino-Reactive Hetero-Bifunctional Reagents with a Maleimide Moiety

Synthesis, properties, and applications of such reagents are described in the literature. Preferred, non-limiting examples of hetero-bifunctional reagents with a maleimide moiety and an amino-reactive NHS ester include succinimidyl maleimidylacetate (AMAS), succinimidyl 3-maleimidylpropionate (BMPS), N-γ-maleimidobutyryloxysuccinimide ester (GMBS)N-γ-maleimidobutyryloxysulfo succinimide ester (sulfo-GMBS) succinimidyl 6-maleimidylhexanoate (EMCS), succinimidyl 3-maleimidylbenzoate (SMB), m-maleimidobenzoyl-N-hydroxysuccinimide ester (MBS), m-maleimidobenzoyl-N-hydroxysulfosuccinimide ester (sulfo-MBS), succinimidyl 4-(N-maleimidomethyl)-cyclohexane-1-carboxylate (SMCC), sulfosuccinimidyl 4-(N-maleimidomethyl)cyclohexane-1-carboxylate (sulfo-SMCC), succinimidyl 4-(p-maleimidophenyl)butyrate (SMPB), and sulfosuccinimidyl 4-(p-maleimidophenyl)butyrate (sulfo-SMPB).

3. Amino-Reactive Hetero-Bifunctional Reagents with an Alkyl Halide Moiety

Synthesis, properties, and applications of such reagents are described in the literature Preferred, non-limiting examples of hetero-bifunctional reagents with an alkyl halide moiety and an amino-reactive NHS ester include N-succinimidyl-(4-iodoacetyl)aminobenzoate (SIAB), sulfosuccinimidyl-(4-iodoacetyl)aminobenzoate (sulfo-SIAB), succinimidyl-6-(iodoacetyl)aminohexanoate (SIAX), succinimidyl-6-(6-((iodoacetyl)-amino)hexanoylamino)hexanoate (SIAXX), succinimidyl-6-(((4-(iodoacetyl)-amino)methyl)-cyclohexane-1-carbonyl)aminohexanoate (SIACX), and succinimidyl-4((iodoacetyl)-amino)methyl-cyclohexane-1-carboxylate (SIAC).

A preferred example of a hetero-bifunctional reagent with an amino-reactive NHS ester and an alkyl dihalide moiety is N-hydroxysuccinimidyl 2,3-dibromopropionate (SDBP). SDBP introduces intramolecular crosslinks to the affinity component by conjugating its amino groups. The reactivity of the dibromopropionyl moiety for primary amino groups is defined by the reaction temperature (McKenzie et al., *Protein Chem.* 7: 581–592 (1988)).

Preferred, non-limiting examples of hetero-bifunctional reagents with an alkyl halide moiety and an amino-reactive p-nitrophenyl ester moiety include p-nitrophenyl iodoacetate (NPIA).

4. Photoactivatable Arylazide-Containing Hetero-Bifunctional Reagents with a NHS Ester Moiety Synthesis, properties, and applications of such reagents are described in the literature. Preferred, non-limiting examples of photoactivatable arylazide-containing heterobifunctional reagents with an amino-reactive NHS ester include N-hydroxysuccinimidyl-4-azidosalicylic acid (NHS-ASA), N-hydroxysulfosuccinimidyl-4-azidosalicylic acid (sulfo-NHS-ASA), sulfosuccinimidyl-(4-azidosalicylamido)hexanoate (sulfo-NHS-LC-ASA), N-hydroxysuccinimidyl N-(4-azidosalicyl)-6-aminocaproic acid (NHS-ASC), N-hydroxy-succinimidyl-4-azidobenzoate (HSAB), N-hydroxysulfo-succinimidyl-4-azidobenzoate (sulfo-HSAB), sulfosuccinimidyl-4-(p-azidophenyl)butyrate (sulfo-SAPB), N-5-azido-2-nitrobenzoyloxy-succinimide (ANB-NOS), N-succinimidyl-6-(4'-azido-2'-nitrophenyl-amino)hexanoate (SANPAH), sulfosuccinimidyl-6-(4'-azido-2'-nitrophenylamino)-hexanoate (sulfo-SANPAH), N-succinimidyl 2-(4-azidophenyl)dithioacetic acid (NHS-APDA), N-succinimidyl-(4-azidophenyl)1,3'-dithiopropionate (SADP), sulfosuccinimidyl-(4-azidophenyl)-1,3'-dithiopropionate (sulfo-SADP), sulfosuccinimidyl-2-(m-azido-o-nitrobenzamido)ethyl-1,3'-dithiopropionate (SAND), sulfosuccinimidyl-2-(p-azidosalicylamido)-ethyl-1,3'-dithiopropionate (SASD), N-hydroxysuccinimidyl 4-azidobenzoylglycyltyrosine (NHS-ABGT), sulfosuccinimidyl-2-(7-azido-4-4-methylcoumarin-3-acetamide)ethyl-1,3'-dithiopropionate (SAED), and sulfosuccinimidyl-7-azido-4-methylcoumarin-3-acetate (sulfo-SAMCA).

Other cross-linking agents are known to those of skill in the art (see, for example, Pomato et al., U.S. Pat. No. 5,965,106.

m. Linker Groups

In addition to the embodiments set forth above, wherein the cross-linking moiety is attached directly to a site on the mutant antibody and on the targeting moiety, the present invention also provides constructs in which the cross-linking moiety is bound to a site present on a linker group that is bound to either the mutant antibody or the targeting moiety or both.

In certain embodiments, it is advantageous to tether the mutant antibody and the targeting moiety by a group that provides flexibility and increases the distance between the mutant antibody and the targeting moiety. Using linker groups, the properties of the oligonucleotide adjacent to the stabilizing moiety can be modulated. Properties that are usefully controlled include, for example, hydrophobicity, hydrophilicity, surface-activity and the distance of the targeting moiety from the oligonucleotide.

In an exemplary embodiment, the linker serves to distance the mutant antibody from the targeting moiety. Linkers with this characteristic have several uses. For example, a targeting moiety held too closely to the mutant antibody may not interact with its complementary group, or it may interact with too low of an affinity. Similarly, a targeting moiety held to closely to the mutant antibody may prevent the antibody from binding the reactive chelate. Thus, it is within the scope of the present invention to utilize linker moieties to, inter alia, vary the distance between the mutant antibody and the targeting moiety.

In yet a further embodiment, the linker group is provided with a group that can be cleaved to release the mutant antibody from the targeting moiety. Many cleaveable groups are known in the art. See, for example, Jung et al., *Biochem. Biophys. Acta*, 761: 152–162 (1983); Joshi et al., *J. Biol. Chem.*, 265: 14518–14525 (1990); Zarling et al., *J. Immunol.*, 124: 913–920 (1980); Bouizar et al., *Eur. J. Biochem.*, 155: 141–147 (1986); Park et al., J. Biol. Chem., 261: 205–210 (1986); Browning et al., *J. Immunol.*, 143: 1859–1867 (1989). Moreover a broad range of cleavable, bifunctional (both homo- and hetero-bifunctional) linker groups are commercially available from suppliers such as Pierce.

Exemplary cleaveable moieties can be cleaved using light, heat or reagents such as thiols, hydroxylamine, bases, periodate and the like. Moreover, certain preferred groups are cleaved in vivo in response to their being endocytized (e.g., cis-aconityl; see, Shen et al., *Biochem. Biophys. Res. Commun.* 102: 1048 (1991)). Preferred cleaveable groups comprise a cleaveable moiety which is a member selected from the group consisting of disulfide, ester, imide, carbonate, nitrobenzyl, phenacyl and benzoin groups.

n. Fusion proteins

In a preferred form, the antibodies are recombinantly produced as fusion proteins with a second, antitumor antibody which acts to target the fusion protein to an antigen of a targeted tumor. Dozens of antitumor antigens and antibodies against them are known in the art, many of which are in clinical trials. Examples include AMD-Fab, LDP-02, aCD-11a, aCD-18, a-VEGF, a-IgE, and Herceptin, from Genentech, ABX-CBL, ABX-EGF, and ABX-IL8, from Abgenix, and aCD3, Smart 195 and Zenepax from Protein Design Labs. In preferred forms, the antibody is HMFG1, L6, or Lym-1, with Lym-1 being the most preferred. In preferred embodiments, an scFv or dsFv form of the antibody is employed. Formation of scFvs and dsFvs is known in the art. Formation of a scFv of Lym-1, for example, is taught Bin Song et al., *Biotechnol Appl Biochem* 28(2):163–7 (1998). See, also *Cancer Immunol. Immunother.* 43: 26–30 (1996). The two antibodies can be linked directly or, more commonly, are connected by a short peptide linker, such as $Gly_4Ser$, repeated 3 times.

2. The Chelates

In addition to the mutant antibodies described in detail above, the invention also provides reactive chelates that are specifically recognized by the antibody CDR and which form covalent bonds with the reactive group on the mutant antibody.

In practicing the present invention, the structure of the metal binding portion of the chelate is selected from an array of structures known to complex metal ions. Exemplary chelating agents of use in the present invention include but are not limited to, reactive chelating groups capable of chelating radionuclides these groups include macrocycles, linear moities or branched moieties. Examples of macrocyclic chelating moieties include polyaza- and polyoxamacrocycles. Examples of polyazamacrocyclic moieties include those derived from compounds such as 1,4,7,10-tetraazacyclododecane-N,N',N'',N'''-tetraacetic acid ("DOTA"); 1,4,7,10-tetraazacyclotridecane-N,N',N'',N'''-tetraacetic acid ("TRITA"); 1,4,8,11-tetraazacyclotetradecane-N,N',N'',N'''-tetraacetic acid ("TETA"); and 1,5,9,13-tetraazacyclohexadecane-N,N',N'',N'''-tetraacetic acid herein abbreviated as HETA). Examples of linear or branched chelating moieties include those derived from compounds such as ethylenediaminetetraacetic acid ("EDTA") and diethylenetriaminepentaacetic acid ("DTPA").

Chelating moieties having carboxylic acid groups, such as DOTA, TRITA, HETA, HEXA, EDTA, and DTPA, may be derivatized to convert one or more carboxylic acid groups to reactive groups. Alternatively, a methylene group adjacent to an amine or a carboxylic acid group can be derivatized with a reactive functional group. Additional exemplary chelates of use in the present invention are set forth in Meares et al., U.S. Pat. No. 5,958,374.

Figure 5:
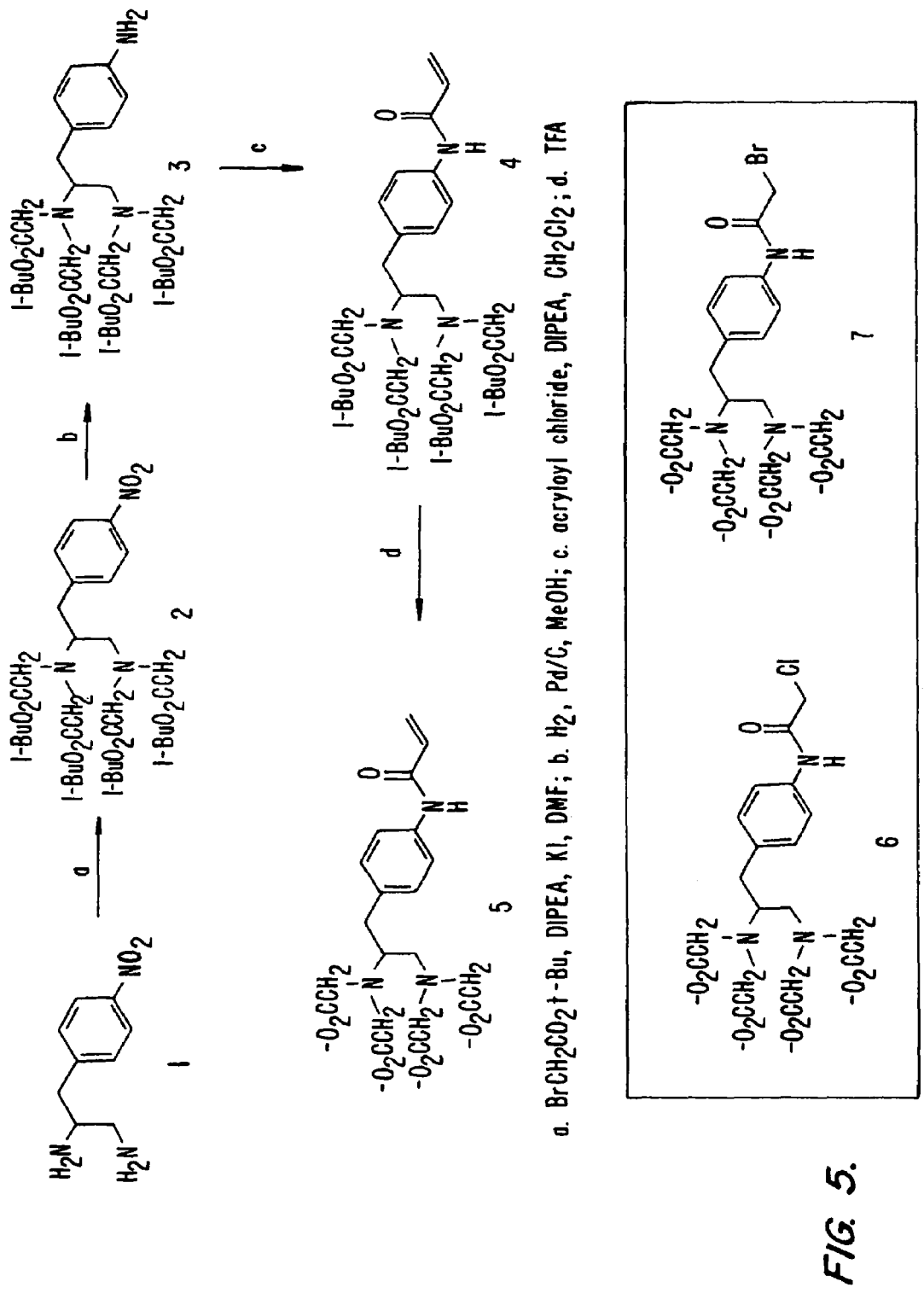
FIG. 5 is a synthetic scheme providing exemplary reactive chelates.

In a preferred embodiment of the invention, a reactive derivative of EDTA is used. Presently preferred EDTA derivatives are set forth in FIG. 5. A presently preferred EDTA derivative is compound 5.

The preparation of chelates useful in practicing the present invention is accomplished using art-recognized methodologies or modifications thereof. For example, referring to FIG. 5, ethylenediamine-derivative 1 is exhaustively alkylated with an agent such as a t-butyl protected acetyl halide to form compound 2. The nitro group of compound 2 is reduced to the corresponding amine 3. The amine is acylated with a reactive acylating moiety, such as acryloyl chloride to form compound 4. Compound 4 is subsequently deprotected to form chelate 5, which is metalated with the desired metal ion.

The chelate that is linked to the antibody or growth factor targeting agent will, of course, depend on the ultimate application of the invention. Where the aim is to provide an image of the tumor, one will desire to use a diagnostic agent that is detectable upon imaging, such as a paramagnetic, radioactive or fluorogenic agent. Many diagnostic agents are known in the art to be useful for imaging purposes, as are methods for their attachment to antibodies (see, e.g., U.S. Pat. Nos. 5,021,236 and 4,472,509, both incorporated herein by reference). In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred. Ions useful in other contexts, such as X-ray imaging, include but are not limited to lanthanum (III), gold (III), lead (II), and especially bismuth (III). Moreover, in the case of radioactive isotopes for therapeutic and/or diagnostic application, presently preferred isotopes include iodine$^{131}$, iodine$^{123}$, technicium$^{99m}$, indium$^{111}$, rhenium$^{188}$, rhenium$^{186}$, gallium$^{67}$, copper$^{67}$, yttrium$^{90}$, iodine$^{125}$ or astatine$^{211}$.

Antibody-Chelate Bond Formation

In general, after the formation of the antibody-antigen (chelate) complex, the reactive chelate and mutant antibody of the invention are linked together through the use of reactive groups, which are typically transformed by the linking process into a new organic functional group or unreactive species. The chelate reactive functional group(s) is located at any position on the metal chelate. Reactive groups and classes of reactions useful in practicing the present invention are generally those that are well known in the art of bioconjugate chemistry. Currently favored classes of reactions available with reactive chelates are those which proceed under relatively mild conditions. These include, but are not limited to, nucleophilic substitutions (e.g., reactions of amines and alcohols with acyl halides, active esters), electrophilic substitutions (e.g., enamine reactions) and additions to carbon—carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Useful reactive pendant functional groups include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups, which can be converted to, e.g., esters, ethers, aldehydes, etc.

(c) haloalkyl groups, wherein the halide can be later displaced with a nucleophilic group such as, for example, an amine, a carboxylate anion, thiol anion, carbanion, or an alkoxide ion, thereby resulting in the covalent attachment of a new group at the functional group of the halogen atom;

(d) dienophile groups, which are capable of participating in Diels-Alder reactions such as, for example, maleimido groups;

(e) aldehyde or ketone groups, such that subsequent derivatization is possible via formation of carbonyl derivatives for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be, for example, converted to disulfides or reacted with acyl halides;

(h) amine or sulfhydryl groups, which can be, for example, acylated, alkylated or oxidized;

(i) alkenes, which can undergo, for example, cycloadditions, acylation, Michael addition, etc; and (j) epoxides, which can react with, for example, amines and hydroxyl compounds.

The reactive functional groups can be chosen such that they do not participate in, or interfere with, the reactions necessary to assemble the reactive chelates. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

B. The Methods

In addition to the compositions of the invention, the present invention provides methods for using the compositions. Thus, in a third aspect, the invention provides a method of using the compositions of the invention to treat a patient for a disease or condition or to diagnose a condition or disease. The method comprising the steps of: (a) administering to the patient a mutant antibody comprising; (i) a complementarity-determining region that specifically binds to the metal chelate; (ii) a reactive site not present in the wild-type of the antibody and, wherein the reactive site is in a position proximate to or within the complementarity-determining region; and (iii) a targeting moiety that binds specifically to a cell by binding with a surface group (e.g., cell surface receptors and cell surface antigens), thereby forming a complex between the mutant antibody and the cell. Following step (a), the metal chelate is administered to the patient. The metal chelate comprises a reactive functional group having a reactivity complementary to the reactivity of the reactive site of said antibody. Thus, the chelate and the antibody bind to form an antibody-antigen (chelate) pair, the reactive groups of which subsequently react to form a covalent bond between the antibody and the antigen. As discussed above, the techniques relevant to raising antibodies and preparing chelates useful in the above-recited method are well known in the art.

The present invention provides antibodies raised against essentially any chelate of any metal ion. In a preferred embodiment, the antibody used for pretargeting is CHA255, a monoclonal antibody which recognizes an indium chelate.

In addition to the method described above, the present invention provides a method in which the tissue is pretargeted with a pretargeting reagent which is recognized and bound by a the targeting moiety on the antibody of the invention. This pretargeting method of treating a patient with a metal chelate comprises the steps of: (a) administering a pretargeting reagent to the patient and; (b) following step (a), administering to said patient a mutant antibody of the invention.

The mutant antibody comprises: (i) a complementarity-determining region that specifically binds to the metal chelate; (ii) a reactive site not present in the wild-type of the antibody (the reactive site is in a position proximate to or within the complementarity-determining region); and (iii) a recognition moiety that binds specifically with the pretargeting reagent, thereby forming a complex between the pretargeting reagent and the mutant antibody. After the pretargeting reagent has localized in the desired tissue, following step (b), a metal chelate is administered to the patient. The chelate specifically binds to the mutant antibody of the invention, forming an antibody-antigen complex. Moreover, the chelate comprises a reactive functional group having a reactivity. After the antibody-antigen complex is formed, the reactive site of the antibody and that of the metal chelate react to form a covalent bond between the mutant antibody and the metal chelate.

Pretargeting methods have been developed to increase the target:background ratios of the detection or therapeutic agents. Examples of pre-targeting and biotin/avidin approaches are described, for example, in Goodwin et al., U.S. Pat. No. 4,863,713; Goodwin et al., *J. Nucl. Med.* 29: 226 (1988); Hnatowich et al., *J. Nucl. Med.* 28: 1294 (1987); Oehr et al., *J. Nucl. Med.* 29: 728 (1988); Klibanov et al., *J. Nucl. Med.* 29: 1951 (1988); Sinitsyn et al., *J. Nucl. Med.* 30: 66 (1989); Kalofonos et al., *J. Nucl. Med.* 31: 1791 (1990); Schechter et al., Int. J. Cancer 48:167 (1991); Paganelli et al., *Cancer Res.* 51:5960 (1991); Paganelli et al., *Nucl. Med. Commun.* 12: 211 (1991); Stickney et al., *Cancer Res.* 51: 6650 (1991); and Yuan et al., *Cancer Res.* 51:3119, 1991; all of which are incorporated by reference herein in their entirety.

In both of the above-described aspects of the invention, it is preferable that a significant proportion of the antibodies used remain on the cell surface to be accessible to a later introduced moiety containing the radioactive agent. Thus, it is generally preferable to choose antigens which are not rapidly endocytosed or otherwise internalized by the cell upon antibody binding. Preferably, at least one-quarter of the bound antibody should remain on the cell surface and not become internalized. In some cases, however, even less of the bound antibody may remain on the cell surface. For example, for a particular tumor type, an antigen which has a high rate of internalization may still be used for pretargeting if there is no known antigen with a lower internalization rate (or for which an antibody is available) with which to image tumor locations. The suitability of a particular antigen can be determined by simple assays known in the art.

1. Clearing Agents

Clearing agents known in the art may be used in accordance with the present invention. In a preferred embodiment, the clearing agent is an antibody which binds the binding site of the targeting species, where the targeting species can be an antibody, an antigen binding antibody fragment or a non-antibody targeting species. In a more preferred embodiment, the clearing agent is a MAb that is anti-idiotypic to the MAb of the conjugate used in the first step, as described in U.S. application Ser. No. 08/486,166. In another preferred embodiment, the clearing agent is substituted with multiple residues of carbohydrate, such as galactose, which allow the clearing agent to be cleared quickly from circulation by asialoglycoprotein receptors in the liver.

In a more preferred embodiment, the clearing agent is an anti-idiotypic MAb substituted with galactose and small numbers of biotin residues. Different purposes are being accomplished here. The anti-idiotypic MAb clears the first antibody conjugate (radioiodinated MAb-SAv) from circulation and deposits this into the hepatocytes. Because the anti-idiotypic MAb binds to the Mab binding region of the first antibody, it does not remove first antibody conjugate already localized at the tumor sites.

The multiple galactose substitution ensures the rapid clearance of the anti-idiotypic MAb into the liver hepatocytes, usually within minutes. Because the anti-idiotypic MAb is galactosylated and cleared rapidly, it does not have a chance to competitively remove the tumor-localized first antibody conjugate from the tumor over time. Also, there is very little myelotoxicity since almost all circulating radioactivity has been removed from the blood.

The materials, methods and devices of the present invention are further illustrated by the examples which follow. These examples are offered to illustrate, but not to limit the claimed invention.

EXAMPLES

Example 1 sets forth the synthesis of an exemplary reactive chelate. Example 2 sets forth the method for determining the non-reactivity of the chelates in the absence of the mutant antibodies. Example 3 sets forth the use of rational computer-aided design to develop an indium-EDTA chelate to covalently bind to monoclonal antibody CHA255 in vivo. Example 4 demonstrates that a covalent bond is formed between an exemplary antibody of the invention and a reactive chelate that is specifically recognized by the antibody.

Example 1

Synthesis of EDTA chelates

The approach used to prepare the reactive EDTA derivatives is generally that disclosed in Studer and Meares, *Bioconjugate Chemistry* 3:420–423 (1992).

1.1. (S)-1-p-(Nitrobenzyl)ethylenediamine ("Nitrobenzyl-en") 1

Compound 1 was synthesized according to DeRiemer et al. (DeRiemer et al., *J. Labelled Compds. Radiopharm.* 18: 1517–1534 (1981)).

1.2. Preparation of Nitrobenzyl-EDTA tetra-t-butyl ester 2

To nitrobenzyl-en dihydrochloride 1 (1.76 g, 6.56 mmol), suspended in 50 ML of dry $CH_3CN$, $K_2CO_3$ (4.66 g, 33.5 mmol) and KI (1.12 g, 6.75 mmol) were added. While stirring, $BrCH_2COOC(CH_3)_3$ (5.50 mL, 34.0 mmol) was added, the reaction mixture was refluxed for 120 h in the dark. The mixture was evaporated to dryness, and, after treating it with 20 mL $CHCl_3$, filtered through a glass frit (4.5 cm diameter, containing 2 cm of silica gel). The frit was washed with 500 mL $CHCl_3$. The volume of the filtrate was reduced to 10 mL. The purification was carried out on an open silica gel column (35×3.5 cm) eluted with $CHCl_3$. The fractions containing pure product (TLC $R_f$ 0.3, $CHCl_3$/ethyl acetate 10:1) were collected and dried to give the yellow oil 2. (2.50 g, 3.84 mmol, 58%). $^1H$ NMR ($CDCl_3$): 1.20–1.50 (m, 36H), 2.40 (m, 1H), 2.80–3.50 (m 12H), 7.40 (d, 2H), 8.05 (d, 2H); MS m/e for $C_{33}H_{53}N_3O_{10}$ (M+H$^+$) 652.

1.3. Preparation of Aminobenzyl-EDTA tetra-t-butyl ester 3

Compound 2 (110 mg, 0.169 mmol) was dissolved in 3 mL of dry tetrahydrofuran (THF), $K_2CO_3$ (30 mg, 0.217 mmol) and 10% palladium on charcoal (30 mg) were added. The reaction vessel was attached to an atmospheric-pressure hydrogenation apparatus. The mixture was purged with $N_2$, then filled with $H_2$, and the reaction was stirred at 25° C. The course of the reaction was monitored by the $H_2$ uptake. After 20 h, the solution was filtered through a glass frit (as for 2). The frit was washed with 100 mL THF. The filtrate, positive to a test for primary amines using fluorescamine, was evaporated to dryness to give 3 (70 mg, 0.113 mmol, 67%, TLC $R_f$ 0.3, $CHCl_3$/ethyl acetate 3:1). $^1H$ NMR ($CDCl_3$): 1.35–1.50 (m, 36), 2.40–2.60 (m, 2H), 2.70–2.85 (m, 2H), 3.05 (m, 1H), 3.40–3.50 (m, 8H), 6.55 (d 2H), 6.95 (d, 2H). MS m/e for $C_{33}H_{55}N_3O_8$ (M+H+) 622.

1.4 Preparation of Acrylamidobenzyl-EDTA ("AABE") 4

Amine 3 was alkylated with acryloyl chloride in methylene chloride to provide the t-butyl protected AABE moiety, which after deprotection in neat TFA gave the full functional AABE chelate.

Specifically 0.1 g of 3 (621 g/mol, 0.16 mmol) was added to a 100 mL three neck round bottom flask and dissolved in 5 mL of a methylene chloride. The flask was fitted with two addition funnels and an argon gas inlet at the center port. To each addition funnel was added 5 mL of methylene chloride. To one of the funnels was added additionally 16 mg (1.4 equivalents, 0.225 mmol) of acryloyl chloride (74.5 g/mol) and to the other funnel was added 2equivalents of diisopropylethylamine (41 g, 54 UL). Under mechanical stirring with a teflon magnetic stir bar and plate, the reactants in each addition funnel were added simultaneously over approx. 20 minutes. After addition, the reaction was allowed to stir for an additional 30 minutes. The completed reaction mixture was applied neat to a 4"×12" silica gel column equilibrated with 3:1 hexane: EtOAc: 0.5% triethylamine. The material was eluted using air pressure (flash chromatography) and 12 ml fractions were collected. Fractions were spotted onto a fluorescent TLC plate and developed using the above-described solvent mixture. Fractions containing the UV absorbing fraction (generally 5–20) were pooled and rotovaporated to dryness to yield a yellow oil, 0.107 g, 99% yield. The product was characterized by NMR ($^1H$ and $^{13}C$).

1.5 Deprotection of t-butyl AABE, 5

Compound 4 was deprotected by contacting it with neat peptide-grade trifluoroacetic acid. For example 50 mg of t-butyl-AABE was added to a acid washed 20 ml pear bottom flask. Neat TFA (10 mL) was added and the mixture was stirred with a magnetic stirr bar for 14 hrs under a light flow of Ar(g). TFA was removed by rotoevaporation to yield a yellow oil. The product was characterized by reversephase HPLC, NMR, mass spectrometry and quantitative metal binding assay.

1.6 Preparation of Compounds 6, and 7

Reactive EDTA chelates 6 (chloroacetylamidobenzyl, "CABE"), and 7 (bromoacetylamidobenzyl, "BABE") were prepared in a manner analagous to that set forth above, using appropiate acid chlorides.

Example 2

To determine to non-reactivity of the chelates in the absence of the mutant antibodies, they were injected into Balb/C mice and the amount of residual reactivity was quantitated.

2.1 Formation of the Metal Chelates

The chelating agents BABE, CABE, CpABE, AABE and ABE were dissolved in water (18 ohm) generally at a concentration of about 20–40 mM, which was determined exactly by quantitative metal binding assay. 1 µl of chelate was added to 9 µl of 0.1 M citrate buffer (pH 5.5), to which was added 1 µl of carrier free $^{111}$ In. This solution was mixed and allowed to incubate for 1 h at room temperature. Complete chelation was determined by TLC analysis of the metallation reaction. 1 µl of reaction was applied to a silica TLC plate which was developed in a buffer of 1:1 MeOH: 10% NaOAc. Free metal remained at the origin while chelated metal migrated with the solvent. After visualization by autoradioagraphy of the TLC plate, approximately 99% chelation of the metal was shown. To all chelates after metallation was added 1 µl of 0.1 M $CaCl_2$ (to fill all chelation sites and minimize deliterious chelation of calcium in vivo, which ultimately causes cardiac arrest in the mice).

2.2 Stability of Bifunctional In Chelates

The electrophilic chelates AABE, CABE, BABE were labeled with indium-111 and incubated in a Hepes buffered solution at physiological pH and temperature (20 mM Hepes, pH 7.4, 37° C.) containing 1 mM free sulfhydryl groups in the form of human serum albumin-approximating the concentration of thiols in plasma.

The reactive chelates 5–7 and aminobenzyl-EDTA ("ABE") were labeled with $^{111}$In and analyzed by TLC (50:50 Methanol/10% NaOAc pH8.2) to show complete chelation. To 0.5 mL of human serum albumin solution was added 2 µl of one of the labeled chelates. The final solutions had a sulfhydryl group concentration of 1 mM and a chelate concentration of 40 µM. The vials were mixed by manual agitation, and 2 µl was removed and analyzed by TLC.

Figure 6:
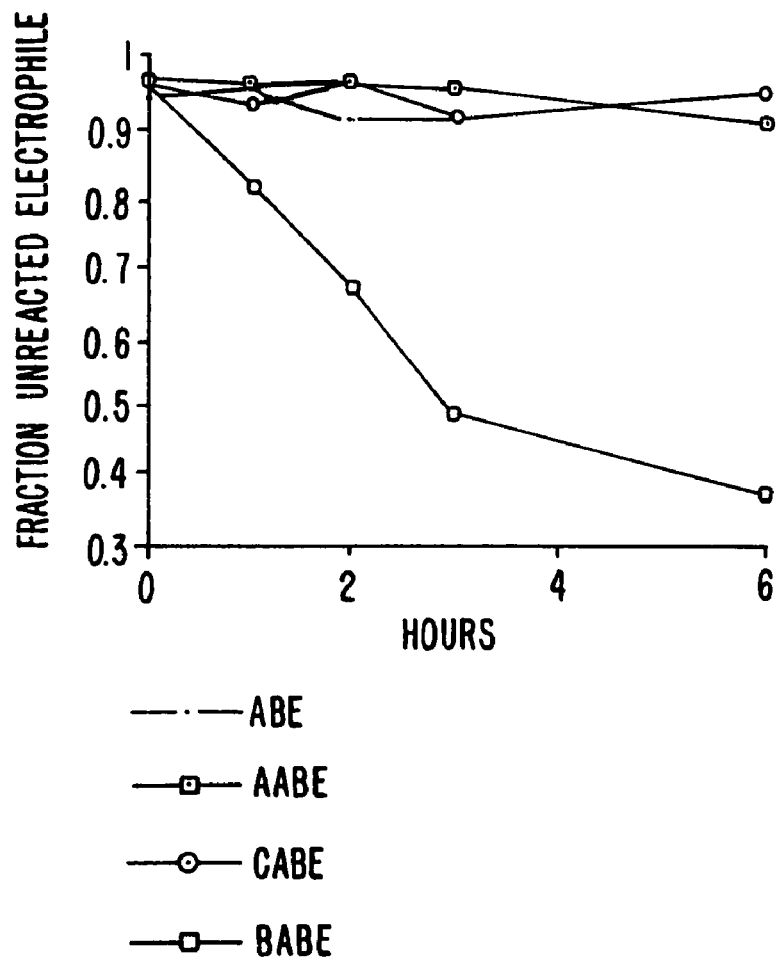
FIG. 6 is a graphical display of the reactivity towards human serum albumin of exemplary reactive chelates.

The fraction unreacted is plotted versus incubation time in FIG. 6. After 20 hrs, >95% of the In-AABE and In-CABE molecules were unreacted, while most of the In-BABE was attached to albumin. This confirmed the expectation that AABE and CABE are stable, and are good candidates for pretargeting. We infer that these chelates should be unreactive in blood for the length of time needed for pretargeting (40 min–4 hrs); if not, many other choices are available.

As a control, the same chelates were incubated with native antibody CHA255, to see if they would covalently label it. The indium-ABE, -AABE, and -CABE chelates did not covalently attach to CHA255, while the BABE chelate did react to some degree after several hours.

2.3 In vivo Clearance of the Metal Chelates

Figure 7:
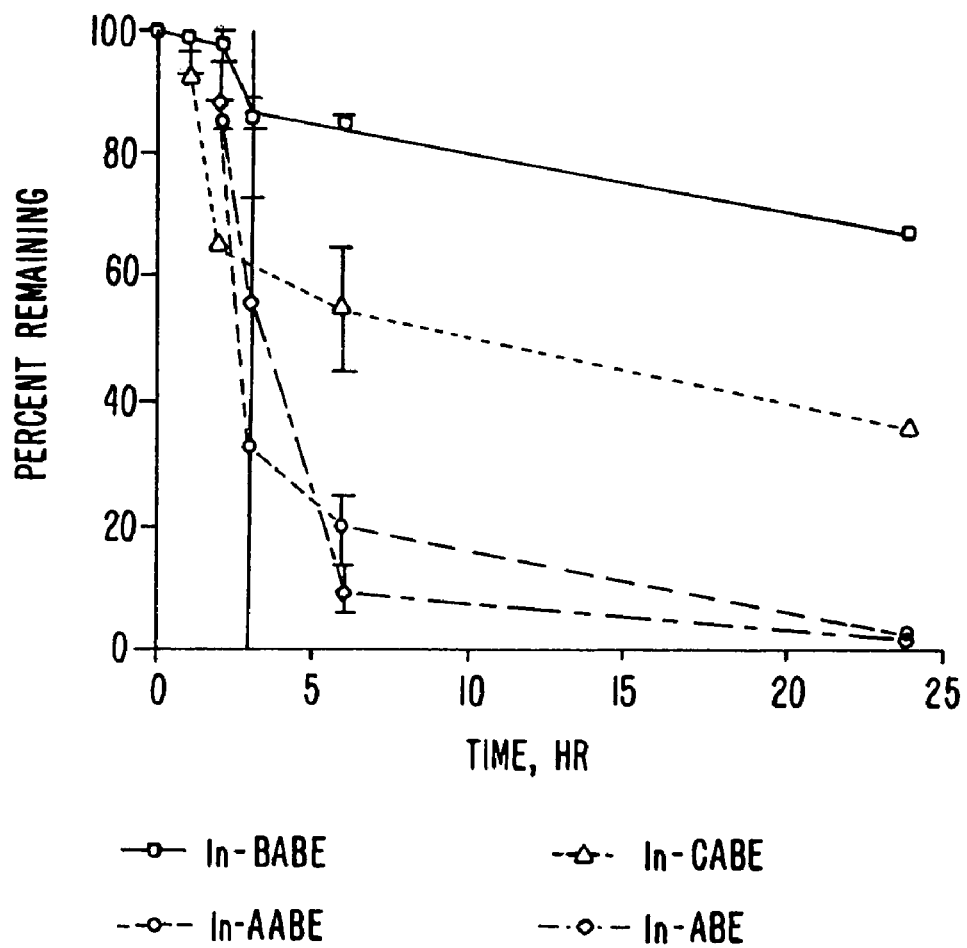
FIG. 7 is a graphical display of the whole-body clearance in the rate vs. time of exemplary reactive chelates.

The chelates described in 4.1, above, were dilluted into normal saline to a concentration of 20 µCi/200 µL and injected IV into the tail vein. Three animals per chelate were injected and the residual reactivity present in the animal was quantitated by gamma counting the whole animal at 0,1,2, 3,6 and 24 h post injection. Counts were decay corrected and total counts over time were plotted to show the clearance of each chelate (FIG. 7).

Example 3

This Example shows the use of rational computer-aided design to develop an indium-EDTA chelate to covalently bind to monoclonal antibody CHA255 in vivo. The premise is to allow the chelate to bind non-covalently to CHA255 bound to a tumor and then to covalently attach the chelate to the antibody, thereby trapping it at the tumor site. This involves cloning the variable domains of anti-In-EDTA monoclonal antibody CHA255, to construct a human/mouse chimeric Fab fragment that can be expressed in *E. coli*, and the synthesis and screening of benzyl-EDTA chelates carrying weakly electrophilic groups capable of conjugation to the antibody in vivo. This Fab can be conjugated to a targeting moiety when desired.

3.1. Antibody Design

Using molecular modeling software (InsightII, Biosym/MSI) and the crystal structure of CHA255 bound to its hapten (Love, R. et al., *Biochemistry* 32:10950–10959 (1993)), a scheme was developed for Michael addition to occur between an engineered cysteine residue in CHA255 and an (S)-p-acrylamidobenzyl-EDTA-In chelate. By design, this reaction occurs between a cysteine residue in the antibody positioned near the tail of the chelate and the acryl group. Serine 95 of the light chain was chosen because its close proximity and orientation to the bound acryl group permits a cysteine placed at that position to react with the acryl group, while the serine residue was not involved with the hydrophobic interactions or hydrogen bonding between the antibody and its target. The high local concentration of reactive groups, caused by the chelate binding to the antibody fragment, favors reaction of the cysteine with the weak electrophile. More reactive electrophiles such as iodo- on bromoacetamide are not used, so that the chelate will have low cross-reactivity with nucleophiles in the circulation (albumin, cysteine, glutathione, etc.). The synthetic scheme is also flexible: other reactive chelates can be developed to conjugate in vivo. For example, (S)-p-chloroacetamidobenzyl-EDTA-In fits in the binding pocket and can conjugate with the cysteine residue by an $S_n2$ reaction.

3.2. Cloning of CHA255

CHA255 hybridoma cells were grown in RPMI 1640 supplemented with 110% FCS and used as a source of genetic template. Messenger RNA was extracted with the Oligotex Direct mRNA Extraction kit (Qiagen). Complementary DNA synthesis and PCR amplification of the variable domain genes were done using the Ig Prime kit (Novagen) and ligated into pT7Blue as per manufactures protocol. Site directed substitution of cysteine at positions 95 (S95C) and 96 (N96C) of the light chain was done via the method of Ito (Ito et al., *Gene* 102, 67–70 (1991)) using the T7 and U19 primers of the pT7 vector system and the primer KxbaI (CTGCAGGTCGACTGTAGAGGATCTACTAGT) and the mutagenesis primers S95C (ATACCCAGAGGTTG-CAGTACCATAGAGCAC) and N96C (ATACCCAGAG-GCAGCTGTACCATAGAGCAC). Thus, plasmids pTV1S95CCha255 and pTV1N96CCha255 encoding the variable light chain domains of CHA255 with the mutations at positions 95 and 96 were produced (FIG. 1). For expression of Fab molecules chimeric constructs containing the variable regions of CHA255 with the constant regions of human anti-tetanus toxoid were constructed in a two step overlap extension methodology from the vectors pTVH-Cha255, pTVlCha255, pTVlS95CCha255, pTVlN96CCha255 and npC3tt. The primers used to amplify the full chimeric gene contained BglII and XbaI restriction sites for introduction into the expression cassette of pMT/Bip/V5His version B.(Invitrogen) for expression of the chimeric Fab molecules in *Drosophila* S2 cells. The resulting plasmids pMTBipVlCha/tt, pMTBipVlS95CCha/tt, pMTBipVlN96CCha/tt, encoding the native and mutant chimeric light chain domains and pMTBipVHCha/tt/V5His encoding the chimeric heavy chain domain were co-transfected in equal molar ratio into exponentially growing cultures of S2 cells (ATCC CRL-1963) using the calcium phosphate co-precipitation method and protein expression was induced by addition of $CUSO_4$ to a final concentration of 500 µM. For production of stable cell lines additional co-transfections with the selection vector pCohygro (Invitrogen) encoding the Hygromycin B phosphotransferase gene, followed by three to four weeks of selection with 300 µg/ml of hygromycin B in complete medium (FIG. 2 and FIG. 3).

NPC3tt, developed by Barbas and co-workers from pcomb3, (Gram et al., *Proceedings of the National Academy of Sciences (USA)* 89(8):3576–80 (1992) is a vector designed to express two polypeptide chains under control of the lac promoter for periplasmic expression with ompA and pelB leader sequences. It contains the Fab heavy and light domains of a human tetanus toxoid antibody. Sequential cloning of the CHA255 mouse variable heavy chains between the XhoI and ApaI sites followed by insertion of the variable light chain with S95C mutation between the SstI and BsiWI sites results in a human/mouse chimera (FIG. 4).

EXAMPLE 4

The present example demonstrates that an exemplary antibody of the invention covalently binds to a reactive chelate that is specifically recognized by the antibody.

4.1 Methods

100 µl of complete culture medium from S2 cultures expressing each of the CHA255 Chimeric Fabs was mixed with 5 µl of 100 mM DOTA to sequester $Cu^{2+}$ from induction of expression. Each chelate was loaded with $^{111}$In as previously described with a specific activity of 200 µCi. Complete metallation was analyzed by TLC as described previously. Specifically, 1 µl of chelate was added to 2.8 µl of 0.1 M citrate buffer (pH 5.5) to which was added 1.2 µl of carrier free $^{111}$In (Nordion) (0.5 µl) and the chelate was analyzed by TLC. 4 µl of loaded chelate was added to the 105 µl of Fab-DOTA in medium. This solution was incubated for 30 min. at room temperature. The reaction was stopped by separation of excess chelate by gel filtration spin chromatography (Penefsky column). 20 µl of eluant was added to 5 µl of sample application buffer containing β-mercaptoethanol (5×SDS PAGE SAB), boiled and reduced for 10 min. at 95° C. This was loaded onto a 1020% SDS-Page gel and electrophoriesed for 1 hr at 200V. The gel was fixed and dried via standard protocols and then exposed to a phosphorimager plate for 12 h. The plate was visualized with a Storm 640 phosphorimager (Molecular Dymanics).

4.2 Results

By inspection of the crystal structure we chose to introduce our cysteine residues at positions 95 and 96 of the light chain variable domain. This area was chosen because it does not have any direct contacts with the bound chelate but lies within a few angstroms of the para position of the chelate in the complex. We cloned the variable domains of anti-chelate antibody CHA255 from mRNA prepared from the parent hybridoma and introduced cysteines at the prescribed locations by site-directed mutagenesis. We then attached the variable domains to the $CH_l$ and $C_k$ constant domains of the human tetanus toxoid antibody to produce a mouse/human chimeric Fab. This was accomplished via a two-step PCR synthesis in which the full gene from plasmids containing the respective template genes was placed directly into expression vectors behind a BIP leader sequence (this sequence specifies export into the culture medium). Thus we produced four plasmids containing chimerized Fab genes for the native heavy variable domain, the native light domain and the mutant light domains S95C and N96C.

Figure 16:
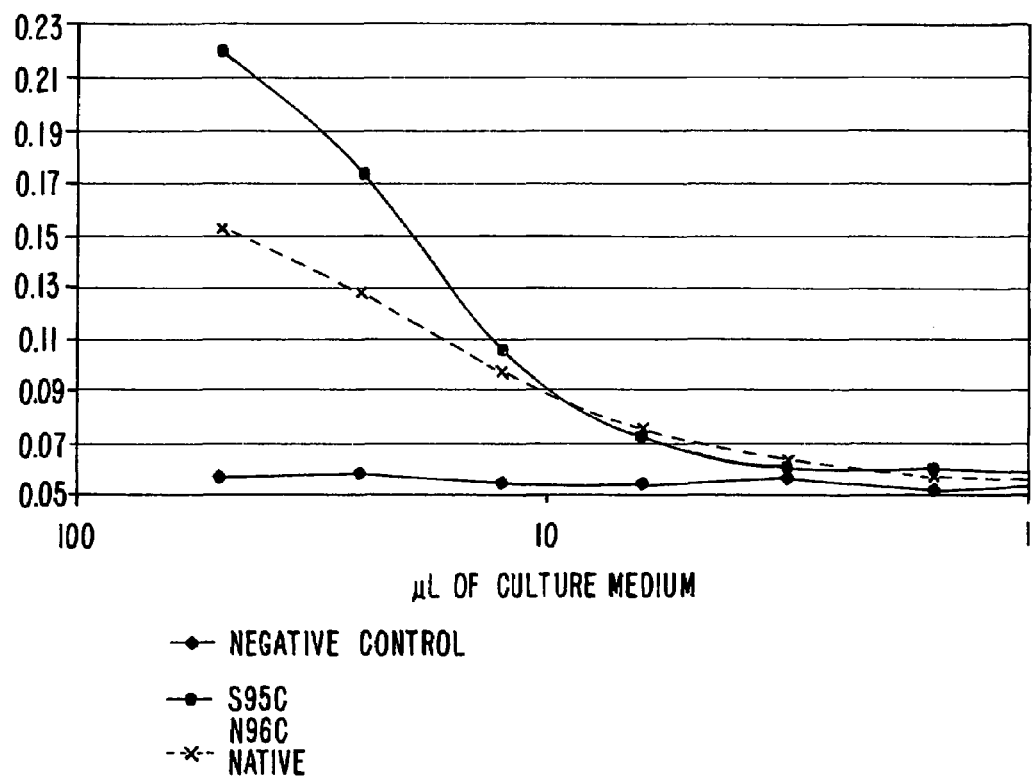
FIG. 16 is a Western Blot of CHA255 chimeric Fab, A: S95C, B: N96C, C: native.
Figure 17:
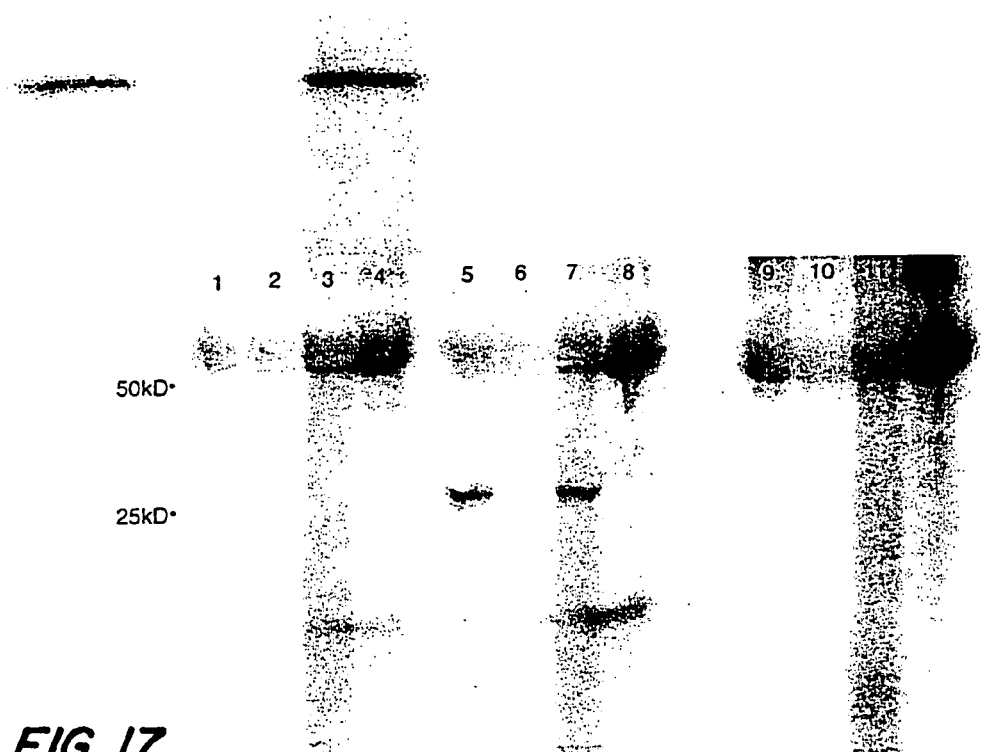
FIG. 17 is a display of an ELISA analysis of CHA255 chimeric Fab mutants in culture medium.

The three mutant Fabs, the native chimeric (ATCC Deposit No. PTA-4696, made Sep. 19, 2002, at the ATCC, 10801 University Blvd. Manassas, Va. 20110-2209), the S95C mutant and the N96C mutant, were expressed by cotransfection in S2 cells of the plasmid bearing the heavy chain with a plasmid carrying one of the three differing light chains. Culture medium of each of the respective Fab expressing cell lines was analyzed by reducing SDS-PAGE followed by Western blotting with immunostaining via the C-terminal epitope tag present on the heavy chain (FIG. 16). This staining process shows a band at 26 kD as expected. ELISA analysis of the culture medium samples with indium benzyl-EDTA-HSA conjugate coated plates demonstrated that all chimeric Fabs bound the hapten in a concentration dependent manner (FIG. 17).

In-labeled electrophilic chelates were incubated in Fab-containing culture medium to investigate whether either of the mutant antibodies would bind irreversibly to its target. Serum-containing culture medium was used as a representation of typical biological media. The specific covalent attachment of an $^{111}$In-chelate to a mutant Fab—but not to the native Fab or to other molecules such as albumin present in the medium—shows the potential value of this procedure. We incubated $^{111}$In-labeled chelates bearing electrophilic acrylamido, chloroproprionamido, or chloroacetamido groups at physiological pH and temperature with raw tissue culture medium from the cells expressing the recombinant antibodies. As a control, an $^{111}$In-labeled chelate bearing the non-electrophilic amino group was also included. At various times after addition of the radioactive chelates, we removed samples from the incubation and applied them to a gel filtration spin column to remove excess radiolabeled chelate.

Figure 18:
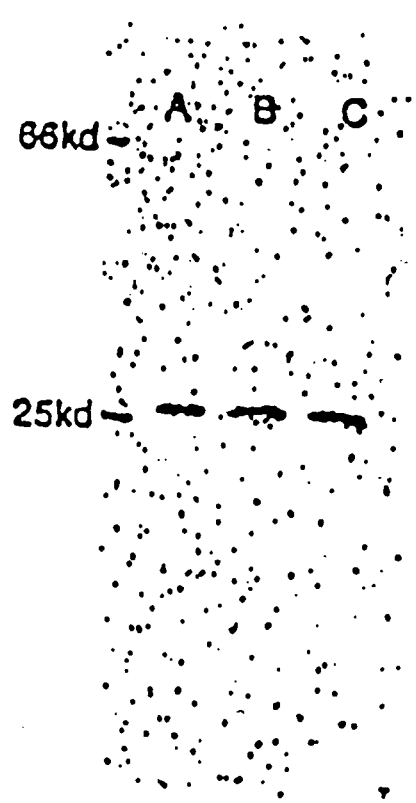
FIG. 18 is a phosphorimage of a 15% SDS-PAGE gel of samples incubated 30 minutes at 37° C. Chelates (CABE, CpABE, AABE, ABE) are in lanes 1–4, along with culture medium containing the S95C mutant. The (radiolabeled) band (at 26 kDa) in lane 1 is the crosslink between CABE (our positive control) and S95C Fab light chain. Lane 2 shows a weak signal at the same relative migration caused by the cross-linking of CpABE with S95C. Lane 3 shows the 26 kDa band caused by cross-linking of AABE with S95C. Lane 4 does not show crosslinks, as expected for the non-electrophilic chelate ABE incubated with S95C. No crosslinks are observed with the non-nucleophilic native Fab, nor with the N96C mutant.

The samples were analyzed by SDS-PAGE and visualized by phosphorimager. Separation under reducing and denaturing conditions on SDS-PAGE will separate the light chain from the heavy chain of each Fab, functionally destroying the antibody-binding pocket. If chelates are bound to the Fab but not covalently linked, they dissociate because the antibody-binding pocket holding them together is no longer folded. Unbound chelate does not migrate with the antibody chains. However, chelate which bound to a Fab and then covalently linked, will be attached to the Fab light chain and migrate with it on SDS-PAGE. This result was observed with the Fab S95C (ATCC Deposit No. PTA-4695, made Sep. 19, 2002 at the ATCC, 10801 University Blvd. Manassas, Va. 20110-2209)(FIG. 18).

As expected nucleophilic Fab S95C reacted equally well with the strongly electrophilic $^{111}$In-CABE chelate and with the weakly electrophilic In-AABE chelate. The mechanism of each is different in that the reaction with $^{111}$In-CABE is an $S_n2$ displacement while the reaction with AABE is a 1,4 addition (Michael Addition). The non-nucleophilic Native Fab does not cross-link with any of the electrophilic chelates.

It is understood that the examples and embodiments described herein are for illustrative purposes only and that various modifications or changes in light thereof will be suggested to persons skilled in the art and are included within the spirit and purview of this application and are considered within the scope of the appended claims. All publications, patents, and patent applications cited herein are hereby incorporated by reference in their entirety for all purposes.

What is claimed is:

1. A mutant antibody comprising a reactive site not present in the wild-type of said antibody and six complementarity determining regions (CDRs) that recognize a metal chelate or portions thereof, wherein said reactive site is in a position proximate to or within said complementarity-determining regions,
   wherein said reactive site is the mutation and,
   wherein said reactive site interacts with a reactive group on said metal chelate and said reactive group is selected from carboxyl groups, hydroxyl groups, haloalkyl groups, dienophile groups, aldehyde groups, ketone groups, sulfonyl halide groups, thiol groups, amine groups, sulfhydryl groups, alkene groups, and epoxide groups.

2. The mutant antibody according to claim 1, wherein said reactive site is a side-chain of a naturally occurring or non-naturally occurring amino acid.

3. The mutant antibody according to claim 2, wherein said reactive site is the —SH group of cysteine.

4. A polypeptide comprising a peptide sequence according to SEQ. ID NO.:5 (FIG. 12).

5. A polypeptide comprising a peptide sequence according to SEQ. ID NO.: 7 (FIG. 14).

6. The mutant antibody according to claim 1, wherein said mutant antibody is a mutant of the antibody deposited as ATCC Deposit No. PTA-4696.

7. The mutant antibody according to claim 6, wherein serine-95 of the light-chain is substituted by a cysteine residue is the mutation.

8. The mutant antibody according to claim 1, wherein said antibody is a bifunctional antibody further comprising a second complementarity-determining region that specifically binds to a cell-surface antigen.

9. The mutant antibody according to claim 1, further comprising a targeting moiety covalently attached thereto, wherein the targeting moiety and the mutant antibody are not the same.

10. The mutant antibody according to claim 9, having the structure:
   Ab L T
   wherein,
   Ab represents said antibody;
   L is a chemical bond or linking group; and
   T is said targeting moiety.

11. The mutant antibody according to claim 9, wherein said targeting moiety is an antibody that binds specifically to a cell surface antigen.

12. The mutant antibody according to claim 1, further comprising said metal chelate bound to said complementarity-determining region, wherein said chelate comprises a reactive functional group of complementary reactivity to said reactive site of said antibody.

13. The mutant antibody according to claim 12, further comprising a covalent bond formed by reaction of said reactive site of said antibody and said reactive functional group of said chelate, wherein said covalent bond is formed by the interaction of said reactive site and a reactive functional group which is selected from: an acryloyl moiety, a haloalkyl moiety, an alkene moiety, and an acrylamido moiety.

14. The mutant antibody according to claim 12, wherein said reactive group of said chelate is an acrylamido moiety.

15. The mutant antibody according to claim 1, wherein said metal chelate is a polyaminocarboxylate chelate of a metal ion selected from the group consisting of transition metal ions and lanthanide ions.

16. A pharmaceutical composition comprising the mutant antibody according to claim 9, and a pharmaceutically acceptable carrier.

17. A mutant antibody comprising a reactive site containing a cysteine residue not present in the wild-type of said antibody and six complementarity determining regions (CDRs) that recognize a metal chelate or portions thereof, wherein said cysteine is in a position proximate to or within said complementarity-determining regions, wherein said cysteine residue is the mutation and wherein said reactive site interacts with a reactive group on said metal chelate.

18. A mutant antibody comprising a reactive site not present in the wild-type of said antibody and six complementarity determining regions (CDRs) that specifically bind a metal chelate, wherein said reactive site is in a position proximate to or within said complementarity-determining regions,
wherein said reactive site is the mutation and,
wherein said reactive site interacts with a reactive group on the metal chelate selected from carboxyl groups, hydroxyl groups, haloalkyl groups, dienophile groups, aldehyde groups, ketone groups, sulfonyl halide groups, thiol groups, amine groups, sulfhydryl groups, alkene groups, and epoxide groups.

19. A mutant antibody comprising a reactive site not present in the wild-type of said antibody and six complementarity determining regions (CDRs) that recognize a metal chelate or portions thereof, wherein said reactive site is in a position proximate to or within said complementarity-determining regions,
wherein said reactive site is introduced by mutagenizing a nucleic acid encoding said wild-type of said antibody and,
wherein said reactive site interacts with a reactive group on said metal chelate and said reactive group is selected from carboxyl groups, hydroxyl groups, haloalkyl groups, dienophile groups, aldehyde groups, ketone groups, sulfonyl halide groups, thiol groups, amine groups, sulfhydryl groups, alkene groups, and epoxide groups.

20. A mutant antibody comprising a reactive site not present in the wild-type of said antibody and six complementarity determining regions (CDRs) that specifically bind a metal chelate, wherein said reactive site is in a position proximate to or within said complementarity-determining regions,
wherein said reactive site is introduced by mutagenizing a nucleic acid encoding said wild-type of said antibody, and
wherein said reactive site interacts with a reactive group on the metal chelate selected from carboxyl groups, hydroxyl groups, haloalkyl groups, dienophile groups, aldehyde groups, ketone groups, sulfonyl halide groups, thiol groups, amine groups, sulfhydryl groups, alkene groups, and epoxide groups.

* * * * *

UNITED STATES PATENT AND TRADEMARK OFFICE
CERTIFICATE OF CORRECTION

| | |
|---|---|
| PATENT NO. | : 7,118,745 B1 |
| APPLICATION NO. | : 09/671953 |
| DATED | : October 10, 2006 |
| INVENTOR(S) | : Claude F. Meares et al. |

Page 1 of 1

It is certified that error appears in the above-identified patent and that said Letters Patent is hereby corrected as shown below:

IN THE SPECIFICATION

Col. 1, beginning at line 20, delete the paragraph and insert the following:

--This invention was made with Government support under Grant No. CA016861 awarded by National Institutes of Health. The Government has certain rights in the invention.--

Signed and Sealed this

Fifth Day of January, 2010

David J. Kappos
*Director of the United States Patent and Trademark Office*

SEQUENCE LISTING

<160> NUMBER OF SEQ ID NOS: 23

<210> SEQ ID NO 1
<211> LENGTH: 753
<212> TYPE: DNA
<213> ORGANISM: Artificial Sequence

```
<220> FEATURE:
<223> OTHER INFORMATION: Description of Artificial Sequence:nucleic acid
      that encodes Fab heavy chain of CHA255

<400> SEQUENCE: 1
agatctgaag tgacgctggt ggagtctagg ggagactcag tgaagcctgg agggttcctg      60
aaactctcct gtgcagcctc tggattcact ttaagtggtg aaaccatgtc ttgggttcgc     120
cagactccgg agaagaggct ggagtgggtc acaaccactc ttagtggtgg tggtttcacc     180
ttctattcag ccagtgtgaa gggtcgtttc accatctcca gagacaatgc cagaacaac      240 ctctatctac aactgaatag tctgaggtct gaggacacgg ccttgtattt ctgtgcaagt     300
catcggtttg ttcactgggg ccacgggact ctggtcactg tctctgcagc caaaacgacg     360
ggcccatcgt tcttcccct ggcaccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcaag actctacttc     540
ctcagcagcg tggtgaccgt gcccttcaac agcttgggca cccagaccta catctgcaac     600
gtgaatcaca agcccagcaa caccaaggtg gacaagaaag cagagcccaa atcttgtgac     660
aaatctagag ggcccttcga aggtaagcct atccctaacc ctctcctcgg tctcgattct     720
acgcgtaccg gtcatcatca ccatcaccat tga                                  753

<210> SEQ ID NO 2
<211> LENGTH: 657
<212> TYPE: DNA
<213> ORGANISM: Artificial Sequence
<220> FEATURE:
<223> OTHER INFORMATION: Description of Artificial Sequence:nucleic acid
      that encodes light chain mutant with Cys
      substituted for Asn at position 97 of CHA255

<400> SEQUENCE: 2
agatctgctg ttgtgactca ggaatctgca ctcaccacat cacctggtga acagtcaca      60 ctcacttgtc gctcaagtat tgggctgtt acaactagta actatgccaa ctgggtccaa     120
gaaaaaccag atcatttatt cactggtcta ataggtggta ccaataaccg ggctccgggt     180
gttcctgcca gattctcagg ctccctgatt ggagacaagg ctgccctcac catcacaggg     240
gcacagactg aagatgaggc aagatatttc tgtgctctat ggtactcctg cctctgggtr     300
ttcggtggag gaaccaaact gactgtccta agccgwackg tggctgcacc atctgtcttc     360
atcttcccgc catctgatga gcagttgaaa tctggaactg cctctgttgt gtgcctgctg     420
aataacttct atcccagaga ggccaaagta cagtggaagg tggataacgc cctccaatcg     480
ggtaactccc aggagagtgt cacagagcag gacagcaagg acagcaccta cagcctcagc     540
agcaccctga cgctgagcaa agcagactac gagaaacaca agtctacgc ctgcgaagtc     600 acccatcagg gcctgagyty gcccgtcaca aagagcttca caggggaga gtgttaa        657

<210> SEQ ID NO 3
<211> LENGTH: 657
<212> TYPE: DNA
<213> ORGANISM: Artificial Sequence
<220> FEATURE:
<223> OTHER INFORMATION: Description of Artificial Sequence:nucleic acid
      that encodes the unmodified light chain of CHA255

<400> SEQUENCE: 3
agatctgctg ttgtgactca ggaatctgca ctcaccacat cacctggtga acagtcaca      60
```

```
ctcacttgtc gctcaagtat tggggctgtt acaactagta actatgccaa ctgggtccaa    120
gaaaaaccag atcatttatt cactggtcta ataggtggta ccaataaccg ggctccgggt    180
gttcctgcca gattctcagg ctccctgatt ggagacaagg ctgccctcac catcacaggg    240
gcacagactg aagatgaggc aagatatttc tgtgctctat ggtactccaa cctctgggtr    300
ttcggtggag gaaccaaact gactgtccta agccgwackg tggctgcacc atctgtcttc    360
atcttcccgc catctgatga gcagttgaaa tctggaactg cctctgttgt gtgcctgctg    420 ataacttct atcccagaga ggccaaagta cagtggaagg tggataacgc cctccaatcg    480
ggtaactccc aggagagtgt cacagagcag gacagcaagg acagcaccta cagcctcagc    540
agcaccctga cgctgagcaa agcagactac gagaaacaca agtctacgc ctgcgaagtc     600 acccatcagg gcctgagyty gcccgtcaca aagagcttca caggggaga gtgttaa       657
```

<210> SEQ ID NO 4
<211> LENGTH: 657
<212> TYPE: DNA
<213> ORGANISM: Artificial Sequence
<220> FEATURE:
<223> OTHER INFORMATION: Description of Artificial Sequence:nucleic acid
      that encodes light chain mutant with Cys
      substituted for Ser at position 96 of CHA255

<400> SEQUENCE: 4

```
agatctgctg ttgtgactca ggaatctgca ctcaccacat cacctggtga acagtcaca     60 ctcacttgtc gctcaagtat tggggctgtt acaactagta actatgccaa ctgggtccaa    120
gaaaaaccag atcatttatt cactggtcta ataggtggta ccaataaccg ggctccgggt    180
gttcctgcca gattctcagg ctccctgatt ggagacaagg ctgccctcac catcacaggg    240
gcacagactg aagatgaggc aagatatttc tgtgctctat ggtactgcaa cctctgggtr    300
ttcggtggag gaaccaaact gactgtccta agccgwackg tggctgcacc atctgtcttc    360
atcttcccgc catctgatga gcagttgaaa tctggaactg cctctgttgt gtgcctgctg    420 ataacttct atcccagaga ggccaaagta cagtggaagg tggataacgc cctccaatcg    480
ggtaactccc aggagagtgt cacagagcag gacagcaagg acagcaccta cagcctcagc    540
agcaccctga cgctgagcaa agcagactac gagaaacaca agtctacgc ctgcgaagtc     600 acccatcagg gcctgagyty gcccgtcaca aagagcttca caggggaga gtgttaa       657
```

<210> SEQ ID NO 5
<211> LENGTH: 218
<212> TYPE: PRT
<213> ORGANISM: Artificial Sequence
<220> FEATURE:
<223> OTHER INFORMATION: Description of Artificial Sequence:polypeptide
      sequence of mutant light chain with Cys
      substituted for Asn at position 97 of CHA255
<220> FEATURE:
<221> NAME/KEY: MOD_RES
<222> LOCATION: (207)
<223> OTHER INFORMATION: Xaa = any amino acid

<400> SEQUENCE: 5

Arg Ser Ala Val Val Thr Gln Glu Ser Ala Leu Thr Thr Ser Pro Gly
1               5                   10                  15

Glu Thr Val Thr Leu Thr Cys Arg Ser Ser Ile Gly Ala Val Thr Thr
            20                  25                  30

Ser Asn Tyr Ala Asn Trp Val Gln Glu Lys Pro Asp His Leu Phe Thr
        35                  40                  45

```
Gly Leu Ile Gly Gly Thr Asn Asn Arg Ala Pro Gly Val Pro Ala Arg
 50                  55                  60

Phe Ser Gly Ser Leu Ile Gly Asp Lys Ala Ala Leu Thr Ile Thr Gly
 65                  70                  75                  80

Ala Gln Thr Glu Asp Glu Ala Arg Tyr Phe Cys Ala Leu Trp Tyr Ser
                 85                  90                  95

Cys Leu Trp Val Phe Gly Gly Gly Thr Lys Leu Thr Val Leu Ser Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Xaa Pro
        195                 200                 205

Val Thr Lys Ser Phe Asn Arg Gly Glu Cys
    210                 215

<210> SEQ ID NO 6
<211> LENGTH: 218
<212> TYPE: PRT
<213> ORGANISM: Artificial Sequence
<220> FEATURE:
<223> OTHER INFORMATION: Description of Artificial Sequence:polypeptide
      sequence of unmodified light chain of CHA255
<220> FEATURE:
<221> NAME/KEY: MOD_RES
<222> LOCATION: (207)
<223> OTHER INFORMATION: Xaa = any amino acid

<400> SEQUENCE: 6

Arg Ser Ala Val Val Thr Gln Glu Ser Ala Leu Thr Thr Ser Pro Gly
  1               5                  10                  15

Glu Thr Val Thr Leu Thr Cys Arg Ser Ser Ile Gly Ala Val Thr Thr
             20                  25                  30

Ser Asn Tyr Ala Asn Trp Val Gln Glu Lys Pro Asp His Leu Phe Thr
         35                  40                  45

Gly Leu Ile Gly Gly Thr Asn Asn Arg Ala Pro Gly Val Pro Ala Arg
 50                  55                  60

Phe Ser Gly Ser Leu Ile Gly Asp Lys Ala Ala Leu Thr Ile Thr Gly
 65                  70                  75                  80

Ala Gln Thr Glu Asp Glu Ala Arg Tyr Phe Cys Ala Leu Trp Tyr Ser
                 85                  90                  95

Asn Leu Trp Val Phe Gly Gly Gly Thr Lys Leu Thr Val Leu Ser Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
```

-continued

```
                165                 170                 175
Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Xaa Pro
        195                 200                 205

Val Thr Lys Ser Phe Asn Arg Gly Glu Cys
    210                 215

<210> SEQ ID NO 7
<211> LENGTH: 218
<212> TYPE: PRT
<213> ORGANISM: Artificial Sequence
<220> FEATURE:
<223> OTHER INFORMATION: Description of Artificial Sequence:polypeptide
      sequence of mutant light chain with Cys
      substituted for Ser at position 96 of CHA255
<220> FEATURE:
<221> NAME/KEY: MOD_RES
<222> LOCATION: (207)
<223> OTHER INFORMATION: Xaa = any amino acid

<400> SEQUENCE: 7

Arg Ser Ala Val Val Thr Gln Glu Ser Ala Leu Thr Thr Ser Pro Gly
  1               5                  10                  15

Glu Thr Val Thr Leu Thr Cys Arg Ser Ser Ile Gly Ala Val Thr Thr
             20                  25                  30

Ser Asn Tyr Ala Asn Trp Val Gln Glu Lys Pro Asp His Leu Phe Thr
         35                  40                  45

Gly Leu Ile Gly Gly Thr Asn Asn Arg Ala Pro Gly Val Pro Ala Arg
     50                  55                  60

Phe Ser Gly Ser Leu Ile Gly Asp Lys Ala Ala Leu Thr Ile Thr Gly
 65                  70                  75                  80

Ala Gln Thr Glu Asp Glu Ala Arg Tyr Phe Cys Ala Leu Trp Tyr Cys
                 85                  90                  95

Asn Leu Trp Val Phe Gly Gly Gly Thr Lys Leu Thr Val Leu Ser Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Xaa Pro
        195                 200                 205

Val Thr Lys Ser Phe Asn Arg Gly Glu Cys
    210                 215

<210> SEQ ID NO 8
<211> LENGTH: 250
<212> TYPE: PRT
<213> ORGANISM: Artificial Sequence
<220> FEATURE:
<223> OTHER INFORMATION: Description of Artificial Sequence:polypeptide
      sequence of unmodified heavy chain of CHA255

<400> SEQUENCE: 8
```

```
Arg Ser Glu Val Thr Leu Val Glu Ser Arg Gly Asp Ser Val Lys Pro
 1               5                  10                  15

Gly Gly Phe Leu Lys Leu Ser Cys Ala Ala Ser Gly Phe Thr Leu Ser
             20                  25                  30

Gly Glu Thr Met Ser Trp Val Arg Gln Thr Pro Glu Lys Arg Leu Glu
         35                  40                  45

Trp Val Thr Thr Thr Leu Ser Gly Gly Phe Thr Phe Tyr Ser Ala
     50                  55                  60

Ser Val Lys Gly Arg Phe Thr Ile Ser Arg Asp Asn Ala Gln Asn Asn
 65                  70                  75                  80

Leu Tyr Leu Gln Leu Asn Ser Leu Arg Ser Glu Asp Thr Ala Leu Tyr
                 85                  90                  95

Phe Cys Ala Ser His Arg Phe Val His Trp Gly His Gly Thr Leu Val
            100                 105                 110

Thr Val Ser Ala Ala Lys Thr Thr Gly Pro Ser Val Phe Pro Leu Ala
            115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Arg Leu Tyr Phe Leu Ser Ser Val Val Thr Val Pro Phe Asn Ser Leu
                180                 185                 190

Gly Thr Gln Thr Tyr Ile Cys Asn Val Asn His Lys Pro Ser Asn Thr
            195                 200                 205

Lys Val Asp Lys Lys Ala Glu Pro Lys Ser Cys Asp Lys Ser Arg Gly
210                 215                 220

Pro Phe Glu Gly Lys Pro Ile Pro Asn Pro Leu Leu Gly Leu Asp Ser
225                 230                 235                 240

Thr Arg Thr Gly His His His His His
                245                 250

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:T7 promoter
      primer

<400> SEQUENCE: 9
ctaatacgac tcactatagg g                                            21

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence:K XbaI
      primer

<400> SEQUENCE: 10
ctgcaggtcg actctagagg atctactagt                                   30

<210> SEQ ID NO 11
<211> LENGTH: 35
<212> TYPE: DNA
```

```
<213> ORGANISM: Artificial Sequence
<220> FEATURE:
<223> OTHER INFORMATION: Description of Artificial Sequence:mutagenic
      site

<400> SEQUENCE: 11
catgcctgca ggtcgactct agaggatcta ctagt                           35

<210> SEQ ID NO 12
<211> LENGTH: 39
<212> TYPE: DNA
<213> ORGANISM: Artificial Sequence
<220> FEATURE:
<223> OTHER INFORMATION: Description of Artificial Sequence:mutagenic
      site

<400> SEQUENCE: 12
ttctgtgctc tatggtacag caacctctgg gtattcggt                       39

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence:mutagenesis
      primer S95C

<400> SEQUENCE: 13
atacccagag gttgcagtac catagagcac                                 30

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence:U-19 primer

<400> SEQUENCE: 14
ggttttccca gtcacgacg                                             19

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence:mutagenesis
      primer N96C

<400> SEQUENCE: 15
atacccagag gcagctgtac catagagcac                                 30

<210> SEQ ID NO 16
<211> LENGTH: 360
<212> TYPE: DNA
<213> ORGANISM: Artificial Sequence
<220> FEATURE:
<223> OTHER INFORMATION: Description of Artificial Sequence:V-H sequence
      of CHA255
<220> FEATURE:
<221> NAME/KEY: CDS
<222> LOCATION: (1)..(360)

<400> SEQUENCE: 16 gaa gtg acg ctg gtg gag tct ggg gga gac tca gtg aag cct gga ggg    48
Glu Val Thr Leu Val Glu Ser Gly Gly Asp Ser Val Lys Pro Gly Gly
 1               5                  10                  15 tcc ctg aaa ctc tcc tgt gca gcc tct gga ttc act tta agt ggt gaa    96
```

```
Ser Leu Lys Leu Ser Cys Ala Ala Ser Gly Phe Thr Leu Ser Gly Glu
            20                  25                  30 acc atg tct tgg gtt cgc cag act ccg gag aag agg ctg gag tgg gtc      144
Thr Met Ser Trp Val Arg Gln Thr Pro Glu Lys Arg Leu Glu Trp Val
        35                  40                  45 gca acc act ctt agt ggt ggt ggt ttc acc ttc tat tca gcc agt gtg      192
Ala Thr Thr Leu Ser Gly Gly Gly Phe Thr Phe Tyr Ser Ala Ser Val
 50                  55                  60 aag ggt cgt ttc acc atc tcc aga gac aat gcc cag aac aac ctc tat      240
Lys Gly Arg Phe Thr Ile Ser Arg Asp Asn Ala Gln Asn Asn Leu Tyr
 65                  70                  75                  80 cta caa ctg aat agt ctg agg tct gag gac acg gcc ttg tat ttc tgt      288
Leu Gln Leu Asn Ser Leu Arg Ser Glu Asp Thr Ala Leu Tyr Phe Cys
                 85                  90                  95 gca agt cat cgg ttt gtt cac tgg ggc cac ggg act ctg gtc act gtc      336
Ala Ser His Arg Phe Val His Trp Gly His Gly Thr Leu Val Thr Val
            100                 105                 110 tct gca gcc aaa acg aca ccc cca                                      360
Ser Ala Ala Lys Thr Thr Pro Pro
        115                 120

<210> SEQ ID NO 17
<211> LENGTH: 120
<212> TYPE: PRT
<213> ORGANISM: Artificial Sequence
<220> FEATURE:
<223> OTHER INFORMATION: Description of Artificial Sequence:V-H sequence
      of CHA255

<400> SEQUENCE: 17

Glu Val Thr Leu Val Glu Ser Gly Gly Asp Ser Val Lys Pro Gly Gly
 1               5                  10                  15

Ser Leu Lys Leu Ser Cys Ala Ala Ser Gly Phe Thr Leu Ser Gly Glu
            20                  25                  30

Thr Met Ser Trp Val Arg Gln Thr Pro Glu Lys Arg Leu Glu Trp Val
        35                  40                  45

Ala Thr Thr Leu Ser Gly Gly Gly Phe Thr Phe Tyr Ser Ala Ser Val
 50                  55                  60

Lys Gly Arg Phe Thr Ile Ser Arg Asp Asn Ala Gln Asn Asn Leu Tyr
 65                  70                  75                  80

Leu Gln Leu Asn Ser Leu Arg Ser Glu Asp Thr Ala Leu Tyr Phe Cys
                 85                  90                  95

Ala Ser His Arg Phe Val His Trp Gly His Gly Thr Leu Val Thr Val
            100                 105                 110

Ser Ala Ala Lys Thr Thr Pro Pro
        115                 120

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence:cloning
      primer with XhoI site

<400> SEQUENCE: 18
ggtgctcgag tctgggggag actcagtg                                        28

<210> SEQ ID NO 19
<211> LENGTH: 26
<212> TYPE: DNA
```

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence:cloning primer with ApaI site

<400> SEQUENCE: 19
ggagggcccg tcgttttggc tgcaga                                26

<210> SEQ ID NO 20
<211> LENGTH: 405
<212> TYPE: DNA
<213> ORGANISM: Artificial Sequence
<220> FEATURE:
<223> OTHER INFORMATION: Description of Artificial Sequence:V-L sequence of CHA255 mutant S95C
<220> FEATURE:
<221> NAME/KEY: CDS
<222> LOCATION: (1)..(405)
<220> FEATURE:
<221> NAME/KEY: modified_base
<222> LOCATION: (405)
<223> OTHER INFORMATION: n = g, a, c or t

<400> SEQUENCE: 20

| gct | gtt | gtg | act | cag | gaa | tct | gca | ctc | acc | aca | tca | cct | ggt | gaa | aca | 48 |
|---|---|---|---|---|---|---|---|---|---|---|---|---|---|---|---|---|
| Ala | Val | Val | Thr | Gln | Glu | Ser | Ala | Leu | Thr | Thr | Ser | Pro | Gly | Glu | Thr | |
| 1 | | | | 5 | | | | | 10 | | | | | 15 | | |

| gtc | aca | ctc | act | tgt | cgc | tca | agt | att | ggg | gct | gtt | aca | act | agt | aac | 96 |
|---|---|---|---|---|---|---|---|---|---|---|---|---|---|---|---|---|
| Val | Thr | Leu | Thr | Cys | Arg | Ser | Ser | Ile | Gly | Ala | Val | Thr | Thr | Ser | Asn | |
| | | | 20 | | | | | 25 | | | | | 30 | | | |

| tat | gcc | aac | tgg | gtc | caa | gaa | aaa | cca | gat | cat | tta | ttc | act | ggt | cta | 144 |
|---|---|---|---|---|---|---|---|---|---|---|---|---|---|---|---|---|
| Tyr | Ala | Asn | Trp | Val | Gln | Glu | Lys | Pro | Asp | His | Leu | Phe | Thr | Gly | Leu | |
| | 35 | | | | | 40 | | | | | 45 | | | | | |

| ata | ggt | ggt | acc | aat | aac | cgg | gct | ccg | ggt | gtt | cct | gcc | aga | ttc | tca | 192 |
|---|---|---|---|---|---|---|---|---|---|---|---|---|---|---|---|---|
| Ile | Gly | Gly | Thr | Asn | Asn | Arg | Ala | Pro | Gly | Val | Pro | Ala | Arg | Phe | Ser | |
| 50 | | | | | 55 | | | | | 60 | | | | | | |

| ggc | tcc | ctg | att | gga | gac | aag | gct | gcc | ctc | acc | atc | aca | ggg | gca | cag | 240 |
|---|---|---|---|---|---|---|---|---|---|---|---|---|---|---|---|---|
| Gly | Ser | Leu | Ile | Gly | Asp | Lys | Ala | Ala | Leu | Thr | Ile | Thr | Gly | Ala | Gln | |
| 65 | | | | 70 | | | | | 75 | | | | | 80 | | |

| act | gaa | gat | gag | gca | aga | tat | ttc | tgt | gct | cta | tgg | tac | tgc | aac | ctc | 288 |
|---|---|---|---|---|---|---|---|---|---|---|---|---|---|---|---|---|
| Thr | Glu | Asp | Glu | Ala | Arg | Tyr | Phe | Cys | Ala | Leu | Trp | Tyr | Cys | Asn | Leu | |
| | | | 85 | | | | | 90 | | | | | 95 | | | |

| tgg | gtg | ttc | ggt | gga | gga | acc | aaa | ctg | act | gtc | cta | agc | cag | ccc | aag | 336 |
|---|---|---|---|---|---|---|---|---|---|---|---|---|---|---|---|---|
| Trp | Val | Phe | Gly | Gly | Gly | Thr | Lys | Leu | Thr | Val | Leu | Ser | Gln | Pro | Lys | |
| | | 100 | | | | | 105 | | | | | 110 | | | | |

| tct | tcg | cca | tca | gtc | acc | ctg | ttt | ccg | ccc | tcc | tct | gaa | gag | cta | agc | 384 |
|---|---|---|---|---|---|---|---|---|---|---|---|---|---|---|---|---|
| Ser | Ser | Pro | Ser | Val | Thr | Leu | Phe | Pro | Pro | Ser | Ser | Glu | Glu | Leu | Ser | |
| | 115 | | | | | 120 | | | | | 125 | | | | | |

| ttg | gga | atc | gga | ttc | ccg | ggn | | | | | | | | | | 405 |
|---|---|---|---|---|---|---|---|---|---|---|---|---|---|---|---|---|
| Leu | Gly | Ile | Gly | Phe | Pro | Gly | | | | | | | | | | |
| 130 | | | | 135 | | | | | | | | | | | | |

<210> SEQ ID NO 21
<211> LENGTH: 135
<212> TYPE: PRT
<213> ORGANISM: Artificial Sequence
<220> FEATURE:
<223> OTHER INFORMATION: Description of Artificial Sequence:V-L sequence of CHA255 mutant S95C

<400> SEQUENCE: 21

Ala Val Val Thr Gln Glu Ser Ala Leu Thr Thr Ser Pro Gly Glu Thr
 1               5                  10                  15

Val Thr Leu Thr Cys Arg Ser Ser Ile Gly Ala Val Thr Thr Ser Asn
             20                  25                  30

```
Tyr Ala Asn Trp Val Gln Glu Lys Pro Asp His Leu Phe Thr Gly Leu
            35                  40                  45

Ile Gly Gly Thr Asn Asn Arg Ala Pro Gly Val Pro Ala Arg Phe Ser
     50                  55                  60

Gly Ser Leu Ile Gly Asp Lys Ala Ala Leu Thr Ile Thr Gly Ala Gln
 65              70                  75                  80

Thr Glu Asp Glu Ala Arg Tyr Phe Cys Ala Leu Trp Tyr Cys Asn Leu
                85                  90                  95

Trp Val Phe Gly Gly Gly Thr Lys Leu Thr Val Leu Ser Gln Pro Lys
            100                 105                 110

Ser Ser Pro Ser Val Thr Leu Phe Pro Pro Ser Ser Glu Glu Leu Ser
        115                 120                 125

Leu Gly Ile Gly Phe Pro Gly
        130             135

<210> SEQ ID NO 22
<211> LENGTH: 31
<212> TYPE: DNA
<213> ORGANISM: Artificial Sequence
<220> FEATURE:
<223> OTHER INFORMATION: Description of Artificial Sequence:cloning
      primer with SstI site

<400> SEQUENCE: 22
ctcagagctc gctgttgtga ctcaggaatc t                              31

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence:cloning
      primer with BsiWI site

<400> SEQUENCE: 23
ctcgcatgcg cttaggacag tcagttt                                   27
```